US008354370B2

(12) United States Patent
Kopen et al.

(10) Patent No.: US 8,354,370 B2
(45) Date of Patent: Jan. 15, 2013

(54) ADMINISTERING A BIOLOGICAL COMPOSITION OR COMPOSITIONS ISOLATED FROM SELF-RENEWING COLONY FORMING SOMATIC CELL GROWTH MEDIUM TO TREAT DISEASES AND DISORDERS

(75) Inventors: Gene Kopen, Wynnewood, PA (US); Joseph Wagner, West Chester, PA (US); Vanessa Ragaglia, Newtown Square, PA (US); Baron Heimbach, Philadelphia, PA (US); Richard S. Gore, West Chester, PA (US)

(73) Assignee: Garnet BioTherapeutics, Inc., Malvern, PA (US)

( * ) Notice: Subject to any disclaimer, the term of this patent is extended or adjusted under 35 U.S.C. 154(b) by 1072 days.

(21) Appl. No.: 12/140,065

(22) Filed: Jun. 16, 2008

(65) Prior Publication Data
US 2009/0053183 A1 Feb. 26, 2009

Related U.S. Application Data

(60) Provisional application No. 60/929,151, filed on Jun. 15, 2007, provisional application No. 60/929,152, filed on Jun. 15, 2007, provisional application No. 60/955,204, filed on Aug. 10, 2007, provisional application No. 60/996,093, filed on Nov. 1, 2007.

(51) Int. Cl.
*A61K 38/00* (2006.01)
*A61K 38/37* (2006.01)
*A61K 38/22* (2006.01)
*A61K 38/18* (2006.01)

(52) U.S. Cl. ............ 514/1.1; 514/5.1; 514/5.3; 514/7.6; 514/21.2

(58) Field of Classification Search .................. None
See application file for complete search history.

(56) References Cited

U.S. PATENT DOCUMENTS

| 4,608,199 | A | 8/1986 | Caplan et al. |
| 4,609,551 | A | 9/1986 | Caplan et al. |
| 4,620,327 | A | 11/1986 | Caplan et al. |
| 4,728,641 | A | 3/1988 | Tubaro et al. |
| 5,061,620 | A | 10/1991 | Tsukamoto et al. |
| 5,197,985 | A | 3/1993 | Caplan et al. |
| 5,226,914 | A | 7/1993 | Caplan et al. |
| 5,486,359 | A | 1/1996 | Caplan et al. |
| 5,591,625 | A | 1/1997 | Gerson et al. |
| 5,643,736 | A | 7/1997 | Bruder et al. |
| 5,716,616 | A | 2/1998 | Prockop et al. |
| 5,728,581 | A | 3/1998 | Schwartz et al. |
| 5,733,542 | A | 3/1998 | Haynesworth et al. |
| 5,736,396 | A | 4/1998 | Bruder et al. |
| 5,811,094 | A | 9/1998 | Caplan et al. |
| 5,837,539 | A | 11/1998 | Caplan et al. |
| 5,855,619 | A | 1/1999 | Caplan et al. |
| 5,942,225 | A | 8/1999 | Bruder et al. |
| 5,962,323 | A | 10/1999 | Greenberger et al. |
| 6,010,696 | A | 1/2000 | Caplan et al. |
| 6,087,113 | A | 7/2000 | Caplan et al. |
| 6,174,333 | B1 | 1/2001 | Kadiyala et al. |
| 6,184,035 | B1 | 2/2001 | Csete et al. |
| 6,653,134 | B2 | 11/2003 | Prockop et al. |
| 6,719,972 | B1 | 4/2004 | Gribben et al. |
| 6,974,571 | B2 | 12/2005 | Prockop et al. |
| 7,015,037 | B1 | 3/2006 | Furcht et al. |
| 7,056,738 | B2 | 6/2006 | Prockop et al. |
| 7,659,118 | B2 | 2/2010 | Furcht et al. |
| 7,838,289 | B2 | 11/2010 | Furcht et al. |
| 2001/0034061 | A1 | 10/2001 | Csete et al. |
| 2001/0036642 | A1 | 11/2001 | Asselineau et al. |
| 2002/0058025 | A1 | 5/2002 | Prockop et al. |
| 2002/0146821 | A1 | 10/2002 | Sanchez-Ramos et al. |
| 2002/0168765 | A1 | 11/2002 | Prockop et al. |
| 2003/0003090 | A1 | 1/2003 | Prockop et al. |
| 2003/0003572 | A1 | 1/2003 | Anderson et al. |
| 2003/0003574 | A1 | 1/2003 | Toma et al. |
| 2003/0017587 | A1 | 1/2003 | Rader et al. |
| 2003/0039639 | A1 | 2/2003 | Prockop et al. |
| 2003/0059412 | A1 | 3/2003 | Prockop et al. |
| 2003/0059414 | A1 | 3/2003 | Ho et al. |
| 2003/0059941 | A1 | 3/2003 | Prockop et al. |
| 2003/0202966 | A1 | 10/2003 | Prockop et al. |

(Continued)

FOREIGN PATENT DOCUMENTS

WO WO 99/43286 A2 9/1999

(Continued)

OTHER PUBLICATIONS

Yang et al. IgG1 Cytokines, C3, and Anti-Acetylcholine Receptor with Suppressed Serum Proinflammatory Effect in Murine Myasthenia Gravis Is Associated. J. Immunol., 2005, vol. 175, pp. 2018-2025.*
Voronov et al. IL-1 is required for tumor invasiveness and angiogenesisPNAS, 2003, vol. 100, pp. 2645-2650.*
Akiyomo, Y., et al., "Functional Repair of Demyelinated Spinal Cord Axons in the Adult Rat by Transplantation of Clonal Neural Stem Cells Derived from Adult Human Brain," *Soc. Neurosci. Abstracts* 25:Abstract No. 86.9, Society for Neuroscience, United States (1999)
Alberts, B., et al., eds., *Molecular Biology of the Cell*, Second Edition, p. 746, Garland Publishing Inc., United States, pp. 1219 (1989).
Aldhous, P. and Reich, E.S., "Fresh questions on stem cell findings," NewScientist.com, accessed at http://www.newscientist.com/article.ns?id=mg19325964.600, accessed on Mar. 21, 2007, 3 pages.

(Continued)

Primary Examiner — Deborah Crouch
(74) Attorney, Agent, or Firm — Sterne, Kessler, Goldstein & Fox P.L.L.C.

(57) ABSTRACT

The present invention relates to methods and uses of cells for the prevention and treatment of a wide variety of diseases and disorders and the repair and regeneration of tissues and organs using low passage and extensively passaged in vitro cultured, self-renewing, colony forming somatic cells (CF-SC). For example, adult bone marrow-derived somatic cells (ABM-SC), or compositions produced by such cells, are useful alone or in combination with other components for treating, for example, cardiovascular, neurological, integumentary, dermatological, periodontal, and immune mediated diseases, disorders, pathologies, and injuries.

13 Claims, 28 Drawing Sheets

U.S. PATENT DOCUMENTS

| | | |
|---|---|---|
| 2003/0203484 A1 | 10/2003 | Black et al. |
| 2004/0033214 A1 | 2/2004 | Young et al. |
| 2004/0058412 A1 | 3/2004 | Ho et al. |
| 2004/0058418 A1 | 3/2004 | Endo et al. |
| 2004/0091464 A1 | 5/2004 | Prockop et al. |
| 2004/0107453 A1 | 6/2004 | Furcht et al. |
| 2004/0166097 A1 | 8/2004 | Prockop et al. |
| 2004/0208861 A1 | 10/2004 | Prockop et al. |
| 2005/0181502 A1 | 8/2005 | Furcht et al. |
| 2005/0233452 A1 | 10/2005 | Ho et al. |
| 2005/0283844 A1 | 12/2005 | Furcht et al. |
| 2006/0008450 A1 | 1/2006 | Verfaillie et al. |
| 2006/0030041 A1 | 2/2006 | Furcht et al. |
| 2006/0288431 A1 | 12/2006 | Nakatsuji et al. |
| 2007/0224177 A1 | 9/2007 | Ho et al. |
| 2007/0231309 A1 | 10/2007 | Ho et al. |
| 2007/0264232 A1 | 11/2007 | Ho et al. |

FOREIGN PATENT DOCUMENTS

| | | |
|---|---|---|
| WO | WO 00/24261 A1 | 5/2000 |
| WO | WO 00/69448 A1 | 11/2000 |
| WO | WO 01/04268 A1 | 1/2001 |
| WO | WO 01/11011 A2 | 2/2001 |
| WO | WO 01/34167 A1 | 5/2001 |
| WO | WO 01/59072 A1 | 8/2001 |
| WO | WO 01/78753 A2 | 10/2001 |
| WO | WO 02/18401 A2 | 3/2002 |
| WO | WO 02/34889 A2 | 5/2002 |
| WO | WO 03/025149 A2 | 3/2003 |
| WO | WO 2008/156728 A1 | 12/2008 |

OTHER PUBLICATIONS

Aldhous, P. and Reich, E.S., "Flawed stem cell data withdrawn," NewScientist.com, accessed at http://www.newscientist.com/article.ns?id=mg19325915.200, accessed on Feb. 15, 2007, 2 pages.

Al-Khaldi, A., et al., "Postnatal bone marrow stromal cells elicit a potent VEGF-dependent neoangiogenic response in vivo," *Gene Ther.* 10:621-9, Nature Publishing Group, England (2003).

Aprikyan, A.A., et al., "Erratum," *Exp. Hematol.* 34:1771-2, Elsevier Inc., Netherlands (2006).

Ashhurst, D.E., et al., "The Collagens and Glycosaminoglycans of the Extracellular Matrices Secreted by Bone Marrow Stromal Cells Cultured in vivo in Diffusion Chambers," *J. Orthop. Res.* 8:741-9, Raven Press, Ltd., United States (1990).

Ashton, B.A., et al., "Distribution of Fibroblastic Colony-Forming Cells in Rabbit Bone Marrow and Assay of their Osteogenic Potential by an in vivo Diffusion Chamber Method," *Calcif. Tissue Int.* 36:83-6, Springer-Verlag, United States (1984).

Ashton, B.A., et al., "Formation of Bone and Cartilage by Marrow Stromal Cells in Diffusion Chambers in Vivo," *Clin. Orthop. Relat. Res.* 151:294-307, J. B. Lippincott Co., United States (Sep. 1980).

Azizi, S.A., "Exploiting Nonneural Cells to Rebuild the Nervous System: From Bone Marrow to Brain," *Neuroscientist* 6(5):353-61, Sage Publications, Inc., United States (2000).

Azizi, S.A., et al., "Engraftment and migration of human bone marrow stromal cells implanted in the brains of albino rats—similarities to astrocyte grafts," *Proc. Natl. Acad. Sci. USA* 95:3908-13, National Academy of Sciences, United States (Mar. 1998).

Bab, I., et al., "Assessment of an in vivo Diffusion Chamber Method as a Quantitative Assay for Osteogenesis," *Calcif. Tissue Int.* 3677-82, Springer-Verlag, United States (1984).

Bab, I., et al., "Osteogenesis in in vivo diffusion chamber cultures of human marrow cells," *Bone Miner.* 4:373-86, Elsevier Science Publishers B.V., Netherlands (1988).

Bab, I., et al., "Ultrastructure of Bone and Cartilage Formed in vivo in Diffusion Chambers," *Clin. Orthop. Relat. Res.* 187:243-54, J. B. Lippincott Co., United States (Jul./Aug. 1984).

Baksh, D., et al. "Adult mesenchymal stem cells: characterization, differentiation, and application in cell and gene therapy," *J. Cell. Mol. Med.* 8(3):301-16, Wiley, England (2004).

Batinić, D., et al., "Relationship between differing volumes of bone marrow aspirates and their cellular composition," *Bone Marrow Transplant.* 6: 103-7, Macmillan Press Ltd, England (1990).

Benayahu, D., et al., "Bone Marrow-Derived Stromal Cell Line Expressing Osteoblastic Pheontype In Vitro and Osteogenic Capacity In Vivo," *J. Cell. Physiol.* 140: 1-7, Alan R. Liss, Inc., United States (1989).

Bianco, P., et al., "Bone Marrow Stromal Stem Cells: Nature, Biology, and Potential Applications," *Stem Cells* 19:180-92, AlphaMed Press, United States (2001).

Bruder, S.P., et al., "Growth Kinetics, Self-Renewal, and the Osteogenic Potential of Purified Human Mesenchymal Stem Cells During Extensive Subcultivation and Following Cryopreservation," *J. Cell. Biochem.* 64:278-94, Wiley-Liss, Inc., United States (1997).

Budenz, R.W. and Bernard, G.W., "Osteogenesis and Leukopoiesis Within Diffusion-Chamber Implants of Isolated Bone Marrow Subpopulations," *Am. J. Anatomy* 159: 456-74, Alan R. Liss, Inc., United States (1980).

Caplan, A.I. and Bruder, S.P., "Cell and Molecular Engineering of Bone Regeneration," in *Principles of Tissue Engineering*, p. 603-618, Lanza, R.P., et al., eds., R.G. Landes Company, United States, pp. 808 (1997).

Celis, J.E., ed. *Cell Biology: A Laboratory Handbook*, Second Edition, vol. 1, p. 6-11, Academic Press, United States, pp. 563 (1998).

Chamberlain, G., et al. "Concise Review: Mesenchymal Stem Cells: Their Phenotype, Differentiation Capacity, Immunological Features, and Potential for Homing," *Stem Cells* 25:2739-49, AlphaMed Press, United States (2007).

Check, E., "Stem-cell paper corrected," *Nature* 447:763, Nature Publishing Group, England (2007).

Check, E., "The hard copy," *Nature* 446:485-6, Nature Publishing Group, England (2007).

Chi, K.R., "Adult stem cell figure retracted," The-Scientist.com, accessed at http://www.the-scientist.com/news/home/53279/, accessed on Jun. 26, 2007, 8 pages.

Chopp, M., et al., "Spinal cord injury in rat: treatment with bone marrow stromal cell transplantation," *Neuroreport* 11:3001-5, Lippincott Williams & Wilkins, England (Sep. 2000).

Clayton, A., et al., "Cells Isolated from the Human Cortical Interstitium Resemble Myofibroblasts and Bind Neutrophils in an ICAM-1-Dependent Manner," *J. Am. Soc. Nephrol.* 8:604-15, American Society of Nephrology, United States (1997).

Colter, D.C., et al., "Rapid expansion of recycling stem cells in cultures of plastic-adherent cells from human bone marrow," *Proc. Natl. Acad. Sci.* 97(7):3213-8, National Academy of Sciences, United States (Mar. 2000).

Cooper, L.F., et al., "Incipient Analysis of Mesenchymal Stem-cell-derived Osteogenesis," *J Dent. Res.* 80(1):314-20, American Dental Association, United States (2001).

Coyle, A.J., et al., "Human Mesenchymal Stromal Cells Can Differentiate into Oligodendrocyte Lineage in Transplantation Experiments with MD Rats," *Soc. Neurosci. Abstracts* 26:Abstract No. 415.11, Society for Neuroscience, United States (2000).

Diduch, D.R., et al., "Two Cell Lines from Bone Marrow That Differ in Terms of Collagen Synthesis, Osteogenic Characteristics, and Matrix Mineralization," *J. Bone Joint Surg. Am.* 75:92-105, The Journal of Bone and Joint Surgery, Incorporated, United States (1993).

Eglitis, M.A. and Mezey, E., "Hematopoietic cells differentiate into both microglia and macroglia in the brains of adult mice," *Proc. Natl. Acad. Sci. USA* 94:4080-5, National Academy of Sciences, United States (Apr. 1997).

Eskin, S.G., et al., "Human smooth muscle cells culture from artherosclerotic plaques and uninvolved vessel wall," *In Vitro* 17(8):713-8, Tissue Culture Assn., United States (1981), abstract from NCBI PubMed, PMID No. 7327599.

Ferrari, G., et al., "Muscle Regeneration by Bone Marrow-Derived Myogenic Progenitors," *Science* 279:1528-30, American Association for the Advancement of Science, United States (Mar. 1998).

Freed, J., "Study on uses for adult stem cells was flawed, panel says," Deseretnews.com, accessed at http://www.deseretnews.com/dn/print/1.1442.660198505.00.html, accessed on May 17, 2007, 2 pages.

Friedenstein, A.J., et al., "Bone marrow osteogenic stem cells: in vitro cultivation and transplantation in diffusion chambers," *Cell Tissue Kinet.* 20:263-72, Blackwell Scientific Publications, England (1987).

Gao, J., et al., "Tissue Engineered Fabrication of an Osteochondral Composite Using Rat Bone Marrow-Derived Mesenchymal Stem Cells," *Tissue Eng.* 7(4):363-371, Mary Ann Liebert, Inc., United States (2001).

Gartel, A.L. and Tyner, A.L., "Transcriptional Regulation of the p21$^{(WAF1/CIP1)}$ Gene," *Exp. Cell Res.* 246: 280-9, Academic Press, United States (1999).

Goldman, S. and Raya, T.E., "Rat Infarct Model of Myocardial Infarction and Heart Failure," *J. Cardiac Fail.* 1(2):169-77, Churchill Livingstone, United States (1995).

Gundle, R., et al., "Human Bone Tissue formation in Diffusion Chamber Culture In Vivo by Bone-Derived Cells and Marrow Stromal Fibroblast Cells," *Bone* 16(6):597-601, Elsevier Science Inc., United States (1995).

Hayflick, L. and Moorhead, P.S., "The Serial Cultivation of Human Diploid Cell Strains," *Exp. Cell Res.* 25:585-621, Academic Press, United States (1961).

Haynesworth, S.E., et al., "Cell Surface Antigens on Human Marrow-Derived Mesenchymal Cells Are Detected by Monoclonal Antibodies," *Bone* 13:69-80, Pergamon Press plc, United States (1992).

Haynesworth, S.E., et al., "Characterization of Cells with Osteogenic Potential from Human Marrow," *Bone* 13:81-8, Pergamon Press plc, United States (1992).

Himes, B.T., et al., "Grafting Human Bone Marrow Stromal Cells into Injured Spinal Cord of Adult Rats," *Soc. Neurosci. Abstracts* 25: Abstract No. 86.11, Society for Neuroscience, United States (1999).

Himes, B.T., et al., "Recovery of function following grafting of human bone marrow-derived stromal cells into the injured spinal cord," *Neurorehabil. Neural Repair* 20(2):278-96, Sage Publications, United States (Jun. 2006), abstract from NCBI PubMed, PMID No. 16679505.

Jennemann, R., et al., "Specific Immunization of Using Keyhole Limpet Hemocyanin-Ganglioside Conjugates," *J. Biochem.* 115(6): 1049-52, Oxford University Press, England (1994).

Jiang, Y. et al., "Multipotent progenitor cells can be isolated from postnatal murine bone marrow, muscle, and brain," *Exp. Hematol.* 30: 806-904, Elsevier Science Inc., Netherlands (2002).

Jiang, Y. et al., "Errata: Multipotent progenitor cells can be isolated from postnatal murine bone marrow, muscle, and brain," *Exp. Hematol.* 30:896-904, Elsevier Science Inc., Netherlands (2002).

Jiang, Y., et al., "Pluripotency of mesenchymal stem cells derived from adult marrow," *Nature* 418:41-9, Nature Publishing Group, England (Jul. 2002).

Jiang, Y., et al., "Corrigendum: Pluripotency of mesenchymal stem cells derived from adult marrow," *Nature* 447:879-80, Nature Publishing Group, England (Jun. 2007).

Kaigler, D., et al., "Role of Vascular Endothelial Growth Factor in Bone Marrow Stromal Cell Modulation of Endothelial Cells," *Tissue Eng.* 9(1):95-103, Mary Ann Liebert, Inc., United States (2003).

Kataoka, H. and Urist, M.R., "Transplant of Bone Marrow and Muscle-Derived Connective Tissue Cultures in Diffusion Chambers for Bioassay of Bone Morphogenetic Protein," *Clin. Orthop. Relat. Res.* 286:262-70, Lippincott, Williams & Wilkins, United States (1993).

Kolf, C.M., et al., "Mesechymal stromal cells: Biology of adult mesenchymal stem cells: regulation of niche, self-renewal and differentiation," *Arthritis Res. Ther.* 9:204, BioMed Central Ltd, England (Feb. 2007).

Koller, M.R., et al., "Beneficial Effects of Reduced Oxygen Tension and Perfusion in Long-Term Hematopoietic Cultures," *Ann. NY Acad. Sci.* 665:105-16, New York Academy of Sciences, United States (1992).

Kopen G.C., et al., "Marrow stromal cells migrate throughout forebrain and cerebellum, and they differentiate into astrocytes after injection into neonatal mouse brains," *Proc. Natl. Acad. Sci. USA* 96:10711-6, National Academy Sciences, United States (Sep. 1999).

Krebsbach, P.H., et al., "Bone Formation In Vivo: Comparison of Osteogenesis by Transplanted Mouse and Human Marrow Stromal Fibroblasts," *Transplantation* 63(8):1059-69, Williams & Wilkins, United States (Apr. 1997).

Lee, K.A., et al., "Increased Mesenchymal Cell Density Accompanies Induction of Tropoelastin Expression in Developing Elastic Tissue," *Dev. Dyn.* 200:53-67, Wiley-Liss, Inc., United States (1994).

Lee, K.-D., et al., "In Vitro Hepatic Differentiation of Human Mesenchymal Stem Cells," *Hepatology* 40:1275-84, American Association for the Study of Liver Diseases, United States (Dec. 2004).

Lennon, D.P., et al., "Cultivation of Rat Marrow-Derived Mesenchymal Stem Cells in Reduced Oxygen Tension: Effects on In Vitro and In Vivo Osteochondrogenesis" *J. Cell. Physiol.* 187:345-55, Wiley-Liss, Inc., United States (2001).

Lewis, R.J., Sr., *Hawley's Condensed Chemical Dictionary*, Twelfth Edition, p. 28, Van Nostrand Reinhold, United States, pp. 1275 (1993).

Li, J., et al., "Nontransformed colony-derived stromal cell lines from normal human marrows. II. Phenotypic characterization and differentiation pathway," *Exp. Hematol.* 23:133-41, International Society for Experimental Hematology, United States (1995).

Liechty, K.W., et al, "Human mesenchymal stem cells engraft and demonstrate site-specific differentiation after in utero transplantation in sheep," *Nat. Med.* 6(11):1282-6, Nature Publishing Company, United States (Nov. 2000).

Lodie, T.A., et al., "Systematic Analysis of Reportedly Distinct Populations of Multipotent Bone Marrow-Derived Stem Cells Reveals a Lack of Distinction," *Tissue Eng.* 8(5):739-51, Mary Ann Liebert, Inc., United States (2002).

Majumdar, M.K., et al., "Phenotypic and Functional Comparison of Cultures of Marrow-Derived Mesenchymal Stem Cells (MSCs) and Stromal Cells," *J. Cell. Physiol.* 176:57-66, Wiley-Liss, Inc., United States (1998).

Mardon, H.J., et al., "Development of osteogenic tissue in diffusion chambers from early precursor cells in bone marrow of adult rats," *Cell Tissue Res.* 250:157-65, Springer-Verlag, Germany (1987).

Morris, W., ed. *The American Heritage Dictionary of the English Language*, New College Edition, p. 4, Houghton Mifflin Company, United States, pp. 1550 (1976).

Müller-Ehmsen, J., et al., "Rebuilding a Damaged Heart. Long-Term Survival of Transplanted Neonatal Rat Cardiomyocytes After Myocardial Infarction and Effect on Cardiac Function," *Circulation* 105:1720-6, American Heart Association, Inc., United States (Apr. 2002).

Murry, C.E., et al., "Haematopoietic stem cells do not transdifferentiate into cardiac myocytes in myocardial infarcts," *Nature* 428:664-8, Nature Publishing Group, England (Apr. 2004).

Muschler, G.F., et al., "Aspiration to Obtain Osteoblast Progenitor Cells from Human Bone Marrow: The Influence of Aspiration Volume," *J. Bone Joint Surg. Am.* 79-A(11):1699-1709, Journal of Bone and Joint Surgery (Nov. 1997).

Parnas, D. and Linial, M., "Culture Density Regulates Both the Cholinergic Phenotype and the Expression of the CNTF Receptor in P19 Neurons," *J. Mol. Neurosci.* 8:115-30, Humana Press Inc., United States (1997).

Pereira, R.F., et al., "Cultured adherent cells from marrow can serve as long-lasting precursor cells for bone, cartilage, and lung in irradiated mice," *Proc. Natl. Acad. Sci. USA* 92:4857-61, National Academy of Sciences, United States (May 1995).

Peter, S.J., et al., "Marrow stromal osteoblast function on a poly(propylene fumarate)/beta-tricalcium phosphate biodegradable orthopaedic composite," *Biomaterials* 21(12):1207-13, Butterworth-Heinemann in Association With the Biological Engineering Society, England (2000), abstract from NCBI PubMed, PMID No. 10811302.

Phinney, D.G., et al., "Donor Variation in the Growth Properties and Osteogenic Potential of Human Marrow Stromal Cells," *J. Cell. Biochem.* 75:424-36, Wiley-Liss, Inc., United States (1999).

Phinney, D.G., et al., Plastic Adherent Stromal Cells From the Bone Marrow of Commonly Used Strains of Inbred Mice: Variations in Yield, Growth, and Differentiation *J. Cell. Biochem.* 72:570-85, Wiley-Liss, Inc., United States (1999).

Pittenger, M.F., et al., "Multilineage Potential of Adult Human Mesenchymal Stem Cells," *Science* 284:143-7, American Association for the Advancement of Science, United States (Apr. 1999).

Pittenger, M.F., et al., "Multilineage Potential of Adult Human Mesenchymal Stem Cells, Supplementary Material," ScienceMag.org, accessed at http://www.sciencemag.org/feature/data/983855.dtl, available Apr. 2, 1999, 4 pages.

Prockop, D.J., "Marrow Stromal Cells as Stem Cells for Nonhematopoietic Tissues," *Science* 276:71-4, American Association for the Advancement of Science, United States (Apr. 1997).

Quinones, R.R., "Hematopoietic Engraftment and Graft Failure After Bone Marrow Transplantation," *Am. J. Pediatr. Hematol. Oncol.* 15(1):3-17, Raven Press, Ltd., United States (1993).

Reinecke, H., et al., "Skeletal Muscle Stem Cells Do Not Transdifferentiate Into Cardiomyocytes After Cardiac Grafting," *J. Mol. Cell. Cardiol.* 34:241-9, Elsevier Science Ltd., Netherlands (2002).

Reyes, M., et al., "Purification and ex vivo expansion of postnatal human marrow mesodermal progenitor cells," *Blood* 98(9):2615-25, American Society of Hematology, United States (Nov. 2001).

Reynolds, L.J., et al., "Density and substrata are important in lung type II cell transdifferentiation in vitro," *Int. J. Biochem. Cell Biol.* 31:951-60, Elsevier Science Ltd., Netherlands (1999).

Rithidech, K., et al., "Telomerase Activity in Mouse Myeloid Leukemic Cells and in Cells from Normal Hematopoietic Systems," *Blood Cells Mol. Dis.* 27(2):496-504, Academic Press, United States (Mar./Apr. 2001).

Roisen, K.M., et al., "Murine and Human Adult Olfactory Neuroepithelial Stem Cells," *Soc. Neurosci. Abstracts* 26:Abstract No. 312.7, Society for Neuroscience, United States (2000).

Ross, J.A., et al., "Phenotypic Mapping of Human Mesothelial Cells," *Adv. Perit. Dial.* 14:25-30, Peritoneal Dialysis Bulletin, Inc., Canada (1998).

Sanchez-Ramos, J., et al., "Adult Bone Marrow Stromal Cells Differentiate into Neural Cells in Vitro," *Exp. Neurol.* 164:247-56, Academic Press, United States (2000).

Sanchez-Ramos, J.R, et al., "Bone Marrow Stromal Cells Grafted into Adult Rat Brain Migrate, Organize in Architectonic Patterns and Express Neuronal Markers," *Neurology* 52(Suppl 2):A14, S06.001, Lippincott, Williams & Wilkins, United States (Apr. 1999).

Santalucía, T., et al., "Hypertrophic agonists induce the binding of c-Fos to an AP-1 site in cardiac myocytes: implications for the expression of GLUT1," *Cardiovasc. Res.* 59:639-48, Elsevier B.V., Netherlands (2003).

Schwarz, E.J., et al., "Multipotential Marrow Stromal Cells Transduced to Produce L-DOPA: Engraftment in a Rat Model of Parkinson Disease," *Hum. Gene Ther.* 10:2539-49, Mary Ann Liebert, Inc., United States (Oct. 1999).

Seidel, C.L., et al., "Effect of seeding density and time in culture on vascular smooth muscle cell proteins," *Am. J. Physiol.* 254(2 Pt 1):C235-42, American Physiological Society, United States (1988), abstract from NCBI PubMed, PMID No. 3279797.

Shirinsky, V.P., et al., "Density-related expression of caldesmon and vinculin in cultured rabbit aortic smooth muscle cells, " *Exp. Cell. Res.* 194(2):186-9, Academic Press, United States (1991), abstract from NCBI PubMed, PMID No. 1902791.

Sigma-Aldrich, Inc., "Sigma-Aldrich Leukocyte Separation (Procedure No. 1119)," Sigma-Aldrich, Inc., United States, pp. 1(2003).

Silva, W.A., Jr., et al., "The Profile of Gene Expression of Human Marrow Mesenchymal Stem Cells," *Stem Cells* 21:661-9, AlphaMed Press, United States (2003).

Taupin, P., et al., "FGF-2-Responsive Neural Stem Cell Proliferation Requires CCg, a Novel Autocrine/Paracrine Cofactor," *Neuron* 28:385-97, Cell Press, United States (Nov. 2000).

Thomson, B.M., et al., "Preliminary Characterization of Porcine Bone Marrow Stromal Cells: Skeletogenic Potential, Colony-Forming Activity, and Response to Dexamethasone, Transforming Growth Factor β, and Basic Fibroblast Growth Factor," *J. Bone Min. Res.* 8(10): 1173-83, Mary Ann Liebert, Inc., United States (1993).

Van Den Bos, C., et al., "p21$^{cip1}$ rescues human mesenchymal stem cells from apoptosis induced by low-density culture," *Cell Tissue Res.* 293:463-70, Springer-Verlag, Germany (1998).

Van Den Bos, C., et al., "Human Mesenchymal Stem Cells Respond to Fibroblast Growth Factors," *Hum. Cell.* 10:45-50, The Japan Human Cell Society, Japan (1997).

Verfaillie, C. and Jiang, Y., "Errata," *Exp. Hematol.* 34:809, Elsevier Inc., Netherlands (2006).

Wade, N., "Panel Finds Flawed Data in a Major Stem Cell Report," NYTimes.com, accessed at http://www.nytimes.com/2007/02/28/science/28stem.html?ei=5070&en=b124e855015b1933&ex=117954, available on Feb. 28, 2007, 2 pages.

Woodbury, D., et al., "Adult Rat and Human Bone Marrow Stromal Cells Differentiate Into Neurons," *J. Neurosci. Res.* 61:364-70, Wiley-Liss, Inc., United States (2000).

Woodbury, D., et al., "Adult Rat and Human Bone Marrow Stromal Cells Differentiate Into Neurons," *Soc. Neurosci. Abstracts* 26:Abstract No. 312.9, Society for Neuroscience, United States (2000).

Xu, R., et al., "Serum supplement, inoculum cell density, and accessory cell effects are dependent on the cytokine combination selected to expand human HPCs ex vivo," *Transfusion* 40(11):1299-307, American Association of Blood Banks, United States (2000), abstract from NCBI PubMed, PMID No. 11099656.

Zevin, S., et al., "Nicotine transport in a human choriocarcinoma cell line (JAR)," *J. Pharm. Sci.* 87(6):702-6, American Pharmaceutical Assn., United States (1998), abstract from NCBI PubMed, PMID No. 9607946.

Declaration of Gene Kopen under 37 C.F.R. § 1.132, submitted May 18, 2007, with accompanying exhibits A-E as filed in co-pending U.S. Appl. No. 09/960,244, filed Sep. 21, 2001.

Second Declaration of Gene Kopen under 37 C.F.R. § 1.132, submitted Mar. 5, 2008, with accompanying exhibits A-E as filed in co-pending U.S. Appl. No. 09/960,244, filed Sep. 21, 2001.

Supplementary Partial European Search Report for European Patent Application No. EP 02 77 8303, European Patent Office, Germany, mailed on Aug. 24, 2006.

European Search Report for European Patent Application No. EP 02 778 303.4, European Patent Office, Germany, mailed on Oct. 30, 2007.

Extended European Search Report for European Patent Application No. EP 08 76 8506, European Patent Office, Germany, mailed Jul. 14, 2010.

Written Opinion for Patent Cooperation Treaty Application No. PCT/US01/27087, European Patent Office, Germany, mailed Jul. 15, 2002.

International Preliminary Examination Report for Patent Cooperation Treaty Application No. PCT/US01/27087, European Patent Office, Netherlands, mailed Oct. 24, 2002.

Written Opinion for Patent Cooperation Treaty Application No. PCT/US02/29971, United States Patent and Trademark Office, United States, mailed May 26, 2004.

International Preliminary Examination Report for Patent Cooperation Treaty Application No. PCT/US02/29971, United States Patent and Trademark Office, United States, mailed Aug. 4, 2004.

Written Opinion of the International Search Authority for Patent Cooperation Treaty Application No. PCT/US08/07488, United States Patent and Trademark Office, United States, mailed Sep. 16, 2008.

International Preliminary Report on Patentability for Patent Cooperation Treaty Application No. PCT/US08/07488, The International Bureau of WIPO, Switzerland, mailed Dec. 17, 2009.

Annex, B.H. "Therapeutic Angiogenesis: A Treatment for the New Millennium or Passing Fad?" *Cardiology Rounds* 6(1):1-6, Brigham and Women's Hospital, United States (2002).

Bao, P., et al., "The Role of Vascular Endothelial Growth Factor in Wound Healing," *J. Surg. Res.* 153(2):347-358, Academic Press, United States (2009).

Boodhwani, M. and Sellke, F.W., "Therapeutic Angiogenesis in Diabetes and Hypercholsterolemia: Influence of Oxidative Stress," *Antioxid. Redox Signal.* 11:1945-1959, Mary Ann Liebert, Inc., United States (2009).

Brissova, M. and Powers, A.C., "Revascularization of Transplanted Islets—Can It Be Improved?" *Diabetes* 57:2269-2271, American Diabetes Association, United States (2008).

Carmeliet, P., "Angiogenesis in health and disease," *Nature Medicine* 9(6):653-660, Nature Publishing Group, England (2003).

Favia, G., et al., "Accelerated Wound Healing of Oral Soft Tissues and Angiogenic Effect Induced by a Pool of Amino Acids Combined to Sodium Hyaluronate (AMINOGAM©)," *J. Biol. Regul. Homeost. Agents 22*: 109-116, Biolife S.A.S., Italy (2008).

Frantz, S., et al., "Innate Immunity and Angiogenesis," *Circ. Res. 96*:15-26, American Heart Association, Inc., United States (2005).

Frödin, M. and Gammeltoft, S., "Insulin-like growth factors act synergistically with basic fibroblast growth factor and nerve growth factor to promote chromaffin cell proliferation," *PNAS 91*:1771-1775, National Academy of Sciences, United States (1994).

Greenhalgh, D.G., et al., "Synergistic actions of platelet-derived growth factor and the insulin-like growth factors in vivo—Enhancement of tissue repair in genetically diabetic mice," *Wound Rep. Reg. 1*:69-81, The Wound Healing Society, United States (1993).

Ju, Y-J., et al., "Effects of Local Administration of Vascular Endothelial Growth Factor on Properties of the in Situ Frozen-Thawed Anterior Cruciate Ligament in Rabbits," *Am. J. Sports Med. 34(1)*:84-91, Williams & Wilkins, United States (2006).

Lynch, S.R. et al., "Growth Factors in Wound Healing—Single and Synergistic Effects on Partial Thickness Porcine Skin Wounds," *J. Clin. Invest. 84*:640-646, American Society for Clinical Investigation, Inc., United States (1989).

Unemori, E.N., et al., "Interleukin-1 and Transforming Growth Factor-$\alpha$: Synergistic Stimulation of Metalloproteinases, $PGE_2$, and Proliferation in Human Fibroblasts," *Experimental Cell Research 210*:166-171, Academic Press, Inc., United States (1994).

Voelkel, N.F., et al., "Angiogenesis in Chronic Lung Disease," *CHEST 131*:874-879, American College of Chest Physicians, United States (2007).

Voronov, E., et al., "IL-1 is required for tumor invasiveness and angiogenesis," *PNAS 100(5)*:2645-2650, National Academy of Sciences, United States (2003).

Xiong, Y., et al, "Neurorestorative Treatments for Traumatic Brain Injury," *Discov. Med. 10(54)*:434-442, Discovery Medicine, United States (2010).

Yang, H., et al., "IL-1 Receptor Antagonist-Mediated Therapeutic Effect in Murine Myasthenia Gravis Is Associated with Suppressed Serum Proinflammatory Cytokines, C3, and Anti-Acetylcholine Receptor IgG1," *Journal of Immunology 175*:2018-2025, American Association of Immunologists, United States (2005).

Yu, C., et al., "Tne Different Effects of TGF-$\beta$1, VEGF and PDGF on the Remodeling of the Anterior Cruciate Ligament Graft," in *Targets in Gene Therapy*, pp. 389-396, Y. You, ed., InTech, Croatia (2011).

\* cited by examiner

ADMINISTERING A BIOLOGICAL COMPOSITION OR COMPOSITIONS ISOLATED FROM SELF-RENEWING COLONY FORMING SOMATIC CELL GROWTH MEDIUM TO TREAT DISEASES AND DISORDERS

CROSS-REFERENCE TO RELATED APPLICATIONS

This application claims benefit under 35 U.S.C. §119(e) of U.S. Provisional Patent Application Nos. 60/929,151 and 60/929,152 (each filed Jun. 15, 2007); U.S. Provisional Patent Application No. 60/955,204 (filed Aug. 10, 2007); and, U.S. Provisional Patent Application No. 60/996,093 (filed on Nov. 1, 2007). Each of the above-referenced patent applications are hereby incorporated by reference in their entirety.

BACKGROUND OF THE INVENTION

The present invention relates generally to the generation and use of in vitro cultured self-renewing colony forming somatic cells (CF-SC), and compositions produced by such cells, for the treatment of a variety of diseases and disorders. One example of such CF-SC are adult human bone marrow-derived somatic cells (hABM-SC).

The present invention also relates to manipulation of CF-SC cell populations during cultivation to modulate (i.e., up- or down-regulate) production of various soluble or secreted compositions produced by in vitro cultured and expanded self-renewing colony forming cells.

The field of the invention also relates to cell-based and tissue-engineering therapies; particularly, methods of using and/or administering CF-SC, or compositions produced by such cells, including administration via incorporation in, or mixture with, pharmaceutically acceptable carriers (such as a pharmaceutically acceptable solution or a transient, permanent, or biodegradable matrix).

Cell Based Therapies

There are two major options in using cell-based therapies to manage and treat chronic and acute tissue damage in which the overall objective is the functional and/or cosmetic restoration of damaged tissue. These cell based therapy options include: 1) Cell Replacement—Use of cells to replace damaged tissue by establishing long-term engraftment; and 2) Supply Trophic Factors—Use of cells and compositions produced by cells (e.g., growth factors) to stimulate endogenous repair mechanisms through release of factors delivered or produced by cells without long-term engraftment.

The present invention relates to use of cell based therapies without relying on long-term cell engraftment. In particular, the invention relates to use of cells, and compositions produced by cells, in the treatment of various diseases and disorders; particularly those involving tissues and organs with limited self-renewal capability (such as, for example, neurological and cardiac tissues and organs).

Cell-based therapeutic options in managing and treating tissue damage also present the possibility for use of autologous or allogeneic cells. Each of these have certain advantages and disadvantages. Use of autologous cells involves the following factors or parameters:

Patient is the donor;
Requires manufacture of cell product on a patient-by-patient basis;
Variability in the identity, purity and potency of cell product; and,
Lag time between clinical decision to treat and availability of cells for transplant.

In contrast, the use of allogeneic cells involves the following factors or parameters:

Donor is second party (i.e., donor is not the patient);
Risk associated with donor variability;
Multiple patients treatable per manufactured batch of cell product;
Increased consistency of identity, purity and potency of cell product; and,
Decreased lag time between clinical decision to treat and availability of cell product.

The present invention relates primarily to treatments involving use of allogeneic cells. However, it would also be equally possible to perform these same treatments using autologous cells.

Organ and Tissue Repair

The regenerative potential of certain tissues in the mammalian body has been known for centuries, for example tissues like skin and bone are known to repair themselves after injury. However, a number of conditions and diseases of the central nervous system (i.e., brain and spinal cord), peripheral nervous system and heart adversely affect humans because of the deficit of regenerative capacity in the effected tissues. These conditions and diseases include, for example, spinal cord injury, amyotrophic lateral sclerosis (ALS), Parkinson's disease, stroke, Huntington's disease, traumatic brain injury, brain tumors, Fabry Disease, heart diseases (such as congestive heart failure and myocardial infarction). Clinical management strategies, for example, frequently focus on the prevention of further damage or injury rather than replacement or repair of the damaged tissue (e.g., neurons, glial cells, cardiac muscle); include treatment with exogenous steroids and synthetic, non-cellular pharmaceutical drugs; and have varying degrees of success which may depend on the continued administration of the steroid or synthetic drug.

For example, the majority of spinal cord injuries are compression injuries with the remaining cases involving complete transection of the spinal cord. Current therapeutic treatments for spinal cord injury include the prevention of additional spinal cord injury by physically stabilizing the spine through surgical and non-surgical procedures and by inhibiting the inflammatory response with steroidal therapy.

Additionally, aging is a major negative component to nearly every common disease affecting mammals, and one of the principle features of aging in a degeneration of many tissue including those of skin, bone, eye, brain, liver, kidney, heart, vasculature, muscle, et cetera. Furthermore, the already limited regenerative capacity of certain tissues of the body is known to decline with age, tissue maintenance and repair mechanisms in almost every tissue decline over the course of life.

Thus, there is a need to develop new, improved and effective methods of treatment for diseases and conditions, in particular, neurological and cardiac diseases and age-related degenerative conditions in humans.

Erythropoiesis

Hematopoietic cells in a healthy human or other mammal do not ordinarily have a limited long-term self-renewal capability. However, the potential for catastrophic loss of blood (or need otherwise for a supplemental supply of blood) combined with limited supplies of donor blood, entails that methods for enhancing, maintaining, or generating red blood supplies in vitro are quite desirable.

Blood is a highly specialized circulating tissue consisting of several types of cells suspended in a fluid medium known as plasma. The cellular constituents are: red blood cells (erythrocytes), which carry respiratory gases and give it its red color because they contain hemoglobin (an iron-containing protein that binds oxygen in the lungs and transports it to tissues in the body), white blood cells (leukocytes), which fight disease, and platelets (thrombocytes), cell fragments which play an important part in the clotting of the blood. Medical terms related to blood often begin with hemo- or hemato- (BE: haemo- and haemato-) from the Greek word "haima" for "blood." Blood cells are produced in the bone marrow; in a process called hematopoiesis. Blood cells are degraded by the spleen and liver. Healthy erythrocytes have a plasma half-life of 120 days before they are systematically replaced by new erythrocytes created by the process of hematopoiesis. Blood transfusion is the most common therapeutic use of blood. It is usually obtained from human donors. As there are different blood types, and transfusion of the incorrect blood may cause severe complications, crossmatching is done to ascertain the correct type is transfused.

A shortage of blood donors and inadequate supplies of red blood cells for transfusion is a common problem in treating patients worldwide. Accordingly, there is a need for new, improved and effective methods of increasing the availability of red blood cells as this would provide a means for alleviating at least some of the global shortages in red blood cell supplies.

Skin

The present invention relates in part to treatment of skin wounds. There are currently available a number of different treatments for wounds of the skin such as epidermal replacement products, dermal replacement products, artificial skin products, and wound dressings. Examples of some of these are described briefly below.

Epidermal Replacement Products

According to the manufacturer, EPICEL™ (Genzyme Corp., Cambridge, Mass.) is composed of autologous epidermal cells skin grown from biopsy of patients own skin for treatment of burns. Cells are co-cultured with mouse feeder cell line into sheets of autologous epidermis.

According to the manufacturer, MYSKIN™ (CellTran LTD, Sheffield, S1 4DP United Kingdom) is a cultured autologous epidermal substitute for the treatment of burns, ulcers and other non-healing wounds. MYSKIN™ contains living cells expanded from the tissue of individual patients. MYSKIN™ comprises a layer of keratinocytes (epidermal cells) on an advanced polymer-like coating which facilitates the transfer of cells into the wound where they can initiate healing. MYSKIN™ uses a medical grade silicone substrate layer to support cell delivery, wound coverage and allow exudate management.

According to the manufacturer, EPIDEX™ (Modex Therapeutics Ltd, Lausanne, Switzerland) is an autologous epidermal skin equivalent that is grown directly from stem and pre-cursor cells derived from hair taken directly from a patient in a non-surgical procedure.

According to the manufacturer, CELLSPRAY™ (Clinical Cell Culture Europe Ltd, Cambridge CB2 1NL, United Kingdom) is a cultured epithelial autograft suspension that is sprayed onto injured skin in order to provide a rapid epidermal cover, promote healing and optimize scar quality.

Dermal Replacement Products

According to the manufacturer, INTEGRA™ Dermal Regeneration Template (Integra LifeSciences Corporation, Plainsboro, N.J.) is a bilayer membrane system for skin replacement. The dermal replacement layer is made of a porous matrix of fibers of cross-linked bovine tendon collagen and a glycosaminoglycan (chondroitin-6-sulfate) that is manufactured with a controlled porosity and defined degradation rate. The temporary epidermal substitute layer is made of synthetic polysiloxane polymer (silicone) and functions to control moisture loss from the wound. The collagen dermal replacement layer serves as a matrix for the infiltration of fibroblasts, macrophages, lymphocytes, and capillaries derived from the wound bed.

According to the manufacturer, DERMAGRAFT™ (Advanced Biohealing, La Jolla, Calif.) Allogeneic newborn fibroblasts grown on a biodegradable mesh scaffold, indicated for full-thickness diabetic ulcers.

According to the manufacturer, PERMACOL™ (Tissue Science Laboratories, Inc. Andover, Mass. 01810) Permacol™ surgical implant is collagen-derived from porcine dermis which, when implanted in the human body, is non-allergenic and long-lasting.

According to the manufacturer, TRANSCYTE™ (Advanced Biohealing, La Jolla, Calif. 92037) TRANSCYTE™ is a human foreskin-derived fibroblast temporary skin substitute (allogeneic). The product consists of a polymer membrane and newborn human fibroblast cells cultured under aseptic conditions in vitro on a nylon mesh. Prior to cell growth, this nylon mesh is coated with porcine dermal collagen and bonded to a polymer membrane (silicone). This membrane provides a transparent synthetic epidermis when the product is applied to the burn. The human fibroblast-derived temporary skin substitute provides a temporary protective barrier. TRANSCYTE™ is transparent and allows direct visual monitoring of the wound bed.

According to the manufacturer, RENGRANEX™ Gel (Ortho-McNeil Pharmaceutical, Inc.© ETHICON, INC.) is a topical wound care product made of recombinant PDGF in a gel.

Artificial Skin Products (Epidermal and Dermal Combination Products)

According to the manufacturer, PERMADERM™ (Cambrex Bio Science Walkersville, Inc., Walkersville, Md.) PERMADERM™ is constructed from autologous epidermal and dermal layers of the skin and is indicated for the treatment of severe burns. The product is reported to be pliable and to grow with the patient.

According to the manufacturer, ORCEL™ (Ortec International, New York, N.Y.) Bilayered construct made from allogeneic epidermal cells and fibroblasts cultured in bovine collagen, indicated for split-thickness burns. The manufacturer reports no evidence of product-derived DNA detectable in two human patients treated with product at 2 or 3 weeks, respectively.

According to the manufacturer, APLIGRAF™ (Smith & Nephew, London, WC2N 6LA United Kingdom) Allogeneic epidermal cells and fibroblasts cultured in bovine collagen, indicated for venous leg ulcers.

Wound Dressings

According to the manufacturer, 3M™ TEGADERM™ Transparent Film Dressing (3M, St. Paul, Minn.) is a breathable film that provides a bacterial and viral barrier to outside contaminants.

According to the manufacturer, TISSEEL™ VH Fibrin Sealant (Baxter, Deerfield, Ill.) is indicated for use as an adjunct to hemostasis.

SUMMARY OF THE INVENTION

The present invention relates to the production and use of stable cell populations and compositions produced thereby. The term "stable cell population" as used herein means an isolated, in vitro cultured, cell population that when introduced into a living mammalian organism (such as a mouse, rat, human, dog, cow, etc.) does not result in detectable production of cells which have differentiated into a specialized cell type or cell types (such as a chondrocyte, adipocyte, osteocyte, etc.) and wherein the cells in the cell population express, or maintain the ability to express or the ability to be induced to express, detectable levels of at least one therapeutically useful composition (such as membrane bound or soluble TNF-alpha receptor, IL-1R antagonists, IL-18 antagonists, compositions shown in Table 1A, 1B, 1C, etc.).

Another characteristic of the stable cell populations of the present invention is that the cells do not exhibit ectopic differentiation. The term "ectopic" means "in the wrong place" or "out of place". The term "ectopic" comes from the Greek "ektopis" meaning "displacement" ("ek", out of +"topos", place=out of place). For example, an ectopic kidney, is one that is not in the usual location; or, an extrauterine pregnancy is an "ectopic pregnancy". In the present context, an example of ectopic differentiation would be cells that when introduced into cardiac tissue, produce bone tissue-like calcifications and/or ossifications. This phenomenon has been demonstrated to occur, for example, when mesenchymal stem cells are injected into cardiac tissue. See, Breitbach et al., "Potential Risks of Bone Marrow Cell Transplantation Into Infarcted Hearts", Blood, Vol. 110, No. 4 (August 2007).

The present invention relates to the generation and use of expanded, in vitro cultured, self-renewing colony forming somatic cells (hereinafter referred to as "CF-SC"), and products produced by such cells, for the treatment of a variety of diseases and disorders. Further, the present invention also relates to the generation and use of extensively expanded, in vitro cultured, self-renewing colony forming somatic cells (hereinafter referred to as "exCF-SC"), and products produced by such cells, for the treatment of a variety of diseases and disorders. ExCF-SC are self-renewing colony forming somatic cells (CF-SC) which have undergone at least about 30, at least about 40, or at least about 50 cell population doublings during in vitro cultivation. Hence, self-renewing colony forming somatic cells which have been expanded in vitro are hereinafter referred to as "CF-SC" (such that, unless specified otherwise, this term encompasses both cell populations which have undergone less than about 30 population doublings (e.g., less than about 5, less than about 10, less than about 15, less than about 20, less than about 25 population doublings) and also cell populations which have undergone more than about 30, more than about 40, or more than about 50 populations doublings in vitro). One particular example of CF-SC are adult human bone marrow-derived somatic cells (hereinafter referred to as "ABM-SC"). Further, one particular example of exCF-SC are adult human bone marrow-derived somatic cells which have undergone at least about 30, at least about 40, or at least about 50 cell population doublings during in vitro cultivation (hereinafter referred to as "exABM-SC"). Accordingly, the term "ABM-SC", unless specified otherwise, encompasses both ABM-SC cell populations which have undergone less than about 30 population doublings (e.g., less than about 5, less than about 10, less than about 15, less than about 20, less than about 25 population doublings) and also ABM-SC cell populations which have undergone more than about 30, more than about 40, or more than about 50 populations doublings in vitro).

The term "extensively expanded" as used herein refers to cell populations which have undergone at least about 30 or more cell population doublings and wherein the cells are non-senescent, are not immortalized, and continue to maintain the normal karyotype found in the cell species of origin.

As used herein, the term "substantial capacity for self-renewal" means having the ability to go through numerous cycles of cell division resulting in the production of multiple generations of cell progeny (thus, with each cell division, one cell produces two "daughter cells" wherein at least one daughter cell is capable of further cell division). One measure of "substantial capacity for self-renewal" is indicated by the ability of a cell population to undergo at least about 10, 15, 20, 25, 30, 35, 40, 45, 50 or more cell doublings. Another measure of "substantial capacity for self-renewal" is indicated by maintenance of the ability of a cell population to re-populate, or approach confluence in, a tissue culture vessel after cell culture passaging (when the same or similar culture conditions are maintained). Thus, an example of "substantial capacity for self-renewal" is demonstrated when a cell population continues to re-populate a tissue culture vessel in a period of time of at least about 25%, 50%, 60%, 70%, 80%, 90%, 95% or 100% of the time required for such re-population during early cell culture doublings (such as before a cell population has undergone more than about 10 population doublings). Another measure of "substantial capacity for self-renewal" is maintenance of a consistent rate of population doubling time or of a consistent and relatively rapid rate of population doubling.

As used herein, the term "substantially no multipotent differentiation capacity" means cell populations which cannot differentiate into multiple different types of cells, either in vitro or in vivo. An example of cells which do have substantial multipotent differentiation capacity are hematopoietic stem cells which can differentiate into red blood cells, T-cells, B-cells, platelets, etc. either in vitro or in vivo. Another example of cells which do have substantial multipotent differentiation capacity are mesenchymal stem cells which can differentiate, for example, into osteocytes (bone), adipocytes (fat), or chondrocytes (cartilage). In contrast, cells in a cell population which have "substantially no multipotent differentiation capacity" cannot differentiate into multiple cell types in vitro or when introduced into an organism or target tissue(s) in vivo. In a preferred embodiment of the invention, a cell population with "substantially no multipotent differentiation capacity" is one in which at least about 80%, 90%, 95%, 98%, 99% or 100% of the cells in the cell population cannot be induced to detectably differentiate in vitro or in vivo into more than one cell type. A "unipotent" cell or "unipotent progenitor cell" is an example of a cell which has substantially no multipotent differentiation capacity.

As used herein, "stem cell" means a cell or cells possessing the following two properties: 1) capacity for self-renewal, which is the ability to go through numerous cycles of cell division while maintaining the undifferentiated state; and, 2) differentiation potency, which is the capacity to change into one or more kinds of mature cell types and, upon such change, no longer undergoing cycles of cell division (for example, capacity to change into an osteocyte, adipocyte, chondrocyte, etc.). As used herein, differentiation potency means the cells are either totipotent, pluripotent, multipotent, or unipotent progenitor cells. A "mesenchymal stem cell" is a stem cell of this same definition but wherein said cell has been derived or obtained from mesenchyme tissue (such as, for example, bone marrow, adipose or cartilage). See, Horwitz et al., "Clarification of the nomenclature for MSC: The International Society for Cellular Therapy position statement", Cytotherapy, vol. 7, no. 5, pp. 393-395 (2005); and references cited therein.

As used herein, "totipotent" means cells which can become any type of cell as may be found during any stage of development in the organism of the cells origin. Totipotent cells are typically produced by the first few divisions of the fertilized egg (i.e., following fusion of an egg and sperm cell). Thus, totipotent cells can differentiate into embryonic and extraembryonic cell types.

As used herein, "pluripotent" means cells which can differentiate into cells derived from any of the three germ layers (endoderm, mesoderm, ectoderm) found in the organism of the cells origin.

As used herein, "multipotent" means cells which can produce multiple types (i.e., more than one type) of differentiated cells. A mesenchymal stem cell is an example of a multipotent cell.

As used herein, "unipotent" means cells which can produce only one cell type. Unipotent cells have the property of self-renewal, but can change into only one kind of mature cell type.

As used herein, "normal karyotype" means having a genetic composition comprising chromosomes of the number and of the structure typically found in, and considered normal for, the species from which the cells are derived.

As used herein, "connective tissue" is one of the four types of tissue usually referenced in traditional classifications (the others being epithelial, muscle, and nervous tissue). Connective tissue is involved in organism and organ structure and support and is usually derived from mesoderm. As used herein, "connective tissue" includes those tissues sometimes referred to as "connective tissue proper", "specialized connective tissues", and "embryonic connective tissue".

"Connective tissue proper" includes areolar (or loose) connective tissue, which holds organs and epithelia in place and has a variety of proteinaceous fibres, including collagen and elastin. Connective tissue proper also includes dense connective tissue (or, fibrous connective tissue) which forms ligaments and tendons.

"Specialized connective tissue" includes blood, bone, cartilage, adipose and reticular connective tissue. Reticular connective tissue is a network of reticular fibres (fine collagen, type III) that form a soft skeleton to support the lymphoid organs (lymph nodes, bone marrow, and spleen)

"Embryonic connective tissue" includes mesenchymal connective tissue and mucous connective tissue. Mesenchyme (also known as embryonic connective tissue) is the mass of tissue that develops mainly from the mesoderm (the middle layer of the trilaminar germ disc) of an embryo. Viscous in consistency, mesenchyme contains collagen bundles and fibroblasts. Mesenchyme later differentiates into blood vessels, blood-related organs, and connective tissues. Mucous connective tissue (or mucous tissue) is a type of connective tissue found during fetal development; it is most easily found as a component of Wharton's jelly (a gelatinous substance within the umbilical cord which serves to protect and insulate cells in the umbilical cord).

As used herein, "immortalized" refers to a cell or cell line which can undergo an indefinite number of cell doublings in vitro. Immortalized cells acquire such ability through genetic changes which eliminate or circumvent the natural limit on a cells ability to continually divide. In contrast, "non-immortalized" cells are eukaryotic cells which, when taken directly from the organism and cultured in vitro (producing a "primary cell culture"), can undergo a limited number of cell doublings before senescencing (losing ability to divide) and dying. For example, primary cultures of most types of mammalian, non-immortalized cells can usually undergo a relatively defined but reproducibly limited range of cell doublings (depending on the primary cell type) before differentiating, senescing, or dying.

As used herein "long-term engraftment" means the detectable presence of donor cells residing within (or as part of) target tissue to which (or in which) said cells were delivered after more than about 4 weeks from the time of administration. "More than about 4 weeks" includes time periods of more than about 5, 6, 7, 8, 10, 12, 14, 16, 18, 20, and 24 weeks. "More than about 4 weeks" also includes time periods of more than about 6 months, 8 months, 10 months, 12 months, 18 months, 24 months, 30 months, 36 months, 42 months and 48 months.

The present invention also relates to manipulation of CF-SC and exCF-SC cell populations during cultivation to modulate (i.e., up- or down-regulate) production of various soluble or secreted compositions produced by the in vitro cultured and expanded self-renewing colony forming cells.

The present invention also relates to extensively expanded cell populations which are characterized by loss of ability to differentiate into bone cells (osteocytes). For example, the present invention relates to extensively expanded cell populations which are characterized by loss of ability to generate calcium deposits when cultured under osteoinductive conditions, including with or without cultivation in the presence of the supplemental bone morphogen Noggin (see Example 16). (Mouse and Human Noggin: See, e.g., the U.S. National Center for Biotechnology PubMed Protein Database Accession Nos. NP_032737 and NP_005441 (respectively); see also e.g., Valenzuela, et al., "Identification of mammalian noggin and its expression in the adult nervous system", *J. Neurosci.* 15 (9), 6077-6084 (1995)).

The present invention also relates to extensively expanded cell populations characterized by the loss of ability to differentiate into bone cells and/or loss of ability to generate calcium deposits (as described above), but wherein said cell populations continue to secrete, or maintain the ability to secrete or to be induced to secrete, at least one therapeutically useful composition.

The present invention also relates to cell-based and tissue-engineering therapies; particularly, methods of using and/or administering CF-SC and exCF-SC, or compositions produced by such cells, including administration via incorporation in, or mixture with, pharmaceutically acceptable carriers (such as a pharmaceutically acceptable solution or a transient, permanent, or biodegradable matrix).

The present invention also relates to expanded (i.e., in vitro cultured and passaged) and extensively expanded cell populations which are preferably negative for expression of the STRO-1 cell surface marker. See, e.g., Stewart et al., "STRO-1, HOP-26 (CD63), CD49a and SB-10 (CD166) as markers of primitive human marrow stromal cells and their more differentiated progeny: a comparative investigation in vitro" Cell Tissue Res. 2003 September; 313(3):281-90; and, Dennis et al., "The STRO-1+ marrow cell population is multipotential" Cells Tissues Organs. 2002; 170(2-3):73-82; and, Oyajobi et al., "Isolation and characterization of human clonogenic osteoblast progenitors immunoselected from fetal bone marrow stroma using STRO-1 monoclonal antibody", J Bone Miner Res. 1999 March; 14(3):351-61.

The present invention also relates to manufacture and use of pharmaceutically acceptable compositions containing CF-SC and exCF-SC (for example, ABM-SC and exABM-SC) with additional structural and/or therapeutic components. As one example, CF-SC or exCF-SC (for example, ABM-SC or exABM-SC) and collagen may be combined in a pharmaceutically acceptable solution to generate compositions in liquid, semi-solid, or solid-like forms (matrices) for use, for example, in the treatment, repair, and regeneration of skin disorders (e.g., skin wounds such as burns, abrasions, lacerations, ulcers, infections).]

The present invention relates generally to use of self-renewing cells, referred to herein as colony-forming somatic cells (CF-SC) including extensively passaged colony-forming somatic cells (exCF-SC). Examples of such cells are adult human bone marrow-derived somatic cells (ABM-SC) including extensively passaged adult human bone marrow-derived somatic cells (exABM-SC), for use in treatment of various diseases and disorders; particularly diseases and disorders involving ischemia, trauma, and/or inflammation (such as, for example, heart failure due to acute myocardial infarction (AMI) and stroke).

Self-renewing colony-forming somatic cells (CF-SC) such as adult human bone marrow-derived somatic cells (ABM-SC) as used in the present invention are prepared as described in U.S. Patent Publication No. 20030059414 (U.S. application Ser. No. 09/960,244, filed Sep. 21, 2001) and U.S. Patent Publication No. 20040058412 (U.S. application Ser. No. 10/251,685, filed Sep. 20, 2002). Each of these patent applications are hereby incorporated by reference in their entirety. In particular, CF-SC isolated from a source population of cells (such as, for example, from bone marrow, fat, skin, placenta, muscle, umbilical cord blood, or connective tissue) are cultured under low oxygen conditions (e.g., less than atmospheric) and passaged at low cell densities such that the CF-SC maintain an essentially constant population doubling rate through numerous population doublings. After expansion of the CF-SC to an appropriate cell number, the CF-SC may be used to generate the compositions of the present invention. For example, after expansion of the CF-SC in vitro for at least about 30, at least about 40, or at least about 50 cell population doublings exCF-SC may be used to generate compositions of the present invention. In one embodiment CF-SC and exCF-SC, as used in the present invention, are derived from bone marrow (and are referred to herein as ABM-SC and exABM-SC, respectively).

One embodiment of CF-SC and exCF-SC (such as for example, ABM-SC and exABM-SC, respectively), as used in the present invention, is an isolated cell population wherein the cells of the cell population co-express CD49c and CD90 and wherein the cell population maintains a doubling rate of less than about 30 hours after at least about 30, at least about 40, or at least about 50 cell population doublings.

Another embodiment of CF-SC and exCF-SC (such as for example, ABM-SC and exABM-SC, respectively), as used in the present invention, is an isolated cell population wherein the cells of the cell population co-express CD49c, CD90, and one or more cell surface proteins selected from the group consisting of CD44, HLA Class-1 antigen, and β (beta) 2-Microglobulin, and wherein the cell population maintains a doubling rate of less than about 30 hours after at least about 30, at least about 40, or at least about 50 cell population doublings.

Another embodiment of CF-SC and exCF-SC (such as for example, ABM-SC and exABM-SC, respectively), as used in the present invention, is an isolated cell population wherein the cells of the cell population co-express CD49c and CD90, but are negative for expression of cell surface protein CD10, and wherein the cell population maintains a doubling rate of less than about 30 hour after at least about 30, at least about 40, or at least about 50 cell population doublings.

Another embodiment of CF-SC and exCF-SC (such as for example, ABM-SC and exABM-SC, respectively), as used in the present invention, is an isolated cell population wherein the cells of the cell population co-express CD49c, CD90, and one or more cell surface proteins selected from the group consisting of CD44, HLA Class-1 antigen, and β (beta) 2-Microglobulin, but are negative for expression of cell surface protein CD10, and wherein the cell population maintains a doubling rate of less than about 30 hours after at least about 30, at least about 40, or at least about 50 cell population doublings.

Another embodiment of CF-SC and exCF-SC (such as for example, ABM-SC and exABM-SC, respectively), as used in the present invention, is an isolated cell population wherein the cells of the cell population express one or more proteins selected from the group consisting of soluble proteins shown in Table 1A, 1B and 1C, and wherein the cell population maintains a doubling rate of less than about 30 hours after at least about 30, at least about 40, or at least about 50 cell population doublings.

Damaged tissues and organs may result from, for example, disease (e.g., heritable (genetic) or infectious diseases (such as bacterial, viral, and fungal infections)), physical trauma (such as burns, lacerations, abrasions, compression or invasive tissue and organ injuries), ischemia, aging, toxic chemical exposure, ionizing radiation, and dysregulation of the immune system (e.g., autoimmune disorders).

The present invention encompasses the use of CF-SC and exCF-SC (such as for example, ABM-SC and exABM-SC, respectively), CF-SC and exCF-SC purified protein fractions, supernatants of CF-SC and exCF-SC conditioned media, and fractions of cell-supernatants derived from CF-SC and exCF-SC conditioned media. In one embodiment of the invention, the above mentioned components may be combined with, or introduced into, physiologically compatible biodegradable matrices which contain additional components such as collagen and/or fibrin (for example, purified natural or recombinant human, bovine, or porcine collagen or fibrin), and/or polyglycolic acid (PGA), and/or additional structural or therapeutic compounds. Combination matrices such as these may be administered to the site of tissue or organ damage to promote, enhance, and/or result in repair and/or regeneration of the damaged tissue or organ.

Embodiments of the invention include use of CF-SC and exCF-SC (such as for example, ABM-SC and exABM-SC, respectively), incorporated into pharmaceutically acceptable compositions which may be administered in a liquid, semi-solid, or solid-like state. Embodiments of the invention may be administered by methods routinely used by those skilled in the relevant art, such as for example, by topical application, as spray-on or aerosolized compositions, by injection, and implantation.

Use of CF-SC and exCF-SC (such as for example, ABM-SC and exABM-SC, respectively), cells and compositions produced by these cells as described in the present invention for tissue regenerative therapies may provide a number of benefits compared to previously described tissue regenerative therapies and products. For example, use of the CF-SC and exCF-SC (such as for example, ABM-SC and exABM-SC, respectively), exABM-SC cells and compositions produced thereby provides a means of tissue regenerative therapy which may exhibit reduced adverse immune responses (such as reduced inflammation and T-cell activation; see e.g., Examples 3A, 3B, 5, 18, and 19. Moreover, since ABM-SC and exABM-SCs are immunologically silent, subjects do not need to be HLA-matched or pre-conditioned prior to treatment. See, Example 10, Part II; see also, FIG. 17.

The present invention also relates to the use of CF-SC and exCF-SC (such as expanded and extensively expanded adult human bone marrow-derived somatic cells (human ABM-SC and exABM-SC, respectively)), and the cell products generated by these cells, for inducing, enhancing, and/or maintaining hematopoiesis (in particular, for the in vitro generation and production of red blood cells (erythrocytes) from hematopoietic progenitor cells in a process called erythropoiesis). Thus, another embodiment of the invention encompasses the use of such cells and/or compositions produced by such cells, to induce, enhance, and/or maintain the generation and production of red blood cells (erythrocytes).

Another example of the field of the invention relates to the prevention and treatment of immune, autoimmune, and inflammatory disorders via use of such cells, cell populations, and compositions produced thereby.

In another example, the present invention provides compositions and methods for repair and regeneration of wounds of the skin (i.e., epidermis, dermis, hypodermis); including the manufacture and use of liquid, semi-solid, and solid-like matrices which incorporate CF-SC and exCF-SC (for example, human ABM-SC and exABM-SC), or products generated by such cells, and additional structural or therapeutic compounds.

Exemplary Results of Preclinical Studies

In vivo preclinical pharmacology studies have demonstrated the beneficial effects of ABM-SC in treating myocardial infarction and stroke. For example, in a study investigating the effects of intra-cardiac injection of hABM-SC in a rat model of myocardial infarction (in particular, to determine the efficacy of hABM-SC in restoring cardiac function post-AMI (acute myocardial infarction) and evaluate distribution and disposition of hABM-SC), it was shown that hABM-SC produced a significant improvement in cardiac function and significantly reduced fibrosis. Furthermore, the hABM-SC were not observed to remain in the heart four weeks after cardiac injection, nor in any of the peripheral organs examined eight weeks after injection. Additionally, in a study investigating the safety and efficacy of porcine and human ABM-SC in an AMI model in pigs (in particular, to evaluate the feasibility, safety and efficacy of percutaneous, NOGA™-guided endomyocardial administration of cells through a MYOSTAR™ catheter) it was demonstrated that this particular delivery method was well-tolerated and led to significant improvements in cardiac parameters. Likewise, in a comparison of the method of delivery of hABM-SC and stroke recovery (in particular, to determine efficacy of hABM-SC in promoting neuromotor recovery from ischemic stroke) it was observed that I.V. or intra-cerebral treatment resulted in significant improvements in neuromotor activity.

DESCRIPTION OF THE DRAWINGS

FIG. 36A) and IL-18 binding protein (IL-18BP; FIG. 36B) even in the absence of an inflammatory signal such as TNF-alpha.

DETAILED DESCRIPTION OF THE INVENTION

Figure 1:
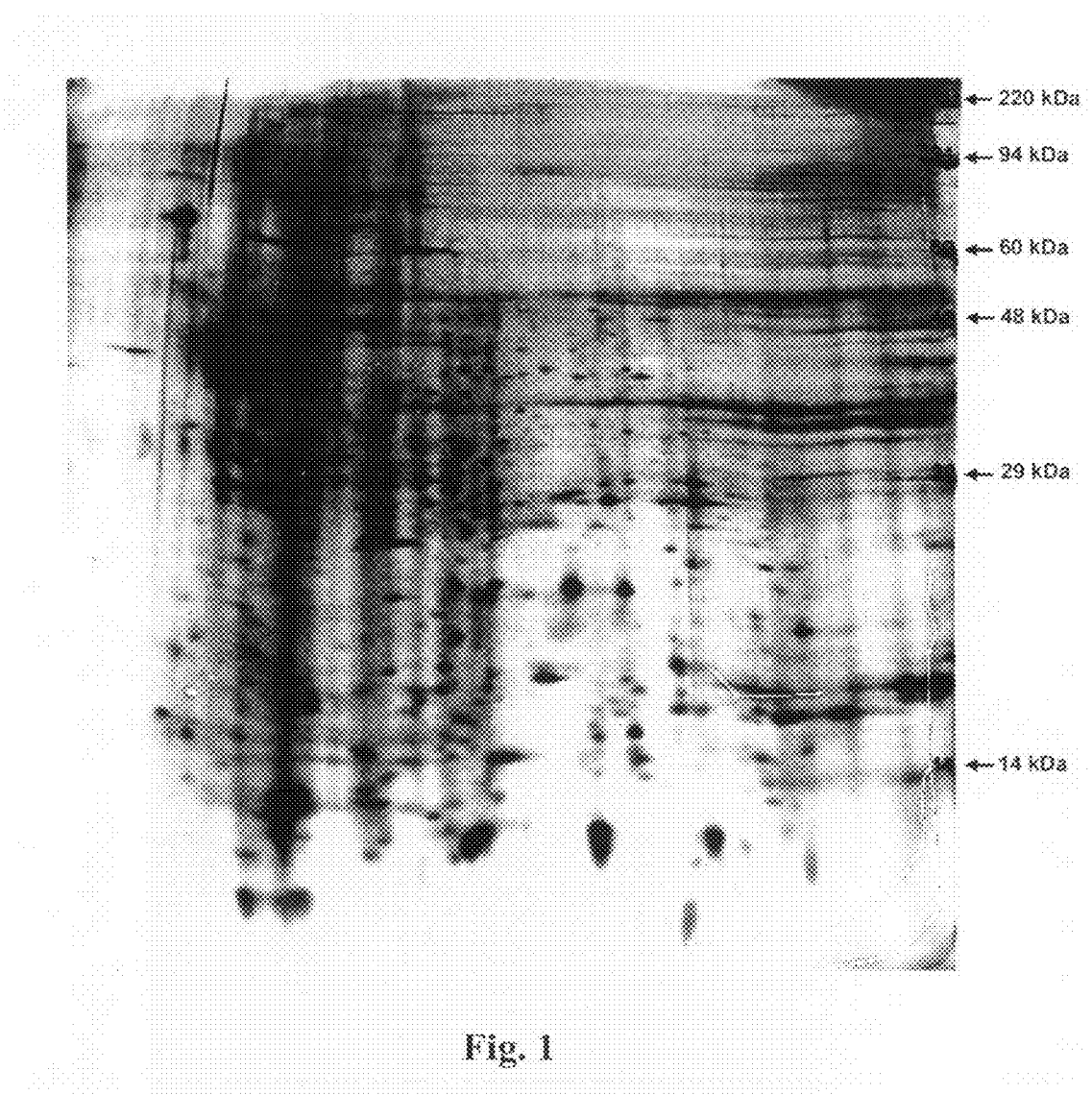
FIG. 1 shows a 2-dimensional SDS PAGE separation (pH 3.5 to 10; 12% polyacrylamide) of proteins secreted by human adult bone marrow-derived somatic cells (ABM-SC at about 27 population doublings). Each spot on the gel represents a separate and distinct protein, ranging in size from approximately 5-200 kilodaltons (kDa). The X-axis shows proteins separated according to isoelectric point (pH 3.5 to 10). The Y-axis shows proteins separated according to molecular weight (via passage through 12% polyacrylamide).

Typically, a stem cell or other early-stage progenitor cells lose plasticity because the cells have committed to a particular differentiation pathway. At the biomolecular level, as this process begins to occur the cell loses the ability to respond to certain signaling molecules (e.g., mitogens and morphogens) which would otherwise drive the cell to divide or become another cell type. Thus, as a cell begins to differentiate, it leaves the cell cycle (i.e., can no longer go through mitosis) and enters an irreversible state called G0 wherein the cell can no longer divide. Entry into G0 is also associated with replicative senescence (hallmarks of which include increased expression of intracellular proteins p21 and p53). Thus, loss of plasticity (the ability to differentiate into a variety of cell types) is typically considered a prelude to cellular differentiation or cellular senescence. Furthermore, loss of plasticity is also typically associated with the loss of a cells capacity for continued self-renewal. In contrast, to this typical and traditionally accepted scenario, an unexpected and surprising result of the present invention is that the exCF-SC of the present invention (e.g., exABM-SC) continue to self-renew (including self-renewal at a relatively constant rate) despite loss of plasticity. Accordingly, one embodiment of the present invention are therapeutically useful "end-stage cells" with a continued capacity for self-renewal (e.g., cells capable of continued self-renewal and production of trophic support factors (or "trophic support cells")). In another embodiment, the exCF-SC and exABM-SC of the present invention do not express significant quantities of p21 and/or p53, wherein a "significant quantity" of said molecules is a quantity which is indicative of cell senescence (wherein senescence may require sufficient expression levels of p21, p53, and/or other cell cycle regulators).

Additionally, most experts in the field of the present invention would expect a non-hematopoietic stromal-type cell that has lost plasticity to have limited utility or capability of generating or promoting regeneration of organs and tissues. Thus, another surprising and unexpected result of the present invention, is the ability to generate extensively passaged CF-SC (e.g., ABM-SC) which have lost plasticity yet retain the ability to generate new tissue in vitro and to promote regeneration of tissue in vivo.

The present invention is drawn, inter alia, to methods of repairing, regenerating, and/or rejuvenating tissues using self-renewing cells, referred to herein as colony-forming somatic cells (CF-SC) (an example of which are adult human bone marrow-derived somatic cells (ABM-SC)). Self-renewing colony-forming somatic cells (CF-SC) such as adult human bone marrow-derived somatic cells (ABM-SC) as used in the present invention are prepared as described in U.S. Patent Publication No. 20030059414 (U.S. application Ser. No. 09/260,244, filed Sep. 21, 2001) and U.S. Patent Publication No. 20040058412 (U.S. application Ser. No. 10/251,685, filed Sep. 20, 2002). Each of these patent applications are hereby incorporated by reference in their entirety. Also incorporated by reference herein are U.S. Provisional Patent Applications 60/929,151 and 60/929,152 (each filed on Jun. 15, 2007), U.S. Provisional Patent Application 60/955,204 (filed on Aug. 10, 2007), and U.S. Provisional Patent Application 60/996,093 (filed on Nov. 1, 2007).

In particular, CF-SC isolated from a source population of cells (such as, for example, from bone marrow (ABM-SC and exABM-SC), fat, skin, placenta, muscle, umbilical cord blood, or connective tissue), are permitted to adhere to a cell culture surface in the presence of an appropriate media (such as for example, but not limited to, Minimal Essential Medium-Alpha (e.g., available from HYCLONE™) supplemented with 4 mM glutamine and 10% fetal bovine serum) and cultured under low oxygen conditions (such as for example, but not limited to, $O_2$ at about 2-5%, $CO_2$ at about 5%, balanced with nitrogen) and subsequently passaged at low cell densities (such as at about 30-1000 cells/cm$^2$) such that the CF-SC maintain an essentially constant population doubling rate (such as for example, but not limited to, a doubling rate of less than about 30 hours) through numerous population doublings (such as for example, but not limited to, going through 10, 15, 20, 25, 30, 35, 40, 45 and/or 50 population doublings).

Embodiments of the invention may be generated with CF-SC and exCF-SC (for example, ABM-SC and exABM-SC) cultured under low oxygen conditions wherein said $O_2$ concentrations range from about 1-20% (for example, wherein the $O_2$ concentration is about 1%, 2%, 3%, 4%, 5%, 6%, 7%, 8%, 9%, 10%, 11%, 12%, 13%, 14%, 15%, or 20%), plus $CO_2$ and balanced with nitrogen. For example, ABM-SC may be cultured under low oxygen conditions wherein said $O_2$ concentrations are about 20%, less than about 20%, about 15%, less than about 15%, about 10%, less than about 10%, about 7%, less than about 7%, about 6%, less than about 6%, about 5%, less than about 5%, about 4%, less than about 4%, about 3%, less than about 3%, about 2%, less than about 2%, about 1%; or, wherein said low oxygen conditions are in a range from about 1% to about 20%, about 1% to about 15%, about 1% to about 10%, about 1% to about 5%, about 5% to about 20%, about 5% to about 15%, about 5% to about 10%, about 10% to about 15%, about 10% to about 20%, about 2% to about 8%, about 2% to about 7%, about 2% to about 6%, about 2% to about 5%, about 2% to about 4%, about 2% to about 3%, about 3% to about 8%, about 3% to about 7%, about 3% to about 6%, about 3% to about 5%, about 3% to about 4%, about 4% to about 8%, about 4% to about 7%, about 4% to about 6%, about 4% to about 5%, about 5% to about 8%, about 5% to about 7%, about 5% to about 6%, or about 5%.

Embodiments of the invention may be generated with CF-SC and exCF-SC (for example, ABM-SC and exABM-SC) cultured under low oxygen conditions wherein $CO_2$ concentration range from about 1-15% (for example, wherein the $CO_2$ concentration is about 1%, 2%, 3%, 4%, 5%, 6%, 7%, 8%, 9%, 10%, 11%, 12%, 13%, 14%, or 15%), plus low $O_2$ and balanced with nitrogen. Embodiments of the invention may be generated with CF-SC and exCF-SC (for example, ABM-SC and exABM-SC) passaged by seeding cells at low cell densities, wherein said cell density ranges from about 1-2500 cells/$cm^2$ (for example, wherein the cell density is about 1, 2, 5, 10, 20, 30, 40, 50, 60, 70, 80, 90, 100, 200, 300, 400, 500, 600, 700, 800, 900, 1000, 1500, 2000 or 2500 cells/$cm^2$). For example, ABM-SC may be passaged at seeding densities of less than about 2500 cell/$cm^2$, less than about 1000 cells/$cm^2$, less than about 500 cells/$cm^2$, less than about 100 cells/$cm^2$, less than about 50 cells/$cm^2$, less than about 30 cells/$cm^2$, or less than about 10 cells/$cm^2$. Embodiments of the invention may be generated with CF-SC and exCF-SC (for example, ABM-SC and exABM-SC) wherein the cell population doubling rates are maintained in a range of less than about 24-96 hours (for example, wherein the cell population doubling rate is maintained at less than about 24, 30, 36, 42, 48, 54, 60, 66, 72, 78, 84, 90, or 96 hours). Embodiments of the invention may be generated with CF-SC and exCF-SC (for example, ABM-SC and exABM-SC) wherein the cell population maintains an essentially constant doubling rate through a range of population doublings such as in a range of about 5-50 population doublings (for example, wherein the population doubling rate is maintained for about 5-10, 5-15, 5-20, 5-25, 5-30, 5-35, 5-40, 5-45, or 5-50 population doublings).

Embodiments of the invention include use of CF-SC and exCF-SC (for example, ABM-SC and exABM-SC) incorporated into pharmaceutically acceptable compositions which may be in a liquid, semi-solid, or solid-like state. Use of the terms "liquid, semi-solid, or solid-like state" is intended to indicate that the pharmaceutically acceptable composition in which the cells are contained can span a range of physical states from 1) a common liquid state (such as in an ordinary physiological saline solution); 2) to a wide-range of low-to-highly viscous states including jelly-like, gelatinous, or viscoelastic states (wherein the pharmaceutical composition contains from very high to very low levels of extracellular water, for example, such that the composition ranges in viscosity from a state where it "oozes" slowly like oil or honey to increasingly gelatinous or viscoelastic states which may be jelly-like, pliable, semi-elastic and/or malleable; 3) to a solid-like state (having very low levels of extracellular water) wherein the living cells within the matrix have remodeled the milieu in which they were initially suspended into a durable, non-gelatinous, but still pliable, semi-elastic, and malleable matrix (which, for example, has some of the same pliable, semi-elastic properties of mammalian skin); see, FIGS. 10A and 10B.

(Note: Viscoelasticity, also known as anelasticity, describes materials that exhibit both viscous and elastic characteristics when undergoing plastic deformation. Viscous materials, like honey, resist shear flow and strain linearly with time when a stress is applied. Elastic materials strain instantaneously when stretched and just as quickly return to their original state once the stress is removed. Viscoelastic materials have elements of both of these properties and, as such, exhibit time dependent strain.)

Clinical administration of cells in liquid, semi-solid, and solid-like vehicles will enable application of treatments that shape to the contour of the wound bed, without trapping unwanted exudate in the wound.

Combining soluble matrix components such as collagens or fibrin with CF-SC and exCF-SC (for example, ABM-SC and exABM-SC) induces the cell population to up-regulate expression of important secreted proteins such as cytokines and matrix metalloproteinases. Moreover, application of ABM-SC to surgically-induced wounds appears to facilitate wound closure and prevent scarring thereby resulting in minimal scarring (see, Example 7).

Additionally, the apparent immunomodulatory properties of CF-SC and exCF-SC (such as, ABM-SC and exABM-SC) (see e.g., Example 4) make compositions and therapies incorporating these cells attractive for the treatment of immunological disorders and diseases involving the skin, such as for example, but not limited to, chronic inflammatory dermatoses, psoriasis, lichen planus, lupus erythematosus (LE), graft-versus-host disease (GVHD), and drug eruptions (i.e., adverse cutaneous drug reactions).

Secreted proteins and cell-supernatant fractions from CF-SC and exCF-SC (such as, ABM-SC and exABM-SC) conditioned media can be manufactured from serum-free conditions, concentrated and prepared in such manner as to make them suitable for in vivo use. When prepared this way, conditioned serum-free media from ABM-SC has been demonstrated to contain numerous pro-regenerative cytokines, growth factors, and matrix proteases in therapeutically effective concentrations (see, Table 1A, 1B and 1C). The complex mixture of hundreds of soluble factors produced by ABM-SC can be distinguished by 2D SDS PAGE (see, FIG. 1). Individual proteins and other macromolecules can be excised from these gels and identified using techniques routinely practiced in the art, such as, for example, MALDI-TOF mass spectrometry (Matrix Assisted Laser Desorption Ionisation-Time Of Flight spectrometry).

Utilizing the methods disclosed (as well as other separation techniques such as chromatography or hollow fiber cell culture systems), the desired proteins or cell supernatant fractions can be isolated, dialyzed, lyophilized and stored as a solid, or reconstituted in an appropriate vehicle for therapeutic administration. In one embodiment, the proteins or cell-supernatant fractions would be reconstituted in a semi-solid collagen or fibrin-based vehicle, and applied topically to the wound bed.

In addition to products generated by CF-SC and exCF-SC (such as, ABM-SC and exABM-SC), any number and type of pharmaceutically acceptable small molecules to large macromolecular compounds (including biologics such as lipids, proteins, and nucleic acids) may be incorporated for administration with a pharmaceutically acceptable carrier such as biodegradable matrices in which CF-SC and exCF-SC (such as, ABM-SC and exABM-SC), or products generated by such cells, are contained. As a very small sampling, such additional molecules may include small molecule pharmaceuticals such as anti-inflammatories, antibiotics, vitamins, and minerals (such as calcium) to name but a few categories. Likewise, a very small sampling of biologics may include extracellular matrix proteins, blood plasma coagulation proteins, antibodies, growth factors, chemokines, cytokines, lipids (such as cardiolipin and sphingomyelin), and nucleic acids (such as ribozymes, anti-sense oligonucleotides, or cDNA expression constructs); including therapeutically beneficial variants and derivatives of such molecules such as various isoforms, fragments, and subunits, as well as substitution, insertion, and deletion variants. These are mentioned merely by way of example, as it can be appreciated by those skilled in the art that, in combination with the teachings provided herein, any number of additional structural or therapeutically beneficial compounds could be included for administration with a pharmaceutically acceptable carrier such as biodegradable matrices in which CF-SC and exCF-SC (such as, ABM-SC and exABM-SC), or products generated by such cells, are contained.

One embodiment of the invention encompasses a method of stimulating wound closure in a diabetic patient, such as a diabetic foot or venous leg ulcer, or a post-surgical wound. Stimulation of wound closure may be promoted by treatment with a pharmaceutical composition of CF-SC and exCF-SC (such as, ABM-SC and exABM-SC), or products generated by such cells, combined with naturally occurring extracellular matrix and/or blood plasma proteins components such as, for example, purified natural or recombinant human, bovine, porcine, or recombinant collagens, laminins, fibrinogen, and/or thrombin. The pharmaceutical composition may be administered to a mammal, including a human, at the site of tissue damage. In another embodiment, a topically administered biodegradable matrix is formed from a mixture of components such as purified natural or recombinant collagen, fibrinogen, and/or thrombin, combined with allogeneic CF-SC and exCF-SC (such as, ABM-SC and exABM-SC).

In another embodiment of the invention, a pharmaceutical composition of allogeneic cells and matrix are cultured in vitro for an extended period of time (such as, for example, but not limited to 1 day to one month or longer), producing the de novo formation of connective tissue. In another embodiment of the invention, the biodegradable matrix is bovine collagen or polyglycolic acid. In another embodiment, the pharmaceutical composition is cultured in serum-free cell media under conditions of reduced oxygen tension, for example but not limited to, oxygen tension equivalent to about 4-5% $O_2$, 5% $CO_2$, and balanced with nitrogen.

In one embodiment, the invention encompasses a method of preparing a pharmaceutical composition comprising the steps:

(a) preparing a solution comprising soluble collagen, serum-free cell culture media supplemented with glutamine, sodium biocarbonate, and HEPES (optionally including supplementation with insulin, transferrin, and/or selenium);

(b) re-suspending CF-SC or exCF-SC (for example, ABM-SC or exABM-SC) in the solution; and, (c) transferring the cell suspension to a tissue mold, or equivalent thereof, to congeal at 37° C., for example, when placed in a cell culture incubator.

The above method of preparing a pharmaceutical composition may additionally comprise the step of incubating the culture for an extended period of time (such as, for example but not limited to, 1-3 days or longer) under low oxygen tension conditions equivalent to about 4-5% $O_2$, 5% $CO_2$, and balanced with nitrogen.

In another embodiment, the invention encompasses a method of preparing a pharmaceutical composition comprising the steps of:

a) preparing a solution comprising fibrinogen and thrombin;

b) re-suspending CF-SC or exCF-SC (for example, ABM-SC or exABM-SC) in the solution; and, c) administering the re-suspended solution to an open wound.

In another embodiment, the invention encompasses a method of preparing a pharmaceutical composition comprising the steps of:

a) preparing a solution comprising soluble collagen, serum-free cell culture media supplemented with glutamine, sodium biocarbonate, and HEPES (optionally including supplementation with insulin, transferrin, and/or selenium); and b) mixing a fraction or fractions of cell-supernatant derived from CF-SC or exCF-SC (for example, ABM-SC or exABM-SC) into the solution; and, c) transferring the solution to a tissue mold, or equivalent thereof, to congeal at 37° C., for example, when placed in a cell culture incubator.

The above method of preparing a pharmaceutical composition may additionally comprise the step of incubating the tissue mold, or equivalent thereof, under atmospheric oxygen tension conditions equivalent to about 18-21% $O_2$ and 5% $CO_2$.

In another embodiment, the invention encompasses a method of preparing a pharmaceutical composition comprising the steps of:

d) preparing a solution comprising fibrinogen and thrombin;

e) mixing a fraction or fractions of cell-supernatant derived from CF-SC or exCF-SC (for example, ABM-SC or exABM-SC) into the solution; and, f) administering the solution to an open wound.

In another embodiment, the present invention encompasses tissue regeneration, particularly in the treatment of tissue damage caused by: immune related disorders (such as autoimmune disorders); inflammation (including both acute and chronic inflammatory disorders); ischemia (such as myocardial infarction); traumatic injury (such as burns, lacerations, and abrasions); infection (such as bacterial, viral, and fungal infections); and, chronic cutaneous wounds. The present invention encompasses treatment of a diversity of damage and disorders, for example, but not limited to, neurological damage and disorders of the central nervous system (brain) and peripheral nervous system (e.g., spinal cord) (for example, such as may be caused by neurotrauma and neurodegenerative diseases). Another embodiment of the invention encompasses treatment of diseases and disorders requiring bone, connective tissue, and cartilage regeneration, chronic and acute inflammatory liver diseases, vascular insufficiency, and corneal and macular degeneration. Another embodiment of the invention encompasses treating cardiovascular and pulmonary damage and disorders (for example, such as myocardial ischemia and repair and regeneration of blood vessels). Another embodiment of the invention encompasses treating damage and disorders of pancreatic and hepatic tissue as well as other endocrine and exocrine glands. Another embodiment of the invention encompasses treating damage and disorders of thymus as well as other immune cell producing and harboring organs. Another embodiment of the invention encompasses treating damage and disorders of the genitourinary system (for example, such as the ureter and bladder). Another embodiment of the invention encompasses treating hernias and herniated tissues. Another embodiment of the invention encompasses treatment, repair, regeneration, and reconstruction of heart valves.

CF-SC and exCF-SC (such as, ABM-SC and exABM-SC) or protein and cell-supernatant fractions derived from CF-SC and exCF-SC (such as, ABM-SC and exABM-SC), can also be reconstituted in a solid-like collagen-base device. When the cells are reconstituted in such manner, the solid-like collagen matrix is remodeled over several days, giving rise to a neotissue that has fabricated its own unique matrix. Such CF-SC and exCF-SC (such as, ABM-SC and exABM-SC) derived neotissues are pliable, suturable, and bioactive (see e.g., FIGS. 6, 7, and 10A-C). These structures could also be sterilized, chemically cross-linked, freeze-dried, or further processed, rendering the cells non-viable and incapable of further growth.

Such devices may be particularly beneficial in the treatment of burns, including full thickness burn wounds. To rebuild a vascularized wound bed, patients with severe burns are often treated with an artificial dermal replacement after surgical resection of the dead tissue. After the wound bed has healed, these patients are subsequently treated with artificial skin products or applications of epithelial cells in an attempt to re-grow host epidermis.

Compositions, such as described herein, when used in lieu of a conventional artificial dermal products (e.g., DERMA-GRAFT™), may increase the longevity of subsequently grafted allogeneic skin, by inhibiting or reducing undesirable T-cell mediated immune reactions (see, Example 5). By modulating T-cell mediated immune responses, compositions of the present invention may permit subsequent reapplication of the artificial skin for a durations adequate to stimulate re-growth of the patients own skin.

The above-referenced ABM-SC have been shown to exhibit the following properties:

In vitro
  Secretion of cytokines important in angiogenesis and tissue repair.
  Release of factors for prevention and inhibition of scarring and matrix turnover.
  Promotion of migration of endothelial cells indicative of pro-angiogenic activity.
In Vivo
  Significant improvement in outcomes in multiple animal models of acute myocardial infarction (AMI) and stroke.
  Effective and well-tolerated intracardiac or intracerebral delivery of cells.
  Cells not detectable in tissues eight weeks post-injection.
  No measurable immune response against cells.

Figure 11:
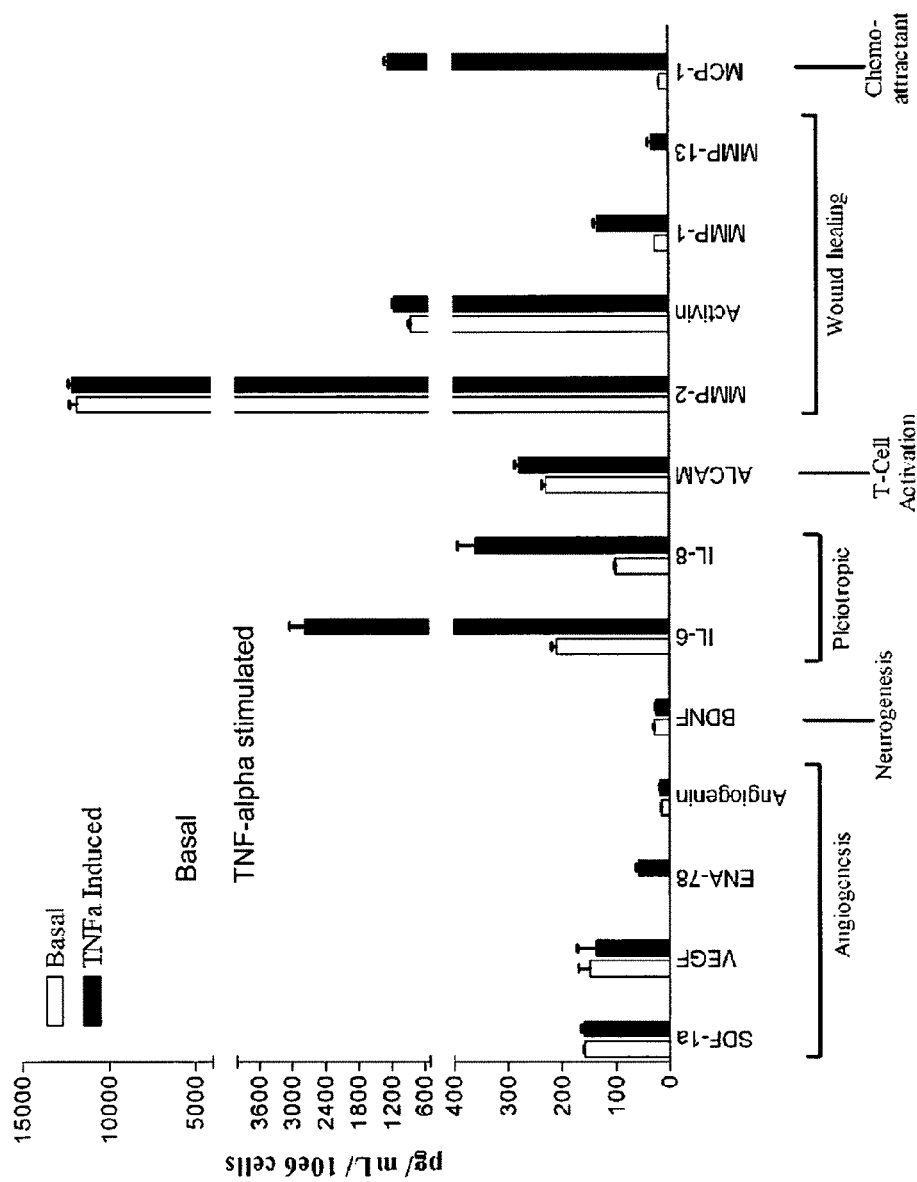
FIG. 11 shows an example of the quantities of multiple pro-regenerative cytokines secreted by human ABM-SC with and without TNF-alpha stimulation. When sub-cultured, ABM-SC secrete potentially therapeutic concentrations of several growth factors and cytokines known to augment angiogenesis, inflammation and wound healing. ABM-SC have been shown to consistently secrete several cytokines and growth factors in vitro; including proangiogenic factors (e.g., SDF-1 alpha, VEGF, ENA-78 and angiogenin), immunomodulators (e.g., IL-6 and IL-8) and scar inhibitors/wound healing modulators (e.g., MMP-1, MMP-2, MMP-13 and Activin-A). Furthermore, the release of several of these factors is modulated by tumor necrosis factor alpha (TNF-alpha), a known inflammatory cytokine released during the course of acute tissue injury.

In one embodiment of the invention, a number of pro-regenerative cellular factors secreted by CF-SC and exCF-SC (such as, ABM-SC and exABM-SC) may be used in treatment, repair, regeneration, and/or rejuvenation of damaged tissues and organs (such as, for example, cardiac and neuronal organs and tissues damaged by, for example, heart failure due to acute myocardial infarction (AMI) or stroke). These include factors which can be secreted by CF-SC such as ABM-SC as shown in FIG. 11. For example, these factors include, but are not limited to, SDF-1alpha, VEGF, ENA-78, Angiogenin, BDNF, IL-6, IL-8, ALCAM, MMP-2, Activin, MMP-1, MMP-13, MCP-1. See, FIG. 11. Additional factors, such as those listed in Table 1A, 1B and 1C, may also be secreted by CF-SC and exCF-SC (such as, ABM-SC and exABM-SC). See e.g., Table 1A, 1B and 1C.

Secretion of pro-regenerative factors by CF-SC and exCF-SC (such as, ABM-SC and exABM-SC) may be enhanced or induced by pre-treatment with stimulatory factors (such as, for example, tumor necrosis factor-alpha (TNF-alpha)) to induce the production of conditioned cell culture media or to prime the cells before administration of cells to a patient.

Figure 12:
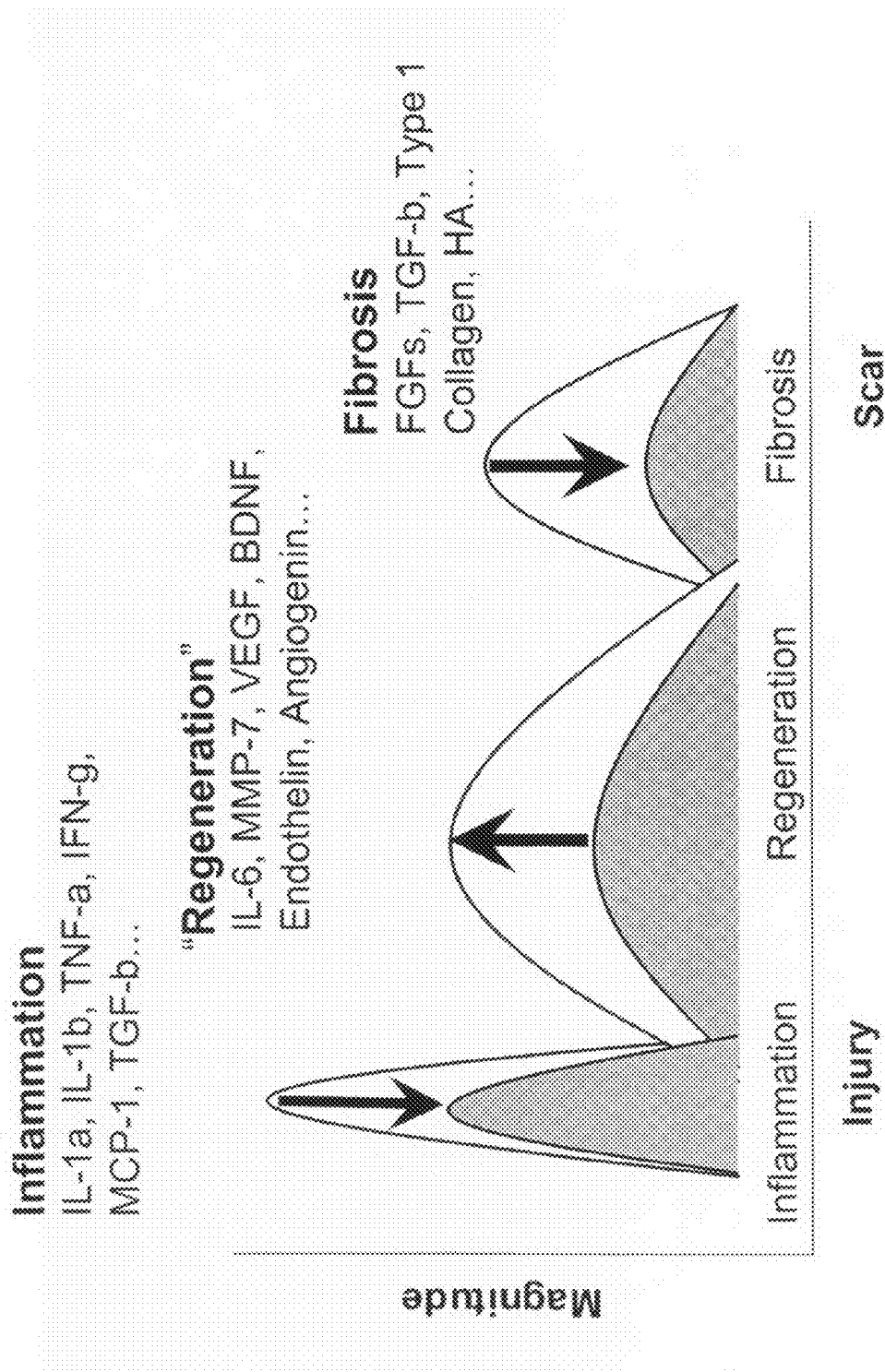
FIG. 12 shows a model injury-response cascade (inflammation, regeneration, and fibrosis from injury through scar) and examples of molecules that can play roles in inflammation, regeneration, and fibrosis.

Acute ischemia, trauma or inflammation lead to a constellation of cellular and chemical events in the affected organs and tissues. See e.g., FIG. 12. In the inflammation phase there occurs a release of factors and an influx of cells to the injured site. In the regeneration phase there occurs a recruitment of circulating cells for the proper repair of functional tissue. And, in the fibrosis phase, there occurs a deposition of fibrotic scars which potentially compromise organ function. Moreover, a variety of cytokines and other biological molecules play a diversity of roles in each of these processes. See e.g., FIG. 12.

Use of CF-SC and exCF-SC (such as, ABM-SC and exABM-SC) in the present invention includes methods of treating and preventing inflammation, methods of stimulating organ and tissue regeneration while reducing fibrosis (i.e., tissue scarring), and methods of stimulating angiogenesis via compositions (e.g., cytokines, proteases, extracellular matrix proteins, etc) produced by stimulated or unstimulated CF-SC and exCF-SC (such as, ABM-SC and exABM-SC).

In another embodiment, CF-SC and exCF-SC may inhibit the biological process of fibrosis. Fibrosis is a natural byproduct of wound healing, scarring, and inflammation in many human tissues. Fibrosis, also known as fibrotic scarring, is a significant impediment to regenerating tissue with optimal function, especially in the heart and central nervous system (CNS), because scar tissue displaces cells needed for optimal organ function. Treatment with cells disclosed herein helps to prevent or reduce fibrosis and thereby facilitates the healing of damaged tissue. The fibrosis may be prevented by additive or synergistic effects of two or more secreted proteins or cell produced compositions, including membrane bound cell-surface molecules. Additionally matrix proteases induced or produced by the administered CF-SC and exCF-SC (such as, ABM-SC and exABM-SC) may play an important part in preventing fibrosis.

In another exemplary use of the present invention, angiogenesis, also known as neovascularization, is increased in a desired tissue. Angiogenesis, or the formation of new blood vessels, is a key component of regenerative medicine because newly formed tissue must have a blood supply, and angiogenesis is crucial if endothelial cells are lost during degenerative processes, disease progression, or acute injuries for which the present invention is a treatment. Hence, use of CF-SC and exCF-SC (for example, ABM-SC and exABM-SC) or compositions produced by such cells are useful in stimulating angiogenesis in target tissues and organs (especially, for example, in damaged cardiac tissue). Angiogenesis is an important component of tissue repair and can operate in conjunction with fibrosis inhibition to optimize healing of damaged tissues.

Another exemplary use of the present invention involves the stimulation of regeneration or rejuvenation processes without the engraftment of the administered cells. In vivo studies have shown that long term cell engraftment or tissue-specific differentiation of human ABM-SC or exABM-SC are generally not seen, suggesting that the mechanism by which these cells incite tissue regeneration is not through cell replacement, but instead through a host response to the cells themselves and/or factors they produce. This is not surprising, however, given that the role of ABM-SC in bone marrow is to provide structural and trophic support. Hence, the present invention includes treatment of damaged tissues and organs wherein the administered CF-SC and exCF-SC (for example, ABM-SC and exABM-SC) do not exhibit permanent or long-term tissue or organ engraftment. Instead, the therapeutic CF-SC and exCF-SC (for example, ABM-SC and exABM-SC) provide trophic support factors, suppress cell-death, inhibit fibrosis, inhibit inflammation (e.g., immune cell inflammatory responses), promote extra-cellular matrix remodeling, and/or stimulate angiogenesis without becoming part of the repaired tissue at a significant or currently detectable level.

A further example of the present invention teaches that after a period of time, the administered cells are not detected anywhere in the experimental animal, suggesting the administered cells are completely cleared from the body. This suggests that secreted factors play an essential role in the repair of damaged tissue.

In yet another example of the present invention illustrating its utility, the hABM-SCs disclosed herein come from one donor source. As such, these cells will be allogeneic cell transplants in patients which might suggest that these transplanted cells could potentially stimulate an adverse immune response. However, surprisingly, we find that transplanted allogeneic cells disclosed herein actually can suppress mitogen induced T-cell proliferation in vitro and avoid induction of a T-cell-dependent immune response in vivo. A T-cell mediated immune response is a key factor in immune processes that are detrimental to healing, regenerative, and rejuvenation processes.

As used herein "an effective amount" is an amount sufficient to produce detectable improvement in tissue, organ, or biological system (e.g., immune system) performance, function, integrity, structure, or composition wherein said improvement is indicative of complete or partial amelioration, restoration, repair, regeneration, or healing of the damaged tissue, organ or biological system.

Table 1A, 1B and 1C shows an extensive list of cytokines, growth factors, soluble receptors, and matrix proteases secreted by human ABM-SC when sub-cultured in serum-free cell culture media. Media Supernatant Concentrate #1=Advanced DMEM (Gibco™) supplemented with 4 mM L-glutamine. Media Supernatant Concentrate #2=RPMI-1640 containing 4 mM L-glutamine and HEPES (HyClone) supplemented with Insulin-Transferrin-Selenium-A (Gibco™).

The results demonstrate that numerous trophic factors and soluble receptors important for tissue regeneration and modulation of the immune system are produced by ABM-SC at therapeutically relevant levels when cultured under these conditions. Notably, earlier experiments demonstrated that supplementation of the base culture medium with insulin, transferrin, and selenium was required to achieve secreted protein levels such as those indicated in Table 1A, 1B and 1C.

Immune Disorders

Cells and compositions of the present invention may be used to prevent, treat, and/or ameliorate, inter alia, immune, autoimmune, and inflammatory diseases and disorders. Some examples of such disorders are indicated below; these lists are exemplary only and are not intended to be comprehensive with respect to all immune, autoimmune, and inflammatory diseases and disorders; nor should the following be construed as limiting with respect to pathologies which may be treated with the cells and compositions of the present invention.

Example of some diseases with a complete or partial autoimmune etiology: Acute disseminated encephalomyelitis (ADEM), Addison's disease, Ankylosing spondylitis, Antiphospholipid antibody syndrome (APS), Aplastic anemia, Autoimmune hepatitis, Autoimmune Oophoritis, Celiac disease, Crohn's disease, Diabetes mellitus type 1, Gestational pemphigoid, Goodpasture's syndrome, Graves' disease, Guillain-Barré syndrome (GBS), Hashimoto's disease, Idiopathic thrombocytopenic purpura, Kawasaki's Disease, Lupus erythematosus, Multiple sclerosis, Myasthenia gravis, Opsoclonus myoclonus syndrome (OMS), Optic neuritis, Ord's thyroiditis, Pemphigus, Pernicious anaemia, Polyarthritis, Primary biliary cirrhosis, Rheumatoid arthritis, Reiter's syndrome, Sjögren's syndrome, Takayasu's arteritis, Temporal arteritis (also known as "giant cell arteritis"), Warm autoimmune hemolytic anemia, and Wegener's granulomatosis.

Examples of some diseases suspected of being linked to autoimmunity: Alopecia universalis, Behcet's disease, Chagas' disease, Chronic fatigue syndrome, Dysautonomia, Endometriosis, Hidradenitis suppurativa, Interstitial cystitis, Lyme disease, Morphea, Neuromyotonia, Narcolepsy, Psoriasis, Sarcoidosis, Scleroderma, Ulcerative colitis, Vitiligo, and Vulvodynia.

Examples of some immune hypersensitivity diseases and disorders: Allergic asthma, Allergic conjunctivitis, Allergic rhinitis ("hay fever"), Anaphylaxis, Myasthenia gravis, Angioedema, Arthus reaction, Atopic dermatitis (eczema), Autoimmune hemolytic anemia, Autoimmune Pernicious anemia, Coeliac disease, Contact dermatitis (poison ivy rash, Eosinophilia, Erythroblastosis Fetalis, Farmer's Lung (Arthus-type reaction), for example), Goodpasture's syndrome, Graves' disease, Graves' disease, Hashimoto's thyroiditis, Hemolytic disease of the newborn, Immune complex glomerulonephritis, Immune thrombocytopenia, Myasthenia gravis, Pemphigus, Rheumatic fever, Rheumatoid arthritis, Serum sickness, Subacute bacterial endocarditis, Symptoms of leprosy, Symptoms of malaria, Symptoms of tuberculosis, Systemic lupus erythematosus, Temporal arteritis, Transfusion reactions, Transplant rejection, and Urticaria (hives).

Example of some inflammatory disorders: allergies, ankylosing spondylitis, arthritis, asthma, autistic enterocolitis, autoimmune diseases, Behcet's disease, chronic inflammation, glomerulonephritis, inflammatory bowel disease (IBD), inflammatory bowel diseases, pelvic inflammatory disease, psoriasis, psoriatic arthritis, reperfusion injury, rheumatoid arthritis, transplant rejection, and vasculitis.

Example of some immunodeficiency disorders: B cell deficiencies (such as X-linked agammaglobulinemia and Selective Immunoglobulin Deficiency), T cell deficiencies (such as DiGeorge's syndrome (Thymic aplasia), Chronic mucocutaneous candidiasis, Hyper-IgM syndrome and, Interleukin-12 receptor deficiency), Combined T cell and B cell abnormalities (such as Severe Combined Immunodeficiency Disease (SCID), Wiskott-Aldrich syndrome, and Ataxia-telangiectasia), Complement Deficiencies (such as Hereditary Angioedema or Hereditary angioneurotic edema and Paroxysmal nocturnal hemoglobinuria), Phagocyte deficiencies (such as Leukocyte adhesion deficiency, Chronic Granulomatous Disease (CGD), Chediak-Higashi syndrome, Job's syndrome (Hyper-IgE syndrome), Cyclic neutropenia, Myeloperoxidase deficiency, Glucose-6-phosphate dehydrogenase deficiency, and Interferon-γ deficiency), and Common Variable Immunodeficiency (CVID), Vici syndrome, and Acquired immune deficiency syndrome (AIDS).

EMBODIMENTS OF THE INVENTION

Particular embodiments of the invention include the following:

A1. A method of administering a therapeutically useful amount of a biological composition or compositions to a subject, comprising administering to said subject an isolated population of self-renewing colony forming cells, wherein the cells in said cell population have substantially no multipotent differentiation capacity, wherein said cells have a normal karyotype, and wherein said cells are non-immortalized.

A2. A method of administering a therapeutically useful amount of a biological composition or compositions to a subject, comprising:

(i) isolating the biological composition or compositions produced by an isolated population of self-renewing colony forming cells; and, (ii) administering said biological composition or compositions to said subject, wherein the cells in said cell population have substantially no multipotent differentiation capacity, wherein said cells have a normal karyotype, and wherein said cells are non-immortalized.

A3. A method of repairing, treating, or promoting regeneration of damaged tissue in a subject, comprising administering to said subject an effective amount of an isolated population of self-renewing colony forming cells, wherein the cells in said cell population have substantially no multipotent differentiation capacity, wherein said cells have a normal karyotype, and wherein said cells are non-immortalized.

A4. A method of repairing, treating, or promoting regeneration of damaged tissue in a subject, comprising:

(i) isolating the biological composition or compositions produced by an isolated population of self-renewing colony forming cells; and, (ii) administering said biological composition or compositions to said subject, wherein the cells in said cell population have substantially no multipotent differentiation capacity, wherein said cells have a normal karyotype, and wherein said cells are non-immortalized.

A5. A method of treating or reducing inflammation, immune, or autoimmune activity in a subject, comprising administering to said subject an effective amount of an isolated population of self-renewing colony forming cells, wherein the cells in said cell population have substantially no multipotent differentiation capacity, wherein said cells have a normal karyotype, and wherein said cells are non-immortalized.

A6. A method of treating or reducing inflammation, immune, or autoimmune activity in a subject, comprising:

(i) isolating the biological composition or compositions produced by an isolated population of self-renewing colony forming cells; and, (ii) administering said biological composition or compositions to said subject, wherein the cells in said cell population have substantially no multipotent differentiation capacity, wherein said cells have a normal karyotype, and wherein said cells are non-immortalized.

A7. The method of any of embodiments A1 to A6, wherein prior to administration, said cell population has been passaged in vitro for a number of population doublings sufficient to cause the cells in said population to lose multipotent differentiation capacity.

A8. The method of any one of embodiments A1 to A7, wherein said cell population has unipotent differentiation capacity.

A9. The method of any of embodiments A1 to A8, wherein said cells have substantial capacity for self-renewal.

A10. The method of any of embodiments A1 to A9, wherein prior to administration said cell population has been passaged in vitro for a number of population doublings while retaining substantial capacity for self-renewal.

A11. The method of any one of embodiments A1 to A10, wherein the cells in said isolated cell population are not embryonic stem cells.

A12. The method of any one of embodiments A1 to A11, wherein the cells in said isolated cell population are not stem cells, mesenchymal stem cells, hematopoietic stem cells, multipotent adult progenitor cells (MAPCs), multipotent adult stem cells (MASCs), or fibroblasts.

A13. The method of any one of embodiments A1 to A12, wherein said cells do not differentiate into one or more cell types selected from the group consisting of:

a) osteocytes; b) adipocytes; and, c) chondrocytes.

A14. The method of any one of embodiments A1 to A13, wherein said cells do not deposit detectable levels of calcium following treatment under osteoinductive conditions.

A15. The method of embodiment A14, wherein said osteoinductive conditions include exposure to exogenously supplied Noggin.

A16. The method of any one of embodiments A1 to A15, wherein the cells in said isolated cell population are derived from connective tissue.

A17. The method of any one of embodiments A1 to A16, wherein the cells in said isolated cell population are stromal cells.

A18. The method of any one of embodiments A1 to A17, wherein the cells in said isolated cell population co-express CD49c and CD90.

A19. The method of any one of embodiments A1 to A18, wherein the cell population maintains an approximately constant doubling rate through multiple in vitro cell doublings, A20. The method of any one of embodiments A1 to A19, wherein said cells are negative for detectable expression of one or more antigens selected from the group consisting of:

a) CD10; b) STRO-1; and, c) CD106/VCAM-1.

A21. The method of any one of embodiments A1 to A20, wherein said cells are positive for detectable expression of one or more antigens selected from the group consisting of:

a) CD44; b) HLA Class-1 antigen; and, c) β (beta) 2-Microglobulin,

A22. The method of any one of embodiments A1 to A21, wherein said cells express or secrete detectable quantities of compositions selected from the group consisting of:

a) TNF-RI; b) soluble TNF-RI; c) TNF-RII; d) soluble TNF-RII; e) IL-1R antagonist; and, f) IL-18 binding protein.

A23. The method of any one of embodiments A1 to A21, wherein said cells express or secrete detectable quantities of compositions selected from the group consisting of compositions shown in Table 1A, 1B and 1C.

A24. The method of any one of embodiments A1 to A23, wherein the cells in said isolated cell population are initially isolated from a tissue source selected from the group consisting of:

a) bone marrow; b) adipose tissue/fat; c) skin; d) placental; e) umbilical cord; f) tendon; g) ligament; h) muscle fascia; and, i) other connective tissues.

A25. The method of embodiment A24, wherein said tissue source is human.

A26. The method of any one of embodiments A1 to A25, wherein said cell population maintains an approximately constant doubling rate through a number of in vitro cell doublings selected from the group consisting of:

a) 1 to 5 cell doublings; b) 5 to 10 cell doublings; c) 10 to 20 cell doublings; d) 20 to 30 cell doublings; e) 30 to 40 cell doublings; f) 40 to 50 cell doublings; g) 1 to 50 cell doublings; h) 5 to 50 cell doublings; i) 10 to 50 cell doublings; j) 20 to 50 cell doublings; k) 30 to 50 cell doublings; l) 1 to 10 cell doublings; m) 1 to 20 cell doublings; n) 1 to 30 cell doublings; o) 1 to 40 cell doublings; p) 5 to 20 cell doublings; q) 5 to 30 cell doublings; r) 5 to 40 cell doublings; s) 10 to 30 cell doublings; t) 10 to 40 cell doublings; and, u) 20 to 40 cell doublings.

A27. The method of any one of embodiments A1 to A26, wherein said cell population has undergone a number of population doublings selected from the group consisting of:
  a) at least about 10 population doublings; b) at least about 15 population doublings; c) at least about 20 population doublings; d) at least about 25 population doublings; e) at least about 30 population doublings; f) at least about 35 population doublings; g) at least about 40 population doublings; h) at least about 45 population doublings; and, i) at least about 50 population doublings.

A28. The method of any one of embodiments A1 to A27, wherein said biological composition or compositions are bound in or to the cell surface of said cell populations.

A29. The method of any one of embodiments A1 to A28, wherein said biological composition or compositions are secreted into the extracellular environment of said cell populations.

A30. The method of any one of embodiments A1 to A29, wherein said biological composition or compositions are one or more molecules selected from the group consisting of:
  a) proteins; b) carbohydrates; c) lipids; d) fatty acids; e) fatty acid derivatives; d) gases; and, e) nucleic acids.

A31. The method of embodiment A30, wherein said proteins are selected from the group consisting of:
  a) glycosylated proteins; b) cytokines; c) chemokines; d) lymphokines; e) growth factors; f) trophic factors, g) morphogenetic proteins; and, h) hormones.

A32. The method of embodiment A31, wherein said wherein said biological composition or compositions bind to and inactivate, or reduce, the biological activity of molecules selected from the group consisting of:
  a) fatty acids; b) fatty acid derivatives; c) receptor molecules; d) cytokines; e) chemokines; f) lymphokines; g) growth factors; h) trophic factors, i) morphogenetic proteins; and, j) hormones.

A33. The method of embodiment A32, wherein said biological composition or compositions are soluble receptors that bind cognate ligands selected from the group consisting of:
  a) fatty acids; b) fatty acid derivatives; c) receptor molecules; d) cytokines; e) chemokines; f) lymphokines; g) growth factors; h) trophic factors, i) morphogenetic proteins; and, j) hormones.

A34. The method of any one of embodiments A1 to A33, wherein said cells are induced to increase expression of one or more biological compositions.

A35. The method of any one of embodiments A1 to A33, wherein said cells are induced to express one or more biological compositions.

A36. The method of any one of embodiments A1 to A29, wherein said one or more biological compositions is/are selected from Table 1A, 1B and 1C.

A37. The method of any one of embodiments A1 to A29, wherein said one or more biological compositions is selected from the group consisting of:
  a) TNF-RI; b) soluble TNF-RI; c) TNF-RII; d) soluble TNF-RII; e) IL-1R antagonist; and, f) IL-18 binding protein.

A38. The method of any one of embodiments A1 to A37, wherein the cells in said cell population do not exhibit long-term engraftment in, or with, tissues or organs when administered to a living mammalian organism.

A39. The method of any one of embodiments A1 to A38, wherein the cells in said cell population maintain approximately constant levels of production of one or more therapeutically useful compositions in vivo.

A40. The method of embodiment A39, wherein said levels of production are maintained for a measure of time selected from the group consisting of:
  a) at least about 24 hours; b) at least about 48 hours; c) at least about 72 hours; d) at least about 4 days; e) at least about 5 days; f) at least about 6 days; g) at least about 7 days; h) at least about 2 weeks; i) at least about 3 weeks; j) at least about 4 weeks; k) at least about 1 month; l) at least about 2 months; m) at least about 3 months; n) at least about 6 months; and, o) at least about 1 year.

A41. The method of any one of embodiments A1 to A40, wherein said patient is human.

A42. The method of any one of embodiments A1 to A41, wherein said method is used to treat a disease or disorder selected from the group consisting of:
  a) a neurological disease or disorder; b) a cardiac disease or disorder; c) a skin disease or disorder; d) a skeletal muscle disease or disorder; e) a respiratory disease or disorder; f) a hepatic disease or disorder; g) a renal disease or disorder; h) a genitourinary system disease or disorder; i) a bladder disease or disorder; j) an endocrine disease or disorder; k) a hematopoietic disease or disorder; l) a pancreatic disease or disorder; m) diabetes; n) an ocular disease or disorder; o) a retinal disease or disorder; p) a gastrointestinal disease or disorder; q) a splenic disease or disorder; r) an immunological disease or disorder; s) an autoimmune disease or disorder; t) an inflammatory disease or disorder; u) a hyperproliferative disease or disorder; and, v) cancer.

A43. The method of any one of embodiments A1 to A42, wherein said cells are genetically modified.

A44. The method of embodiment A43, wherein said cells are genetically modified by introduction of a recombinant nucleic acid molecule.

A45. A process for making an isolated cell population in any one of embodiments A1 to A47, wherein said process comprises:
  i) obtaining a source population of cells from an organism; and,
  ii) culturing said source population of cells in vitro.

B1. A composition comprising a pharmaceutically acceptable mixture of self-renewing, colony-forming somatic cells (CF-SC), or conditioned cell culture media derived from such cells, and purified naturally occurring or isolated recombinant extracellular matrix or blood plasma proteins.

B2. The composition of embodiment B1, wherein said CF-SC are derived from bone marrow.

B3. The composition of embodiments B1 or B2, wherein said CF-SC are derived from a human.

B4. The composition of any one of embodiments B1-B3, wherein said CF-SC are derived from an adult mammal, including humans.

B5. The composition of any one of embodiments B1-B4, wherein said CF-SC express one or more secreted proteins shown in Table 1A, 1B and 1C.

B6. The composition of any one of embodiment B1-B5, wherein said extracellular matrix or blood plasma proteins comprise one or more full-length or alternatively processed isoforms, proteolytic fragments, or subunits of molecules selected from the group consisting of:
  a) collagen; b) elastin; c) fibronectin; d) laminin; e) entactin (nidogen); f) hyaluronic acid; g) polyglycolic acid (PGA); h) fibrinogen (Factor I); i) fibrin; j) prothrombin (Factor II); k) thrombin; l) anti-thrombin; m) Tissue factor Co-factor of VIIa (Factor III); n) Protein C; o) Protein S; p) protein Z; q) Protein Z-related protease inhibitor; r) heparin cofactor II; s) Factor V (proaccelerin, labile factor); t) Factor-VII; u) Factor-VII; v)

Factor-IX; w) Factor-X; x) Factor-XI; y) Factor-XII; z) Factor-XIII; aa) von Willebrand factor; ab) prekallikrein; ac) high molecular weight kininogen; ad) plasminogen; ae) plasmin; af) tissue-plasminogen activator; ag) urokinase; ah) plasminogen activator inhibitor-1; and, ai) plasminogen activator inhibitor-2.

B7. The composition of any one of embodiments B1-B6, further comprising purified naturally occurring or isolated recombinant cytokines or chemokines.

B8. The composition of any one of embodiments B1-B7, wherein said extracellular matrix, blood plasma proteins, cytokines, and/or chemokines are derived from humans.

B9. The composition of any one of embodiments B1-B8, wherein said pharmaceutically acceptable mixture forms a semi-solidified or solidified matrix.

B10. A method of treating damaged tissue with the composition of any one of embodiments B1-B8, wherein the composition is a liquid.

B11. The method of embodiment B10, wherein the liquid is applied by injection.

B12. A method of treating damaged tissue with the composition of any one of embodiments 1-9, wherein the composition is applied as a liquid but thereafter forms a semi-solidified or solidified matrix.

B13. The method of embodiments B10-B12 wherein said tissue is damaged as a result of a condition selected from the group consisting of:

a) disease; b) physical trauma; c) ischemia; d) aging; e) burn; f) bacterial infection; g) viral infection; h) fungal infection; and, i) dysregulation of the immune system.

B14. The method of embodiment B13, wherein the damaged tissue is skin.

B15. A method of using the composition of any one of embodiments B1-B9 for facial skin rejuvenation.

B16. A method of using the composition of any one of embodiments B1-B9, wherein said composition inhibits acute inflammation.

C1. A method for treating, repairing, regenerating, or healing a damaged organ or tissue comprising contacting said damaged organ or tissue with an effective amount of self-renewing colony forming somatic cells or compositions produced from such cells so as to effect said treatment, repair, regeneration, or healing of the damaged organ or tissue.

C2. The method of embodiment C1, wherein said damaged organ or tissue is contacted with an effective amount of self-renewing colony forming somatic cells or compositions produced from such cells by means selected from the group consisting of:

a) injection into the damaged organ or tissue; b) application onto the damaged organ or tissue; c) injection proximal to the damaged organ or tissue; d) application proximal to the damaged organ or tissue; and, e) intravenous administration.

C3. The method of embodiments C1 or C2, wherein the cells are derived from bone marrow.

C4. The method of any one of embodiments C1-C3, wherein the cells are human.

C5. The method of any one of embodiments C1-C4, wherein the cells, or compositions produced by said cells, inhibit or reduce adverse immune responses (such as cell-mediated autoimmunity), fibrosis (scarring) and/or adverse tissue remodeling (for example, ventricular remodeling).

C6. The method of any one of embodiments C1-C5, wherein the cells, or compositions produced by said cells, control inflammation and/or inhibit acute inflammation.

C7. The method of any one of embodiments C1-C5, wherein the cells, or compositions produced by said cells, stimulate or enhance angiogenesis.

C8. The method of any one of embodiments C1-C5, wherein said cells do not exhibit significant or detectable levels of permanent or long-term engraftment into said damaged organs or tissues.

C9. The method of any one of embodiments C1-C8, wherein said damaged organs are selected from the group consisting of heart, brain, and spinal cord.

C10. The method of any one of embodiments C1-C8, wherein said damaged tissue is selected from the group consisting of cardiac tissue, neuronal tissue (including central and peripheral nervous system tissue), and vascular tissue (including major and minor arteries, veins, and capillaries).

D1. A composition comprising a pharmaceutically acceptable mixture of self-renewing, colony-forming somatic cells (CF-SC), or conditioned cell culture media derived from such cells, and purified naturally occurring or isolated recombinant extracellular matrix or blood plasma proteins.

D2. The composition of embodiment D1, wherein said CF-SC are derived from bone marrow.

D3. The composition of embodiments D1 or D2, wherein said CF-SC are derived from a human.

D4. The composition of any one of embodiments D1-D3, wherein said CF-SC are derived from an adult mammal, including humans.

D5. The composition of any one of embodiments D1-D4, wherein said CF-SC express one or more secreted proteins shown in Table 1A, 1B and 1C.

D6. The composition of any one of embodiment D1-D5, wherein said extracellular matrix or blood plasma proteins comprise one or more full-length or alternatively processed isoforms, proteolytic fragments, or subunits of molecules selected from the group consisting of:

a) collagen; b) elastin; c) fibronectin; d) laminin; e) entactin (nidogen); f) hyaluronic acid; g) polyglycolic acid (PGA); h) fibrinogen (Factor I); i) fibrin; j) prothrombin (Factor II); k) thrombin; l) anti-thrombin; m) Tissue factor Co-factor of VIIa (Factor III); n) Protein C; o) Protein S; p) protein Z; q) Protein Z-related protease inhibitor; r) heparin cofactor II; s) Factor V (proaccelerin, labile factor); t) Factor-VII; u) Factor-VIII; v) Factor-IX; w) Factor-X; x) Factor-XI; y) Factor-XII; z) Factor-XIII; aa) von Willebrand factor; ab) prekallikrein; ac) high molecular weight kininogen; ad) plasminogen; ae) plasmin; af) tissue-plasminogen activator; ag) urokinase; ah) plasminogen activator inhibitor-1; and, ai) plasminogen activator inhibitor-2.

D7. The composition of any one of embodiments D1-D6, further comprising purified naturally occurring or isolated recombinant cytokines or chemokines.

D8. The composition of any one of embodiments D1-D7, wherein said extracellular matrix, blood plasma proteins, cytokines, and/or chemokines are derived from humans.

D9. The composition of any one of embodiments D1-D8, wherein said pharmaceutically acceptable mixture forms a semi-solidified or solidified matrix.

D10. A method of treating damaged tissue with the composition of any one of embodiments D1-D8, wherein the composition is a liquid.

D11. The method of embodiment D10, wherein the liquid is applied by injection.

D12. A method of treating damaged tissue with the composition of any one of embodiments D1-D9, wherein the composition is applied as a liquid but thereafter forms a semi-solidified or solidified matrix.

D13. The method of embodiments D10-D12 wherein said tissue is damaged as a result of a condition selected from the group consisting of:

a) disease; b) physical trauma; c) ischemia; d) aging; e) burn; f) bacterial infection; g) viral infection; h) fungal infection; and, i) dysregulation of the immune system.

D14. The method of embodiment D13, wherein the damaged tissue is skin.

D15. A method of using the composition of any one of embodiments D1-D9 for facial skin rejuvenation.

D16. A method of using the composition of any one of embodiments D1-D9, wherein said composition inhibits acute inflammation.

D17. A method for treating, repairing, regenerating, or healing a damaged organ or tissue comprising contacting said damaged organ or tissue with an effective amount of self-renewing colony forming somatic cells or compositions produced from such cells so as to effect said treatment, repair, regeneration, or healing of the damaged organ or tissue.

D18. The method of embodiment D17, wherein said damaged organ or tissue is contacted with an effective amount of self-renewing colony forming somatic cells or compositions produced from such cells by means selected from the group consisting of:

a) injection into the damaged organ or tissue; b) application onto the damaged organ or tissue; c) injection proximal to the damaged organ or tissue; d) application proximal to the damaged organ or tissue; and, e) intravenous administration.

D19. The method of embodiments D17 or D18, wherein the cells are derived from bone marrow.

D20. The method of any one of embodiments D17-D19, wherein the cells are human.

D21. The method of any one of embodiments D17-D20, wherein the cells, or compositions produced by said cells, inhibit or reduce adverse immune responses (such as cell-mediated autoimmunity), fibrosis (scarring) and/or adverse tissue remodeling (for example, ventricular remodeling).

D22. The method of any one of embodiments D12-D21, wherein the cells, or compositions produced by said cells, control inflammation and/or inhibit acute inflammation.

D23. The method of any one of embodiments D17-D21, wherein the cells, or compositions produced by said cells, stimulate or enhance angiogenesis.

D24. The method of any one of embodiments D17-D21, wherein said cells do not exhibit significant or detectable levels of permanent or long-term engraftment into said damaged organs or tissues.

D25. The method of any one of embodiments D17-D24, wherein said damaged organs are selected from the group consisting of heart, brain, and spinal cord.

D26. The method of any one of embodiments D17-D24, wherein said damaged tissue is selected from the group consisting of cardiac tissue, neuronal tissue (including central and peripheral nervous system tissue), and vascular tissue (including major and minor arteries, veins, and capillaries).

D27. A method of inducing, enhancing, and/or maintaining the generation of new red blood cells in vitro.

D28. The method of embodiment D27, wherein said induction, enhancement, or maintenance is achieved by co-cultivation of hematopoietic precursor cells with self-renewing colony forming cells.

D29. The method of embodiment D28, wherein said self-renewing colony forming cells are human bone marrow-derived somatic cells (hABM-SC).

D30. The method of embodiment D29, wherein said hABM-SC are derived from an adult.

D31. The method of any one of embodiments D27-D29, wherein said co-cultivation utilizes a semi-permeable barrier to maintain separation of the hematopoietic precursor cells from the self-renewing colony forming cells while allowing exchange of compositions produced by said self-renewing colony forming cells across said barrier.

D32. The method of embodiment D27, wherein said induction, enhancement, or maintenance is achieved by co-cultivation of hematopoietic precursor cells with isolated compositions produced by self-renewing colony forming cells.

D33. The method of embodiment D32, wherein said self-renewing colony forming cells are human bone marrow-derived somatic cells (hABM-SC).

D34. The method of embodiment D33, wherein said hABM-SC are derived from an adult.

D35. The method of any one of embodiments D32-D34, wherein said isolated compositions are lyophilized.

D36. The method of any one of embodiments D32-D34, wherein said isolated compositions are cryopreserved.

D37. The method of any one of embodiments D32-D34, wherein said isolated compositions are mixed with one or more pharmaceutically acceptable carriers.

D38. A method of producing, isolating, purifying, and/or packaging cell-derived compositions and/or trophic factors.

D39. A method of producing conditioned media, wherein said media contains sera or is sera-free media.

D40. A method of isolating and purifying fractions and/or cell-derived compositions from conditioned media, wherein said media contains sera or is sera-free media.

D41. A method of isolating, cryopreserving, and/or expanding CD34+ Cord Blood Cells (CBC).

D42. The method of embodiment D41, wherein said CBC are expanded in suspension cultures.

D43. The method of embodiment D41, wherein said CBC are expanded by co-culturing with a feeder layer of self-renewing colony forming cells.

D44. The method of embodiment D43, wherein said self-renewing colony forming cells are human bone marrow-derived somatic cells (hABM-SC).

D45. A wash solution comprising Balanced Salt Solution with dextrose (BSSD).

D46. The wash solution of embodiment D45 wherein said dextrose is at a concentration of about 4.5% dextrose.

D47. The wash solution of embodiment D45 or D46, further comprising human serum albumin.

D48. The wash solution of embodiment D47, wherein said human serum albumin is at a concentration of about 5% human serum album.

D49. A cryopreservation media comprising dimethyl sulfoxide (DMSO) and human serum albumin in a Balanced Salt Solution.

D50. The cryopreservation media of embodiment D49, wherein said DMSO concentration is about 5% and said HSA concentration is about 5%.

E1. An isolated cell population derived from bone marrow, wherein greater than about 91% of the cells of the cell population co-express CD49c and CD90, and wherein the cell population has a doubling rate of less than about 30 hours.

E2. The isolated cell population of embodiment E1, wherein the cell population is derived from human bone marrow.

E3. The isolated cell population of embodiments E1 or E2, wherein the cells of the cell population that co-express CD49c and CD90 do not express CD34 and/or CD45.

E4. The isolated cell population according to any one of embodiments E1, E2, or E3, wherein the cells of the cell population that co-express CD49c and CD90 further express at least one cardiac-related transcription factor selected from the group consisting of GATA-4, Irx4, and Nkx2.5.

E5. The isolated cell population according to any one of embodiments E1, E2, or E3, wherein the cells of the cell population that co-express CD49c and CD90 further express at least one trophic factor selected from the group consisting of:
a) Brain-Derived Neurotrophic Factor (BDNF);
b) Cystatin-C;
c) Interleukin-6 (IL-6);
d) Interleukin-7 (IL-7);
e) Interleukin-11 (IL-11);
f) Nerve Growth Factor (NGF);
g) Neurotrophin-3 (NT-3);
h) Macrophage Chemoattractant Protein-1 (MCP-1);
i) Matrix Metalloproteinase-9 (MMP-9);
j) Stem Cell Factor (SCF); and,
k) Vascular Endothelial Growth Factor (VEGF).

E6. The isolated cell population according to any one of embodiments E1, E2, or E3, wherein the cells of the cell population that co-express CD49c and CD90 further express p21 or p53, and wherein expression of p53 is a relative expression of up to about 3000 transcripts of p53 per $10^6$ transcripts of an 18s rRNA and expression of p21 is a relative expression of up to about 20,000 transcripts of p21 per $10^6$ transcripts of an 18s rRNA.

E7. The isolated cell population according to any one of embodiments E1, E2, or E3, wherein the isolated cell population has been cultured in vitro through a number of population doublings selected from the group consisting of:
a) at least about 15 population doublings;
b) at least about 20 population doublings;
c) at least about 25 population doublings;
d) at least about 30 population doublings;
e) at least about 35 population doublings; and,
f) at least about 40 population doublings.

E8. A method of making an isolated cell population derived from bone marrow, wherein greater than about 91% of the cells of the cell population co-express CD49c and CD90, and wherein the cell population has a doubling rate of less than about 30 hours, comprising the steps of:
a) culturing a source of the cell population under a low oxygen condition or a low oxidative stress condition to produce an adherent cell population; and,
b) culturing the adherent cell population at a seeding density of less than about 2500 cells/cm$^2$.

E9. The method of embodiment E8, wherein the cell population is derived from human bone marrow.

E10. The method of embodiments E8 or E9, wherein the source of the cell population in embodiment 8, part a) is cultured at an initial seeding density selected from the group consisting of:
a) less than about 75000 cells/cm$^2$; and,
b) less than about 50000 cells/cm$^2$.

E11. The method of any one of embodiments E8 to E10, wherein the adherent cell population in embodiment 8, part b) is cultured at a seeding density selected from the group consisting of:
a) less than about 2500 cells/cm$^2$;
b) less than about 1000 cells/cm$^2$;
c) less than about 100 cells/cm$^2$;
d) less than about 50 cells/cm$^2$; and,
e) less than about 30 cells/cm$^2$.

E12. The method of any one of embodiments E8 to E11, wherein the low oxygen condition is selected from the group consisting of:
a) between about 1 to 10% oxygen;
b) between about 2 to 7% oxygen;
c) less than about 20% oxygen;
d) less than about 15% oxygen;
d) less than about 10% oxygen;
e) less than about 5% oxygen; and,
f) about 5% oxygen.

E13. The method of any one of embodiments E8 to E12, further including lysing the red blood cells in a source of the cell population prior to culturing the source of the cell population.

E14. The method of any one of embodiments E8 to E12, further including selecting a fractionated source of the cell population by passage through a density gradient prior to culturing the source of the cell population.

E15. The method of any one of embodiments E8 to E14, wherein the cells of the cell population that co-express CD49c and CD90, do not express CD34 and/or CD45.

E16. The method of any one of embodiments E8 to E15, wherein the cells of the cell population that co-express CD49c and CD90 further express at least one cardiac-related transcription factor selected from the group consisting of GATA-4, Irx4, and Nkx2.5.

E17. The method of any one of embodiments E8 to E15, wherein the cells of the cell population that co-express CD49c and CD90 further express at least one trophic factor selected from the group consisting of:
a) Brain-Derived Neurotrophic Factor (BDNF);
b) Cystatin-C;
c) Interleukin-6 (IL-6);
d) Interleukin-7 (IL-7);
e) Interleukin-11 (IL-11);
f) Nerve Growth Factor (NGF);
g) Neurotrophin-3 (NT-3);
h) Macrophage Chemoattractant Protein-1 (MCP-1);
i) Matrix Metalloproteinase-9 (MMP-9);
j) Stem Cell Factor (SCF); and,
k) Vascular Endothelial Growth Factor (VEGF).

E18. The method of any one of embodiments E8 to E15, wherein the cells of the cell population that co-express CD49c and CD90 further express p21 or p53, and wherein expression of p53 is a relative expression of up to about 3000 transcripts of p53 per $10^6$ transcripts of an 18s rRNA and expression of p21 is a relative expression of up to about 20,000 transcripts of p21 per $10^6$ transcripts of an 18s rRNA.

E19. The method of any one of embodiments E8 to E115, wherein the isolated cell population has been cultured in vitro through a number of population doublings selected from the group consisting of:
a) at least about 15 population doublings;
b) at least about 20 population doublings;
c) at least about 25 population doublings;
d) at least about 30 population doublings;
e) at least about 35 population doublings; and,
f) at least about 40 population doublings.

E20. Use of an isolated cell population according to any one of embodiments E1 to E7 in the manufacture of a medicament for treating a human suffering from a condition selected from the group consisting of:
a) a degenerative condition;
b) an acute injury condition;
c) a neurological condition; and,
d) a cardiac condition.

E21. Use of an isolated cell population according to any one of embodiments E1 to E7 in the manufacture of a medicament for treating a human suffering from a degenerative or acute injury condition.

E22. An isolated cell population derived from bone marrow, wherein greater than about 91% of the cells of the cell population co-express CD49c and CD90, and wherein the cell population has a doubling rate of less than about 30 hours under a low oxygen condition.

E23. The isolated cell population of embodiment E22, wherein the cell population is derived from human bone marrow.

E24. The isolated cell population of embodiments E22 or E23, wherein the low oxygen condition is between about 1 to 10% oxygen.

E25. The isolated cell population of embodiment E24, wherein the low oxygen condition is about 5% oxygen.

E26. The isolated cell population of any one of embodiments E22 to E25, wherein the cell population is cultured as an adherent cell population at a seeding density of less than about 2500 cells/cm².

E27. The isolated cell population of any one of embodiments E22 to E25, wherein the seeding density is less than about 1000 cells/cm².

E28. The isolated cell population of any one of embodiments E22 to E25, wherein the seeding density is less than about 100 cells/cm².]

E29. The isolated cell population of any one of embodiments E22 to E25, wherein the seeding density is less than about 50 cells/cm².

E30. The isolated cell population of any one of embodiments E22 to E25, wherein the seeding density is less than about 30 cells/cm².

E31. A method of making an isolated cell population, wherein greater than about 91% of the cells of the cell population co-express CD49c and CD90, and wherein the cell population has a doubling rate of less than about 30 hours, comprising the steps of:
a) aspirating bone marrow cells from a human;
b) lysing the red blood cell component of the bone marrow aspirate;
c) seeding the non-lysed bone marrow cells in a tissue culturing device;
d) allowing the non-lysed bone marrow cells to adhere to a surface;
e) culturing the adherent cells under a 5% oxygen condition; and
f) passaging the adherent cells at a seeding density of 30 cells/cm².

E32. An isolated cell population obtainable by the method of embodiment E31.

E33. An isolated cell population obtained by the method of embodiment E31.

E34. A method of making an isolated cell population, wherein greater than about 91% of the cells of the cell population co-express CD49c and CD90, and wherein the cell population has a doubling rate of less than about 30 hours after 30 cell doublings, comprising the steps of:
a) aspirating bone marrow cells from a human;
b) selecting a fractionated source of the cell population by passage through a density gradient;
c) seeding the fractionated cells in a tissue culturing device;
d) allowing the fractionated cells to adhere to a surface;
e) culturing the adherent cells under a 5% oxygen condition; and
f) passaging the adherent cells at a seeding density of 30 cells/cm².

E35. An isolated cell population obtainable by the method of embodiment E34.

E36. An isolated cell population obtained by the method of embodiment E34.

F1. A method of administering a therapeutically useful amount of a biological composition or compositions to an organ, tissue, or subject, comprising administering to said organ, tissue, or subject an isolated population of bone marrow-derived self-renewing colony-forming somatic cells (CF-SC), wherein said CF-SC do not have multipotent differentiation capacity, wherein said CF-SC have a normal karyotype, wherein said CF-SC are non-immortalized, wherein said CF-SC express CD13, CD44, CD49c, CD90, HLA Class-1 and β (beta) 2-Microglobulin, and wherein said CF-SC do not express CD10, CD34, CD45, CD62L, or CD106.

F2. A method of administering a therapeutically useful amount of a biological composition or compositions to an organ, tissue, or subject, comprising: (a) isolating the biological composition or compositions produced by an isolated population of bone marrow-derived self-renewing colony forming somatic cells (CF-SC); and, (b) administering said biological composition or compositions to said organ, tissue, or subject, wherein said CF-SC do not have multipotent differentiation capacity, wherein said CF-SC have a normal karyotype, wherein said CF-SC are non-immortalized, wherein said CF-SC express CD13, CD44, CD49c, CD90, HLA Class-1 and β (beta) 2-Microglobulin, and wherein said CF-SC do not express CD10, CD34, CD45, CD62L, or CD106.

F3. A method of administering a therapeutically useful amount of a biological composition or compositions to an organ, tissue, or subject, comprising administering to said organ, tissue, or subject an isolated population of bone marrow-derived self-renewing colony-forming somatic cells (CF-SC), wherein said CF-SC do not have multipotent differentiation capacity, wherein said CF-SC have a normal karyotype, wherein said CF-SC are non-immortalized, and wherein said CF-SC are obtained from bone marrow by steps comprising: i) incubating bone marrow cells under a low oxygen condition such that said bone marrow cells when allowed to adhere to a tissue culture-treated surface produce adherent colony forming units; and, ii) passaging cells in said adherent colony forming units at low cell seeding densities.

F4. A method of administering a therapeutically useful amount of a biological composition or compositions to an organ, tissue, or subject, comprising: (a) isolating the biological composition or compositions produced by an isolated population of bone marrow-derived self-renewing colony forming somatic cells (CF-SC); and, (b) administering said biological composition or compositions to said organ, tissue, or subject, wherein said CF-SC do not have multipotent differentiation capacity, wherein said CF-SC have a normal karyotype, wherein said CF-SC are non-immortalized, and wherein said CF-SC are obtained from bone marrow by steps comprising: i) incubating bone marrow cells under a low oxygen condition such that said bone marrow cells when allowed to adhere to a tissue culture-treated surface produce adherent colony forming units; and, ii) passaging cells in said adherent colony forming units at low cell seeding densities.

F5. A method of preventing tissue damage or of repairing, treating, or promoting regeneration of damaged tissue, comprising administering to an organ, tissue, or subject an isolated population of bone marrow-derived self-renewing colony-forming cells somatic cells (CF-SC), wherein said CF-SC do not have multipotent differentiation capacity, wherein said CF-SC have a normal karyotype, wherein said CF-SC are non-immortalized, wherein said CF-SC express CD13, CD44, CD49c, CD90, HLA Class-1 and β (beta) 2-Microglobulin, and wherein said CF-SC do not express CD10, CD34, CD45, CD62L, or CD106.

F6. A method of preventing tissue damage or of repairing, treating, or promoting regeneration of damaged tissue in an organ, tissue, or subject, comprising: (a) isolating the biological composition or compositions produced by an isolated population of bone marrow-derived self-renewing colony forming somatic cells (CF-SC); and, (b) administering said biological composition or compositions to said organ, tissue, or subject, wherein said CF-SC do not have multipotent differentiation capacity, wherein said CF-SC have a normal karyotype, wherein said CF-SC are non-immortalized, wherein said CF-SC express CD13, CD44, CD49c, CD90, HLA Class-1 and β (beta) 2-Microglobulin, and wherein said CF-SC do not express CD10, CD34, CD45, CD62L, or CD106.

F7. A method of preventing tissue damage or of repairing, treating, or promoting regeneration of damaged tissue in an organ, tissue, or subject, comprising administering to said organ, tissue, or subject an isolated population of bone marrow-derived self-renewing colony-forming cells somatic cells (CF-SC), wherein said CF-SC do not have multipotent differentiation capacity, wherein said CF-SC have a normal karyotype, wherein said CF-SC are non-immortalized, and wherein said CF-SC are obtained from bone marrow by steps comprising: i) incubating bone marrow cells under a low oxygen condition such that said bone marrow cells when allowed to adhere to a tissue culture-treated surface produce adherent colony forming units; and, ii) passaging cells in said adherent colony forming units at low cell seeding densities.

F8. A method of preventing tissue damage or of repairing, treating, or promoting regeneration of damaged tissue in an organ, tissue, or subject, comprising: (a) isolating the biological composition or compositions produced by an isolated population of bone marrow-derived self-renewing colony forming somatic cells (CF-SC); and, (b) administering said biological composition or compositions to said organ, tissue, or subject, wherein said CF-SC do not have multipotent differentiation capacity, wherein said CF-SC have a normal karyotype, wherein said CF-SC are non-immortalized, and wherein said CF-SC are obtained from bone marrow by steps comprising: i) incubating bone marrow cells under a low oxygen condition such that said bone marrow cells when allowed to adhere to a tissue culture-treated surface produce adherent colony forming units; and, ii) passaging cells in said adherent colony forming units at low cell seeding densities.

F9. A method of treating or reducing inflammation, immune, or autoimmune activity in a organ, tissue, or subject, comprising administering to said organ, tissue, or subject an isolated population of bone marrow-derived self-renewing colony-forming cells somatic cells (CF-SC), wherein said CF-SC do not have multipotent differentiation capacity, wherein said CF-SC have a normal karyotype, wherein said CF-SC are non-immortalized, wherein said CF-SC express CD13, CD44, CD49c, CD90, HLA Class-1 and β (beta) 2-Microglobulin, and wherein said CF-SC do not express CD10, CD34, CD45, CD62L, or CD106.

F10. A method of treating or reducing inflammation, immune, or autoimmune activity in an organ, tissue, or subject, comprising: (a) isolating the biological composition or compositions produced by an isolated population of bone marrow-derived self-renewing colony forming somatic cells (CF-SC); and, (b) administering said biological composition or compositions to said organ, tissue, or subject, wherein said CF-SC do not have multipotent differentiation capacity, wherein said CF-SC have a normal karyotype, wherein said CF-SC are non-immortalized, wherein said CF-SC express CD13, CD44, CD49c, CD90, HLA Class-1 and β (beta) 2-Microglobulin, and wherein said CF-SC do not express CD10, CD34, CD45, CD62L, or CD106.

F11. A method of treating or reducing inflammation, immune, or autoimmune activity in an organ, tissue, or subject, comprising administering to said organ, tissue, or subject an isolated population of bone marrow-derived self-renewing colony-forming cells somatic cells (CF-SC), wherein said CF-SC do not have multipotent differentiation capacity, wherein said CF-SC have a normal karyotype, wherein said CF-SC are non-immortalized, and wherein said CF-SC are obtained from bone marrow by steps comprising: i) incubating bone marrow cells under a low oxygen condition such that said bone marrow cells when allowed to adhere to a tissue culture-treated surface produce adherent colony forming units; and, ii) passaging cells in said adherent colony forming units at low cell seeding densities.

F12. A method of treating or reducing inflammation, immune, or autoimmune activity in a organ, tissue, or subject, comprising: (a) isolating the biological composition or compositions produced by an isolated population of bone marrow-derived self-renewing colony forming somatic cells (CF-SC); and, (b) administering said biological composition or compositions to said organ, tissue, or subject, wherein said CF-SC do not have multipotent differentiation capacity; wherein said CF-SC have a normal karyotype, wherein said CF-SC are non-immortalized, and wherein said CF-SC are obtained from bone marrow by steps comprising: i) incubating bone marrow cells under a low oxygen condition such that said bone marrow cells when allowed to adhere to a tissue culture-treated surface produce adherent colony forming units; and, ii) passaging cells in said adherent colony forming units at low cell seeding densities.

F13. The method of any one of embodiments F1, F2, F5, F6, F9, or F10, wherein said CF-SC further express one or more molecules selected from the group consisting of: a) CD29; b) CD59; c) CD147; d) CD166; and, e) telomerase and, wherein said CF-SC further do not express one or more molecules selected from the group consisting of: f) CD11c; g) CD14; h) CD33; i) CD62P; j) CD80; k) STRO-1; l) HLA-Class-II; m) CD178. n) p53; and, o) p21.

F14. The method of any one of embodiments F3, F4, F7, F8, F11 or F12, wherein said low oxygen condition is about 5% oxygen.

F15. The method of any one of embodiments F3, F4, F7, F8, F11 or F12, wherein said low oxygen condition is selected from the group consisting of: a) less than about 20% oxygen; b) less than about 15% oxygen; c) less than about 10% oxygen; d) less than about 5% oxygen; e) between about 1 to 10% oxygen; f) between about 2 to 7% oxygen; g) between about 3 to 6% oxygen; h) between about 4 to 6% oxygen; and, i) between about 4 to 5% oxygen.

F16. The method of any one of embodiments F3, F4, F7, F8, F11 or F12, wherein said low cell seeding density is less than about 200 cells/cm$^2$.

F17. The method of any one of embodiments F3, F4, F7, F8, F11 or F12, wherein said low cell seeding density is less than about 100 cells/cm$^2$.

F18. The method of any one of embodiments F3, F4, F7, F8, F11 or F12, wherein said low cell seeding density is less than about 50 cells/cm$^2$.

F19. The method of any one of embodiments F3, F4, F7, F8, F11 or F12, wherein said low cell seeding density is less than about 30 cells/cm$^2$.

F20. The method of any one of embodiments F3, F4, F7, F8, F11 or F12, wherein said low cell seeding density is selected from the group consisting of: a) less than about 2500 cells/cm$^2$; b) less than about 1000 cells/cm$^2$; and, c) less than about 500 cells/cm$^2$.

F21. The method of any one of embodiments F1 to F20, wherein lack of said multipotent differentiation capacity comprises the inability of said CF-SC to differentiate into osteocytes.

F22. The method of any one of embodiments F1 to F20, wherein lack of said multipotent differentiation capacity comprises the inability of said CF-SC to deposit detectable levels of calcium following treatment of said CF-SC under osteoinductive conditions.

F23. The method of embodiment F22, wherein said treatment comprises exposure of said CF-SC to media containing one or more components selected from the group consisting of: a) dexamethasone; b) ascorbate; and, c) beta glycerophosphate.

F24. The method of embodiment F23, wherein said treatment further comprises exposure to Noggin.

F25. The method of any one of embodiments F1 to F20, wherein lack of said multipotent differentiation capacity comprises the inability of said CF-SC to differentiate into chondrocytes.

F26. The method of any one of embodiments F1 to F20, wherein lack of said multipotent differentiation capacity comprises the inability of said CF-SC to differentiate into adipocytes.

F27. The method of any one of embodiments F1 to F20, wherein said CF-SC have unipotent differentiation capacity.

F28. The method of any one of embodiments F1 to F27, wherein said CF-SC have substantial capacity for self-renewal.

F29. The method of any of embodiments F1 to F28, wherein said CF-SC maintain an approximately constant population doubling rate through multiple in vitro cell doublings.

F30. The method of any one of embodiments F1 to F29, wherein said CF-SC are not embryonic stem cells, hematopoietic stem cells, mesenchymal stem cells, multipotent adult progenitor cells (MASCs), multipotent adult stem cells (MASCs), or fibroblasts.

F31. The method of any one of embodiments F1 to F30, wherein said bone marrow is human bone marrow.

F32. The method of any one of embodiments F1 to F31, wherein said cell population has undergone a number of population doublings selected from the group consisting of: a) at least about 15 population doublings; b) at least about 20 population doublings; c) at least about 25 population doublings; d) at least about 30 population doublings; e) at least about 35 population doublings; f) at least about 40 population doublings; g) at least about 45 population doublings; and, h) at least about 50 population doublings.

F33. The method of any one of embodiments F1 to F32, wherein said organ, tissue, or subject is human.

F34. The method of any one of embodiments F1 to F33, wherein said method is used to treat or prevent cell, organ, or tissue damage, or diseases and disorders selected from the group consisting of: a) neurological damage, disease or disorder; b) cardiac damage, disease or disorder; c) skin damage, disease or disorder; d) periodontal damage, disease or disorder; e) maxillofacialary damage, disease or disorder; 0 skeletal muscle damage, disease or disorder; g) ligament damage, disease or disorder; h) pulmonary damage, disease or disorder; i) hepatic damage, disease or disorder; j) renal damage, disease or disorder; k) genitourinary system damage, disease or disorder; 1) bladder damage, disease or disorder; m) endocrine damage, disease or disorder; n) hematopoietic damage, disease or disorder; o) pancreatic damage, disease or disorder; p) diabetes; q) ocular damage, disease or disorder; r) retinal damage, disease or disorder; s) gastrointestinal disease or disorder; t) splenic damage, disease or disorder; u) immunological damage, disease or disorder; v) autoimmune damage, disease or disorder; w) inflammatory damage, disease or disorder; x) hyperproliferative damage, disease or disorder; and, y) cancer.

F35. The method of any one of embodiments F5 to F8, wherein said damage is prevented in an organ or tissue during the course of organ or tissue transplant.

F36. The method of any one of embodiments F1 to F35, wherein said cells are genetically modified.

F37. The method of embodiment F36, wherein said cells are genetically modified by introduction of a recombinant nucleic acid molecule.

F38. A composition comprising a pharmaceutically acceptable mixture of purified naturally occurring or isolated recombinant extracellular matrix or blood plasma proteins and bone marrow-derived self-renewing colony-forming somatic cells (CF-SC), wherein said CF-SC have a normal karyotype, wherein said CF-SC are non-immortalized, wherein said CF-SC express CD13, CD44, CD49c, CD90, HLA Class-1 and β (beta) 2-Microglobulin, and wherein said CF-SC do not express CD10, CD34, CD45, CD62L, or CD106.

F39. A composition comprising a pharmaceutically acceptable mixture of purified naturally occurring or isolated recombinant extracellular matrix or blood plasma proteins and a biological composition or compositions produced by an isolated population of bone marrow-derived self-renewing colony forming somatic cells (CF-SC), wherein said CF-SC have a normal karyotype, wherein said CF-SC are non-immortalized, wherein said CF-SC express CD13, CD44, CD49c, CD90, HLA Class-1 and β (beta) 2-Microglobulin, and wherein said CF-SC do not express CD10, CD34, CD45, CD62L, or CD106.

F40. A composition comprising a pharmaceutically acceptable mixture of purified naturally occurring or isolated recombinant extracellular matrix or blood plasma proteins and bone marrow-derived self-renewing colony-forming somatic cells (CF-SC), wherein said CF-SC have a normal karyotype, wherein said CF-SC are non-immortalized, and wherein said CF-SC are obtained from bone marrow by steps comprising: i) incubating bone marrow cells under a low oxygen condition such that said bone marrow cells when allowed to adhere to a tissue culture-treated surface produce adherent colony forming units; and, ii) passaging cells in said adherent colony forming units at low cell seeding densities.

F41. A composition comprising a pharmaceutically acceptable mixture of purified naturally occurring or isolated recombinant extracellular matrix or blood plasma proteins and a biological composition or compositions produced by an isolated population of bone marrow-derived self-renewing colony forming somatic cells (CF-SC), wherein said CF-SC have a normal karyotype, wherein said CF-SC are non-immortalized, and wherein said CF-SC are obtained from bone marrow by steps comprising: i) incubating bone marrow cells under a low oxygen condition such that said bone marrow cells when allowed to adhere to a tissue culture-treated surface produce adherent colony forming units; and, ii) passaging cells in said adherent colony forming units at low cell seeding densities.

F42. The composition of any one of embodiments F38 to F41, wherein said extracellular matrix or blood plasma proteins comprise one or more full-length or alternatively processed isoforms, proteolytic fragments, or subunits of molecules selected from the group consisting of: a) collagen; b) elastin; c) fibronectin; d) laminin; e) entactin (nidogen); hyaluronic acid; g) polyglycolic acid (PGA) h) fibrinogen (Factor I); i) fibrin; j) prothrombin (Factor II); k) thrombin; 1) anti-thrombin; m) Tissue factor Co-factor of VIIa (Factor III);

n) Protein C; o) Protein S; p) protein Z; q) Protein Z-related protease inhibitor; r) heparin cofactor II; s) Factor V (proaccelerin, labile factor); t) Factor-VII; u) Factor-VIII; v) Factor-IX; w) Factor-X; x) Factor-XI; y) Factor-XII; z) Factor-XIII; aa) von Willebrand factor; ab) prekallikrein; ac) high molecular weight kininogen; ad) plasminogen; ae) plasmin; af) tissue-plasminogen activator; ag) urokinase; ah) plasminogen activator inhibitor-1; and, ai) plasminogen activator inhibitor-2.

F43. The composition of any one of embodiments F38 to F42, further comprising purified naturally occurring or isolated recombinant cytokines or chemokines.

F44. The composition of embodiment F38 or F39, wherein said CF-SC further express one or more molecules selected from the group consisting of: a) CD29; b) CD59; c) CD147; d) CD166; and, e) telomerase and, wherein said CF-SC further do not express one or more molecules selected from the group consisting of: CD11c; g) CD14; h) CD33; i) CD62P; j) CD80; k) STRO-1; l) HLA-Class-II; m) CD178; n) p53; and, o) p21.

F45. The composition of embodiment F40 or F41, wherein said low oxygen condition is about 5% oxygen.

F46. The composition of embodiment F40 or F41, wherein said low oxygen condition is selected from the group consisting of: a) less than about 20% oxygen; b) less than about 15% oxygen; c) less than about 10% oxygen; d) less than about 5% oxygen; e) between about 1 to 10% oxygen; f) between about 2 to 7% oxygen; g) between about 3 to 6% oxygen; h) between about 4 to 6% oxygen; and, i) between about 4 to 5% oxygen.

F47. The composition of embodiment F40 or F41, wherein said low cell seeding density is less than about 200 cells/cm$^2$.

F48. The composition of embodiment F40 or F41, wherein said low cell seeding density is less than about 100 cells/cm$^2$.

F49. The composition of embodiment F40 or F41, wherein said low cell seeding density is less than about 50 cells/cm$^2$.

F50. The composition of embodiment F40 or F41, wherein said low cell seeding density is less than about 30 cells/cm$^2$.

F51. The composition of embodiment F40 or F41, wherein said low cell seeding density is selected from the group consisting of: a) less than about 2500 cells/cm$^2$; b) less than about 1000 cells/cm$^2$; and, c) less than about 500 cells/cm$^2$.

F52. The composition of any one of embodiments F38 to F51, wherein said CF-SC have unipotent differentiation capacity.

F53. The composition of any one of embodiments F38 to F52, wherein said CF-SC have substantial capacity for self-renewal.

F54. The composition of any of embodiments F38 to F53, wherein said CF-SC maintain an approximately constant population doubling rate through multiple in vitro cell doublings.

F55. The composition of any one of embodiments F38 to F54, wherein said CF-SC are not embryonic stem cells, hematopoietic stem cells, mesenchymal stem cells, multipotent adult progenitor cells (MAPCs), multipotent adult stem cells (MASCs), or fibroblasts.

F56. The composition of any one of embodiments F38 to F55, wherein said bone marrow is human bone marrow.

F57. The composition of any one of embodiments F38 to F56, wherein said cell population has undergone a number of population doublings selected from the group consisting of: a) at least about 15 population doublings; b) at least about 20 population doublings; c) at least about 25 population doublings; d) at least about 30 population doublings; e) at least about 35 population doublings; f) at least about 40 population doublings; g) at least about 45 population doublings; and, h) at least about 50 population doublings.

F58. The composition of any one of embodiments F38 to F57, wherein said organ, tissue, or subject is human.

F59. The composition of any one of embodiments F38 to F58, wherein said method is used to treat cell, organ, or tissue damage, diseases and disorders selected from the group consisting of: a) neurological damage, disease or disorder; b) cardiac damage, disease or disorder; c) skin damage, disease or disorder; d) periodontal damage, disease or disorder; e) maxillofacialary damage, disease or disorder order; 1) skeletal muscle damage, disease or disorder; g) ligament damage, disease or disorder; h) respiratory damage, disease or disorder; i) hepatic damage, disease or disorder; j) renal damage, disease or disorder; k) genitourinary system damage, disease or disorder; l) bladder damage, disease or disorder; m) endocrine damage, disease or disorder; n) hematopoietic damage, disease or disorder; o) pancreatic damage, disease or disorder; p) diabetes; q) ocular damage, disease or disorder; r) retinal damage, disease or disorder; s) gastrointestinal disease or disorder; t) splenic damage, disease or disorder; u) immunological damage, disease or disorder; v) autoimmune damage, disease or disorder; w) inflammatory damage, disease or disorder; x) hyperproliferative damage, disease or disorder; and, y) cancer.

F60. The composition of any one of embodiments F38 to F59, wherein said cells are genetically modified.

F61. The composition of embodiment F60, wherein said cells are genetically modified by introduction of a recombinant nucleic acid molecule.

F62. The composition of any one of embodiments F38 to F61, wherein said pharmaceutically acceptable mixture forms a semi-solidified or solidified matrix.

F63. A method of treating damaged tissue with the composition of any one of embodiments F38 to F62, wherein the composition is a liquid.

F64. The method of embodiment F63, wherein the liquid is applied by injection.

F65. A method of treating damaged tissue with the composition of any one of embodiments F38 to F64, wherein the composition is applied as a liquid but thereafter forms a semi-solidified or solidified matrix.

F66. The method or composition of any one of embodiments F1 to F65, wherein said CF-SC or biological composition or compositions produced by said CF-SC are administered by a means selected from the group consisting of: a) injection into the damaged organ or tissue; b) application onto the damaged organ or tissue; c) injection proximal to the damaged organ or tissue; d) application proximal to the damaged organ or tissue; e) intravenous administration; and, f) organ or tissue perfusion.

F67. The method or composition of any one of embodiments F1 to F66, wherein said CF-SC, or biological composition or compositions produced by said CF-SC, inhibit or reduce one or more biological effects selected from the group consisting of: a) adverse immune responses; b) fibrosis; c) adverse tissue remodeling; d) organ or tissue ischemia; and, e) cell death.

F68. The method or composition of embodiment F67, wherein said adverse immune responses are selected from the group consisting of: a) autoimmune responses; b) inflammation; c) immune cell proliferation; d) immune cell activation; e) immune cell degranulation; and, f) T-cell mediated immune responses.

F69. The method or composition of any one of embodiments F1 to F68, wherein said CF-SC, or biological composition or compositions produced by said CF-SC, stimulate or enhance angiogenesis.

F70. A method of inducing, enhancing, and/or maintaining the generation of new red blood cells in vitro or in vivo, wherein said induction, enhancement, or maintenance is achieved by co-cultivation of hematopoietic precursor cells with bone marrow-derived self-renewing colony-forming somatic cells (CF-SC), wherein said CF-SC have a normal karyotype, wherein said CF-SC are non-immortalized, wherein said CF-SC express CD13, CD44, CD49c, CD90, HLA Class-1 and β (beta) 2-Microglobulin, and wherein said CF-SC do not express CD10, CD34, CD45, CD62L, or CD106.

F71. A method of inducing, enhancing, and/or maintaining the generation of new red blood cells in vitro or in vivo, wherein said induction, enhancement, or maintenance is achieved by co-cultivation of hematopoietic precursor cells with a biological composition or compositions produced by bone marrow-derived self-renewing colony-forming somatic cells (CF-SC), wherein said CF-SC have a normal karyotype, wherein said CF-SC are non-immortalized, wherein said CF-SC express CD13, CD44, CD49c, CD90, HLA Class-1 and β (beta) 2-Microglobulin, and wherein said CF-SC do not express CD10, CD34, CD45, CD62L, or CD106.

F72. The method of embodiment F70 or F71, wherein said CF-SC further express one or more molecules selected from the group consisting of: a) CD29; b) CD59; c) CD147; d) CD166; and, e) telomerase and, wherein said CF-SC further do not express one or more molecules selected from the group consisting of: f) CD11c; g) CD14; h) CD33; i) CD62P; j) CD80; k) STRO-1; l) HLA-Class-II; m) CD178; n) p53; and, o) p21.

F73. A method of inducing, enhancing, and/or maintaining the generation of new red blood cells in vitro or in vivo, wherein said induction, enhancement, or maintenance is achieved by co-cultivation of hematopoietic precursor cells with bone marrow-derived self-renewing colony-forming somatic cells (CF-SC), wherein said CF-SC have a normal karyotype, wherein said CF-SC are non-immortalized, and wherein said CF-SC are obtained from bone marrow by steps comprising: i) incubating bone marrow cells under a low oxygen condition such that said bone marrow cells when allowed to adhere to a tissue culture-treated surface produce adherent colony forming units; and, ii) passaging cells in said adherent colony forming units at low cell seeding densities.

F74. A method of inducing, enhancing, and/or maintaining the generation of new red blood cells in vitro or in vivo, wherein said induction, enhancement, or maintenance is achieved by co-cultivation of hematopoietic precursor cells with a biological composition or compositions produced by an isolated population of bone marrow-derived self-renewing colony forming somatic cells (CF-SC), wherein said CF-SC have a normal karyotype, wherein said CF-SC are non-immortalized, and wherein said CF-SC are obtained from bone marrow by steps comprising: i) incubating bone marrow cells under a low oxygen condition such that said bone marrow cells when allowed to adhere to a tissue culture-treated surface produce adherent colony forming units; and, ii) passaging cells in said adherent colony forming units at low cell seeding densities.

F75. The method of embodiment F73 or F74, wherein said low oxygen condition is about 5% oxygen.

F76. The method of embodiment F73 or F74, wherein said low oxygen condition is selected from the group consisting of: a) less than about 20% oxygen; b) less than about 15% oxygen; c) less than about 10% oxygen; d) less than about 5% oxygen; e) between about 1 to 10% oxygen; f) between about 2 to 7% oxygen; g) between about 3 to 6% oxygen; h) between about 4 to 6% oxygen; and, i) between about 4 to 5% oxygen.

F77. The method of embodiment F73 or F74, wherein said low cell seeding density is less than about 200 cells/cm$^2$.

F78. The method of embodiment F73 or F74, wherein said low cell seeding density is less than about 100 cells/cm$^2$.

F79. The method of embodiment F73 or F74, wherein said low cell seeding density is less than about 50 cells/cm$^2$.

F80. The method of embodiment F73 or F74, wherein said low cell seeding density is less than about 30 cells/cm$^2$.

F81. The method of embodiment F73 or F74, wherein said low cell seeding density is selected from the group consisting of: a) less than about 2500 cells/cm$^2$; b) less than about 1000 cells/cm$^2$; and, c) less than about 500 cells/cm$^2$.

F82. The method of any one of embodiments F70 to F81, wherein said CF-SC have unipotent differentiation capacity.

F83. The method of any one of embodiments F70 to F82, wherein said CF-SC have substantial capacity for self-renewal.

F84. The method of any one of embodiments F70 to F83, wherein said CF-SC maintain an approximately constant population doubling rate through multiple in vitro cell doublings.

F85. The method of any one of embodiments F70 to F84, wherein said CF-SC are not embryonic stem cells, hematopoietic stem cells, mesenchymal stem cells, multipotent adult progenitor cells (MAPCs), multipotent adult stem cells (MASCs), or fibroblasts.

F86. The method of any one of embodiments F70 to F85, wherein said bone marrow is human bone marrow.

F87. The method of any one of embodiments F70 to F86, wherein said cell population has undergone a number of population doublings selected from the group consisting of: a) at least about 15 population doublings; b) at least about 20 population doublings; c) at least about 25 population doublings; d) at least about 30 population doublings; e) at least about 35 population doublings; f) at least about 40 population doublings; g) at least about 45 population doublings; and, h) at least about 50 population doublings.

F88. The method of any one of embodiments F70 to F87, wherein said cell population is human.

F89. The method of any one of embodiments F9 to F12, wherein said treatment or reduction of inflammation, immune, or autoimmune activity results in one or more changes selected from the group consisting of: a) decreased focal or systemic levels of IL-13; b) decreased focal or systemic levels of TNF-alpha; c) increased focal or systemic levels of IL-2; d) decreased focal or systemic immune cell proliferation; e) decreased focal or systemic immune cell activation; and, f) decreased focal or systemic immune cell degranulation.

F90. The method of embodiment F89, wherein said decreased immune cell proliferation comprises inhibition of proliferation of one or more cell types selected from the group consisting of: a) monocytes; b) granulocytes; c) lymphocytes; and, d) neutrophils.

F91. The method of embodiment F89, wherein said increased focal or systemic levels of IL-2 supports maturation of T-cell regulatory cells.

F92. The method or composition of any one of embodiments F1-F91, wherein said biological composition or compositions are lyophilized.

F93. The method or composition of any one of embodiments F1-F91, wherein said biological composition or compositions are cryopreserved.

F94. The method or composition of any one of embodiments F1-F91, wherein said biological composition or compositions are mixed with one or more pharmaceutically acceptable carriers.

EXAMPLES

Example 1

Bioactivity of Adult Bone Marrow-Derived Somatic Cells: Production of Serum-Free Conditioned Media Production of serum-free conditioned media was produced as described below for use in assays, such as the solid-phase antibody capture of secreted proteins (also as described below). Human exABM-SC (Lot #RECB-819; at ~43 population doublings) were thawed and re-suspended in either Advanced DMEM (GIBCO™; Catalog #12491-015, Lot #1216032 (Invitrogen Corp., Carlsbad, Calif., USA)) supplemented with 4 mM L-glutamine (Catalog #SH30034.01. Lot #134-7944, (HYCLONE™ Laboratories Inc., Logan, Utah, USA)) or HyQ® RPMI-1640 (HYCLONE™ Catalog #SH30255.01, Lot #ARC25868) containing 4 mM L-glutamine and supplemented with Insulin-Transferrin-Selenium-A (ITS) (GIBCO™; Catalog #51300-044, Lot #1349264). Cell suspensions were then seeded in T-225 cm$^2$ CELLBIND™ (Corning Inc., NY, USA) culture flasks (culture surfaces treated with a patented microwave plasma process; see, U.S. Pat. No. 6,617,152) (n=3) at 20,000 cells/cm$^2$ in 36 mL of media (n=3 per condition). Cultures were placed in a 37° C. humidified trigas incubator (4% $O_2$, 5% $CO_2$, balanced with nitrogen) for approximately 24 hours. Cultures were then re-fed with fresh media on same day to remove non-adherent debris and returned to the incubator. On day 3, cell culture media were concentrated using 20 mL CENTRICON™ PLUS-20 Centrifugal Filter Units (Millipore Corp., Billerica, Mass., USA), as per manufacturer's instructions. Briefly, concentrators were centrifuged for 45 minutes at 1140×G. Concentrated supernatants were transferred to clean 2 mL cryovials and stored at –80° C. Fresh culture media were also concentrated as described for use as a negative control. The cells were then removed from the flasks using 0.25% porcine trypsin EDTA (CELLGRO™; Catalog #30-004-C1 (Mediatech Inc., Herndon, Va., USA)). Trypsin was then neutralized by adding back an equal volume of cell culture media containing 10% fetal bovine serum. Cell count and viability analysis was performed using a COULTER™ AcT 10 Series Analyzer (Beckman Coulter, Fullerton, Calif.) and trypan blue exclusion assays, respectively.

To perform 2D SDS-PAGE, human ABM-SC (Lot #PCH627; at ~27 population doublings) were thawed and re-suspended in either HyQ® Minimum Essential Medium (MEM), Alpha Modification (HYCLONE™; Catalog #SH30265.01, Lot #ASA28110) supplemented with 4 mM L-glutamine (HYCLONE™; Catalog #SH30034.01, Lot #134-7944)) or RPMI1640 (HYCLONE™; Catalog #SH30255.01) supplemented with 4 mM L-glutamine (HYCLONE™; Catalog #SH30034.01, Lot #134-7944). Cell suspensions were then seeded in T-225 cm$^2$ CELLBIND™ culture flasks (n=3) at 24-40,000 cells/cm$^2$ in 36 mL of media (n=3 per condition). Cultures were placed in a 37° C. humidified trigas incubator (4% $O_2$, 5% $CO_2$, balanced with nitrogen) for approximately 24 hours. Cultures were re-fed with fresh media on same day to remove non-adherent debris and then returned to the incubator. The following day, conditioned media were collected, pooled, and centrifuged at 1140×G for 15 minutes to remove cell debris, and then transferred to sterile centrifuge tubes for short-term storage at –80° C.

Example 2

Two Dimensional (2-D) SDS PAGE Separation of Secreted Factors (FIG. 1)

Frozen aliquots of conditioned media and control media (samples) were shipped to Kendrick Labs, Inc. (Madison, Wis.) for analysis. Prior to use, samples were thawed and warmed to room temperature. Approximately 50 mL of each sample was lyophilized then re-dissolved in 200 microL of SDS Boiling Buffer (5% sodium dodecyl sulfate, 5% beta mercaptoethanol ethanol, 10% glycerol and 60 mM Tris, pH 6.8) and 2 mL of ultrapure water. The samples were then dialyzed against 5 mM Tris, pH 7.0 for two days at 4° C. using 6-8,000 MWCO membranes. The final dialysis was performed using water only. The samples were lyophilized once again, re-dissolved in 200 microL of SDS Boiling Buffer, and heated in a boiling water bath for 5 minutes before loading into the gels.

Two-dimensional gel electrophoresis was performed according to the method of O'Farrell (O'Farrell, P. H., *J. Biol. Chem.* 250: 4007-4021, 1975) as follows: Isoelectric focusing was first carried out in glass tubes of inner diameter 2.0 mm using 2.0% ampholines, pH 3.5-10 (Amersham Biosciences, Piscataway, N.J.) for 20,000 volt-hrs. 50 ng of IEF internal standard (tropomyosin) was then added to each sample. The tropomyosin standard is used as a reference point on the gel, it migrates as a doublet with a lower polypeptide spot of MW 33,000 and pI 5.2. The tube gel pH gradient for this set of ampholines was determined using a surface pH electrode.

After equilibration for 10 min in buffer 0 (10% glycerol, 50 mm dithiothreitol, 2.3% SDS, 0.0625 M tris, pH 6.8) each tube gel was sealed to the top of a stacking gel that, itself, is placed on top of a 12% acrylamide slab gel (1.0 mm thickness). SDS slab gel electrophoresis was carried out for about 5 hours at 25 mA. The following proteins (Sigma Chemical Co.) were added as molecular weight standards to a single well in the agarose portion of the gel (the agarose is cast between the tube gel to the slab gel): myosin (220,000 daltons), phosphorylase A (94,000 daltons), catalase (60,000 daltons), actin (43,000 daltons), carbonic anhydrase (29,000 daltons), and lysozyme (14,000 daltons). Following silver-staining the standards appear as bands on the basic edge of the acrylamide slab gel (Oakley et al. Anal. Biochem. 105:361-363, 1980). The gel was then dried between two sheets of cellophane paper with the acid end to the left (FIG. 1). If gels are intended for use with mass spectroscopy analysis they are stained using the silver stain method of O'Connell and Stults (O'Connell and Stults. *Electrophoresis.* 18:349-359, 1997).

The results show that using the methods provided, human ABM-SC can be cultured in the absence of animal serum to produce conditioned media rich in secreted proteins, and that such proteins can be individually identified and isolated. Conditioned media produced in such can also be processed, alternatively, by fractionating the expressed proteins based on a range of molecular weights. Techniques for protein concentration and fractionation are well-known and routinely used by those of ordinary skill in the art. These techniques include

Example 3A

Pro-Regenerative Cytokine Secretion by Human ABM-SC

Human ABM-SC were plated in triplicate at 6,000 viable cells/cm$^2$ in cell culture "T" flasks containing AFG104 media. After allowing cells to attach and equilibrate for 24 hours, culture media was completely changed and flasks were incubated for 72 hours. Media was collected, centrifuged and stored at −80° C. until analysis for cytokines using commercially available colorimetric ELISA assay kits. For analysis of secreted cytokine release, sister flasks were treated with 10 mg/mL TNF-alpha, added during the last 24 hours of the 72 hour incubation. For each, lot three flasks of cells and supernatant were prepared, processed and banked independently for the basal and stimulated conditions, designated Basal Flask A, B and C or Stimulated Flask A, B and C, respectively.

Results show that when sub-cultured, ABM-SC secrete potentially therapeutic concentrations of several growth factors and cytokines known to augment angiogenesis, inflammation and wound healing. See, FIG. 11. Hence, ABM-SC have been shown to consistently secrete several cytokines and growth factors in vitro; including proangiogenic factors (e.g., SDF-1 alpha, VEGF, ENA-78 and angiogenin), immunomodulators (e.g., IL-6 and IL-8) and scar inhibitors/wound healing modulators (e.g., MMP-1, MMP-2, MMP-13 and Activin-A). Furthermore, the release of several of these factors is modulated by tumor necrosis factor alpha (TNF-alpha), a known inflammatory cytokine released during the course of acute tissue injury.

Example 3B

Solid-Phase Capture and Identification of Secreted Factors (Table 1A, 1B and 1C)

Conditioned media were screened for the presence of various proteins such as cytokines, proteases, and soluble receptors by solid phase antibody capture protein array, using RAYBIO™ Human Cytokine Antibody Array (RayBiotech, Inc., Norcross, Ga., USA). Briefly, frozen aliquots of conditioned media were thawed and warmed to room temperature prior to use. Array membranes were placed into the well of an eight-well tray (C series 1000). To each well, 2 mL 1× Blocking Buffer (RayBiotech, Inc.) was added and then incubated at room temperature for 30 min to block the membranes. Blocking Buffer was then decanted from each container, and the membranes were then incubated with conditioned media (diluted 1:10 with Blocking Buffer) at room temperature for 1 hr. Fresh cell culture media were used in place of PBS as negative controls. Samples were then decanted from each container and washed 3 times with 2 mL of 1× Wash Buffer I (RayBiotech, Inc.) at room temperature, while shaking for 5 min. Array membranes were then placed into one well, with 1 mL biotin-conjugated secondary antibody prepared in 1× Blocking Buffer, and incubated at room temperature for 1 hr. Arrays were then washed several times with Wash Buffer. 2 mL HRP-conjugated streptavidin diluted 1:1000 with 1× Blocking Buffer was added to each membrane and then incubated at room temperature for 2 hrs. Membranes were then washed several times with 1× Wash Buffer. Detection reagents for chemiluminescence were prepared as per manufacturer's instructions (RayBiotech, Inc.) and applied to each membrane and incubated at room temperature for 2 minute. Membranes were then placed protein side up on a plastic sheet. The opposite of the membrane was then covered with another piece of plastic sheet. Air bubbles were purged from the membranes by smoothing out the plastic. The membranes were then expose to x-ray film (Kodak X-OMAT AR™ film) and then processed using a film developer.

Table 1A, 1B and 1C shows an extensive list of cytokines, growth factors, soluble receptors, and matrix proteases secreted by human ABM-SC when sub-cultured in serum-free cell culture media. Media Supernatant Concentrate #1=Advanced DMEM (Gibco™) supplemented with 4 mM L-glutamine. Media Supernatant Concentrate #2=RPMI-1640 containing 4 mM L-glutamine and HEPES (HyClone) supplemented with Insulin-Transferrin-Selenium-A (Gibco™).

The results demonstrate that numerous trophic factors and soluble receptors important for tissue regeneration and modulation of the immune system are produced by ABM-SC when cultured under these conditions. Notably, earlier experiments demonstrated that supplementation of the base culture medium with insulin, transferrin, and selenium was required to achieve secreted protein levels such as those indicated in Table 1A, 1B and 1C. Protein levels shown in Table 1A, 1B and 1C were assessed using a RAYBIO™ Human Cytokine Antibody Array (RayBiotech, Inc.). Values are expressed as mean optical densities (O.D.). (N=2 for test samples. N=4 for controls.) Values reported with a (+) indicate mean O.D. values for that particular analyte greater than two standard deviations above the mean O.D. values for the respective negative control. Values reported with a (−) represent mean O.D. values for that particular analyte that are not greater than two standard deviations above the mean O.D. values for the respective negative control.

TABLE 1A

| Cytokine | Media Supernatant Concentrate #1 | Media Supernatant Concentrate #2 |
|---|---|---|
| POSITIVE CTL | 11,020 (Mean O.D.) | 11,127 (Mean O.D.) |
| NEG CTL (Background) | 2,360.00 | 2,271.00 |
| Angiogenin | 5800.5 (+) | 4651 (+) |
| BDNF | 5855.5 (+) | 3587 (+) |
| BLC | 3852 (+) | 3164.5 (+) |
| BMP-4 | 3299 (+) | 2610 (+) |
| BMP-6 | 2359.5 (−) | 2290.5 (−) |
| CK beta 8-1 | 2408.5 (−) | 2426 (−) |
| CNTF | 2655.5 (+) | 2663 (+) |
| EGF | 3932.5 (+) | 2517 (+) |
| Eotaxin | 2527 (+) | 2488 (+) |
| Eotaxin-2 | 2467 (−) | 2452.5 (+) |
| Eotaxin-3 | 4564 (+) | 4450 (+) |
| FGF-6 | 2863.5 (+) | 2883.5 (+) |
| FGF-7 | 2328 (−) | 2374.5 (−) |
| Flt-3 Ligand | 2661 (+) | 2414.5 (−) |
| Fractalkine | 2432.5 (−) | 2379.5 (−) |
| GCP-2 | 2546.5 (+) | 2270 (−) |
| GDNF | 2299.5 (−) | 2208.5 (−) |
| GM-CSF | 2294 (−) | 2129 (−) |
| I-309 | 2431.5 (−) | 2222 (−) |
| IFN-gamma | 2807.5 (+) | 2848.5 (+) |
| IGFBP-1 | 3192 (+) | 4528.5 (+) |
| IGFBP-2 | 4813.5 (+) | 4244 (+) |
| IGFBP-4 | 4640 (+) | 4222.5 (+) |
| IGF-I | 2206.5 (−) | 2238 (−) |
| IL-10 | 2225.5 (−) | 2200.5 (−) |
| IL-13 | 2582 (+) | 2473 (+) |
| IL-15 | 2472.5 (−) | 2622.5 (+) |
| IL-16 | 2339.5 (−) | 2229.5 (−) |
| IL-1alpha | 2698.5 (+) | 2571.5 (+) |
| IL-1beta | 2276 (−) | 2253 (−) |
| IL-1ra | 2609 (+) | 2505.5 (+) |

TABLE 1A-continued

| Cytokine | Media Supernatent Concentrate #1 | Media Supernatent Concentrate #2 |
|---|---|---|
| IL-2 | 2523.5 (+) | 2381 (−) |
| IL-3 | 2346 (−) | 2270 (−) |
| IL-4 | 2591 (+) | 2402 (+) |
| IL-5 | 3159 (+) | 3808 (+) |
| IL-6 | 45570 (+) | 40260 (+) |
| IL-7 | 7336.5 (+) | 5805 (+) |
| Leptin | 4187 (+) | 3733.5 (+) |
| LIGHT | 3689.5 (+) | 3378.5 (+) |
| MCP-1 | 9925.5 (+) | 5561 (+) |
| MCP-2 | 3117.5 (+) | 2481.5 (+) |
| MCP-3 | 2532 (+) | 2382 (−) |
| MCP-4 | 2702.5 (+) | 2694 (+) |
| M-CSF | 2387 (−) | 2381.5 (−) |
| MDC | 2414.5 (−) | 2510.5 (+) |
| MIG | 2344 (−) | 2342.5 (−) |
| MIP-1-delta | 2324 (−) | 2259.5 (−) |
| MIP-3-alpha | 2323.5 (−) | 2261.5 (−) |
| NAP-2 | 2517.5 (+) | 2467.5 (+) |
| NT-3 | 2973.5 (+) | 3205.5 (+) |
| PARC | 2668 (+) | 2630 (+) |
| PDGF-BB | 2580.5 (+) | 2780 (+) |
| RANTES | 2803 (+) | 2760 (+) |
| SCF | 2765 (+) | 2701.5 (+) |
| SDF-1 | 3721 (+) | 2562 (+) |
| TARC | 2488 (−) | 2395 (−) |
| TGF-beta 1 | 2381 (−) | 2311 (−) |
| TGF-beta 3 | 2422 (−) | 2531 (+) |
| TNF-alpha | 2243 (−) | 2321 (−) |
| TNF-beta | 2355 (−) | 2410.5 (−) |

TABLE 1B

| Cytokine | Media Supernatent Concentrate #1 | Media Supernatent Concentrate #2 |
|---|---|---|
| POSITIVE CTL | 12,318 (Mean O.D.) | 11,936 (Mean O.D.) |
| NEG CTL | 2,452.00 | 2,392.00 |
| Acrp30 | 2539.5 (+) | 2436.5 (−) |
| AgRP | 2670 (+) | 2494 (−) |
| Angiopoietin-2 | 3372 (+) | 2656.5 (+) |
| Amphiregulin | 2692 (+) | 2447 (−) |
| axl | 3398.5 (+) | 3438.5 (+) |
| bFGF | 2915 (+) | 2901.5 (+) |
| Beta-NGF | 2573.5 (+) | 2544 (+) |
| BTC | 2653.5 (+) | 2554.5 (+) |
| CCL28 | 2706.5 (+) | 2553.5 (+) |
| CTACK | 3502 (+) | 3217 (+) |
| dtk | 2610.5 (+) | 2512 (+) |
| EGF-R | 3057.5 (+) | 2767.5 (+) |
| ENA-78 | 2630.5 (+) | 2503 (+) |
| Fas/TNFRSF6 | 3312 (+) | 3322.5 (+) |
| FGF-4 | 2711 (+) | 2650.5 (+) |
| FGF-9 | 2770 (+) | 2538.5 (+) |
| G-CSF | 3950.5 (+) | 3951 (+) |
| GITR ligand | 2973.5 (+) | 3107.5 (+) |
| GITR | 3198 (+) | 2935 (+) |
| GRO | 29446.5 (+) | 10214 (+) |
| GRO-alpha | 7351 (+) | 3553.5 (+) |
| HCC-4 | 3241 (+) | 2720.5 (+) |
| HGF | 5535 (+) | 3936.5 (+) |
| ICAM-1 | 3043 (+) | 2701.5 (+) |
| ICAM-3 | 2621.5 (+) | 2427 (−) |
| IGF-BP-3 | 3392 (+) | 3190.5 (+) |
| IGF-BP-6 | 5858 (+) | 6111 (+) |
| IGF-I SR | 2737.5 (+) | 2757 (+) |
| IL-1 R4/ST2 | 3463.5 (+) | 3235.5 (+) |
| IL-1 RI | 2522.5 (+) | 2401 (−) |
| IL11 | 2444.5 (−) | 2273 (−) |
| IL12-p40 | 2584 (+) | 2536 (+) |
| IL12-p70 | 2612 (+) | 2618 (+) |
| IL17 | 2610.5 (+) | 2555.5 (+) |
| IL-2 Ra | 2491 (−) | 2441.5 (−) |
| IL-6 R | 3202 (+) | 2836 (+) |
| IL8 | 24199.5 (+) | 17594.5 (+) |

TABLE 1B-continued

| Cytokine | Media Supernatent Concentrate #1 | Media Supernatent Concentrate #2 |
|---|---|---|
| I-TAC | 3898 (+) | 3564 (+) |
| Lymphotactin | 3415.5 (+) | 3166 (+) |
| MIF | 3743 (+) | 3524 (+) |
| MIP-1-alpha | 2792 (+) | 2747.5 (+) |
| MIP-1-beta | 2638.5 (+) | 2523 (+) |
| MIP-3-beta | 2495.5 (−) | 2377 (−) |
| MSP-a | 2524.5 (+) | 2394 (−) |
| NT-4 | 2735 (+) | 2635 (+) |
| Osteoprotegerin | 4183.5 (+) | 3399 (+) |
| Oncostatin M | 2610 (+) | 2508 (+) |
| PlGF | 2705 (+) | 2493 (−) |
| sgp130 | 3232 (+) | 2866.5 (+) |
| sTNF RII | 3124 (+) | 3127 (+) |
| sTNF-RI | 9981 (+) | 7929.5 (+) |
| TECK | 2887.5 (+) | 2851 (+) |
| TIMP-1 | 8718 (+) | 9342.5 (+) |
| TIMP-2 | 11927 (+) | 12602 (+) |
| TPO | 3712 (+) | 3141.5 (+) |
| TRAIL-R3 | 3129 (+) | 3051 (+) |
| TRAIL-R4 | 3417 (+) | 3381 (+) |
| uPAR | 9557.5 (+) | 8158.5 (+) |
| VEGF | 8587.5 (+) | 6851 (+) |
| VEGF-D | 3477 (+) | 3190.5 (+) |

TABLE 1C

| Cytokine | Media Supernatent Concentrate #1 | Media Supernatent Concentrate #2 |
|---|---|---|
| POS | 16,092 (Mean O.D.) | 15,396 (Mean O.D.) |
| NEG | 2,338 | 1,747 |
| Avtivin A | 23239.5 (+) | 18339 (+) |
| ALCAM | 14185.5 (+) | 15463.5 (+) |
| B7-1 (CD80) | 2983.5 (+) | 2222.5 (+) |
| BMP-5 | 2770.5 (+) | 2011.5 (+) |
| BMP-7 | 2564 (+) | 1828 (−) |
| Cardiotrophin-1 | 2816.5 (+) | 2097 (+) |
| CD14 | 3556 (+) | 2334.5 (+) |
| CXCL-16 | 4108.5 (+) | 2559 (+) |
| DR6 (TNFRSF21) | 3477 (+) | 2312 (+) |
| Endoglin | 3070 (+) | 2135 (+) |
| ErbB3 | 3366 (+) | 2313.5 (+) |
| E-Selectin | 2846.5 (+) | 1918 (+) |
| Fas-Ligand | 3531 (+) | 2943.5 (+) |
| ICAM-2 | 3158.5 (+) | 2155.5 (+) |
| IGF-II | 3212 (+) | 2395.5 (+) |
| IL-1 R II | 2855 (+) | 1834 (−) |
| IL-10 Rb | 2780 (+) | 1916 (+) |
| IL-13 Ra2 | 2559.5 (+) | 1693 (+) |
| IL-18 BPa | 2921 (+) | 1881 (−) |
| IL-18 Rb | 3238.5 (+) | 2387 (+) |
| IL-2 Ra | 3666 (+) | 2316.5 (+) |
| IL-2 Rb | 3001 (+) | 2083.5 (+) |
| IL-2 Rg | 3121 (+) | 2185.5 (+) |
| IL-21R | 3567.5 (+) | 2534.5 (+) |
| IL-5 Ra | 3084.5 (+) | 2237 (+) |
| IL-9 | 3676 (+) | 2324.5 (+) |
| IP-10 | 3300.5 (+) | 2262.5 (+) |
| LAP | 6202 (+) | 5383.5 (+) |
| Leptin R | 3487 (+) | 2791 (+) |
| LIF | 3486.5 (+) | 2400.5 (+) |
| L-Selectin | 3036.5 (+) | 2160 (+) |
| M-CSF R | 3140 (+) | 2330.5 (+) |
| MMP-1 | 3469 (+) | 2499 (+) |
| MMP-13 | 3083.5 (+) | 2316.5 (+) |
| MMP-9 | 3058.5 (+) | 2370 (+) |
| MPIF-1 | 2974 (+) | 2274.5 (+) |
| NGF R | 2887.5 (+) | 2355 (+) |
| PDGF-AA | 4130 (+) | 3423.5 (+) |
| PDGF-AB | 3191.5 (+) | 2278.5 (+) |
| PDGF Ra | 4430 (+) | 4027 (+) |
| PDGF Rb | 3768 (+) | 2784 (+) |
| PECAM-1 | 4071.5 (+) | 3450 (+) |
| Prolactin | 3199.5 (+) | 2151 (+) |

TABLE 1C-continued

| Cytokine | Media Supernatent Concentrate #1 | Media Supernatent Concentrate #2 |
|---|---|---|
| SCF R | 3431.5 (+) | 2668.5 (+) |
| SDF-1b | 2268.5 (−) | 2156 (+) |
| Siglec-5 | 2691 (+) | 2160.5 (+) |
| TGF-a | 3058.5 (+) | 2388.5 (+) |
| TGF b2 | 3316 (+) | 2583 (+) |
| Tie-1 | 2883 (+) | 3178 (+) |
| Tie-2 | 3565 (+) | 3802.5 (+) |
| TIMP-4 | 6468 (+) | 6248 (+) |
| VE-Cadherin | 3164.5 (+) | 2428 (+) |
| VEGF R2 | 4030.5 (+) | 3003 (+) |
| VEGF R3 | 3200 (+) | 2651.5 (+) |

Example 4

Figure 2:
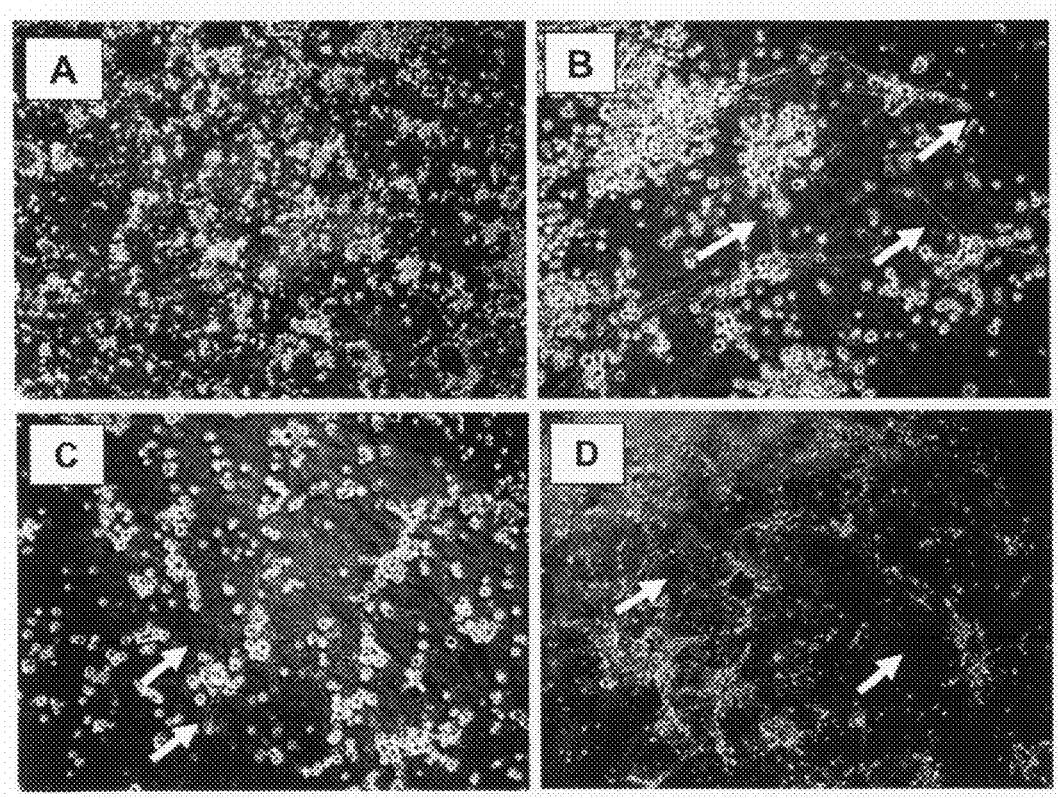
FIG. 2 shows photomicrographs of PC-12 differentiation into neurons using nerve growth factor (NGF) and conditioned media derived from human exABM-SC (at about 43 population doublings). A) RPMI-ITS medium only. B) RPMI-ITS supplemented with NGF. C) RPMI-ITS supplemented with a 1:50 dilution of concentrated control media and NGF. D) RPMI-ITS supplemented with a 1:50 dilution of concentrated conditioned media derived from human ABM-SC and NGF. Arrows indicate neurite outgrowth. Extent of neurite outgrowth in panel D is significantly more robust than that of panel B and C.

Bioactivity of Adult Bone Marrow-Derived Somatic Cells: In Vitro Neurogenesis Enhanced by Secreted Factors A stock solution of collagen was first prepared by re-suspending rat tail collagen (Sigma Chemical) in 0.1N acetic acid at a final concentration of 3.0 mg/mL. The collagen-based medium then was prepared as described by Bell et al., Proc. Natl. Acad. Sci. USA, vol. 76, no. 3, pp. 1274-1278 (March 1979) with minor modifications as described herein. Briefly, the collagen medium was prepared by mixing the rat tail collagen solution with DMEM 5× (JRH Biosciences) supplemented with 5 mM L-glutamine (CELLGRO™), Anti-biotic-Antimycotic Solution (CELLGRO™), and a buffer solution (0.05N NaOH (Sigma Chemical), 2.2% NaHCO$_3$ (Sigma Chemical), and 60 mM HEPES (JRH Biosciences) at a ratio of 4.7:2.0:3.3. Approximately 500 microL of the collagen cell suspension was added to each well of a 24-well culture plate. The 24-well plates were then placed in a 37° C. humidified trigas incubator (4% O$_2$, 5% CO$_2$, balanced with nitrogen) for 1 hour to permit the collagen solution to congeal. Frozen rat PC-12 were thawed, washed in RPMI-1640 supplemented with 4 mM L-glutamine and HEPES (HY-CLONE™) supplemented with Insulin-Transferrin-Selenium-A (GIBCO™) and centrifuged at 350×g for 5 minutes at 25° C. Cell pellets were re-suspended in same solution at a concentration of 75,000 viable cells/mL, with and without 136 ng/mL rat beta-NGF (β-NGF) (Sigma Chemical), 1:50 dilution of unconditioned concentrated RPMI-1640/ITS medium (used as a negative control), and a 1:50 dilution of conditioned concentrated RPMI-1640/Insulin-Transferrin-Selenium-A (ITS) media (media was conditioned as described in Example 1; conditioned and unconditioned, negative control media were concentrated as described in Example 1). Next, 1 mL of cell suspension was dispensed evenly across the surface of each of 2 gels (1 mL gel) for each cohort and then verified by phase contrast microscopy. The plates were then placed in a 37° C. humidified trigas incubator (4% O$_2$, 5% CO$_2$, balanced with nitrogen). Spent culture media was replaced every 3 days with fresh media. Images were captured on Day 10. See, FIG. 2.

These results demonstrate that PC12 differentiation into neurons by NGF is augmented dramatically when supplemented with conditioned media produced by human ABM-SC. Interestingly, the extent of neural differentiation, as assessed by the number of axon and neurites in the culture, was not significant when conditioned media was added alone. While some neurite outgrowth was observed in the presence of NGF alone, supplementing the cultures with conditioned media dramatically increased both the number and length of neurites. Previous work in our lab showed that supplementing RPMI culture media with insulin, transferrin, and selenium was critical for neural differentiation of PC12 under all standard published experimental conditions tested. These data indicate that media conditioned by human ABM-SC contain components which supplement or induce neurite outgrowth over and above the levels obtained with RPMI/ITS media alone or with RPMI/ITS media containing NGF. See, FIG. 2.

Example 5

Figure 3:
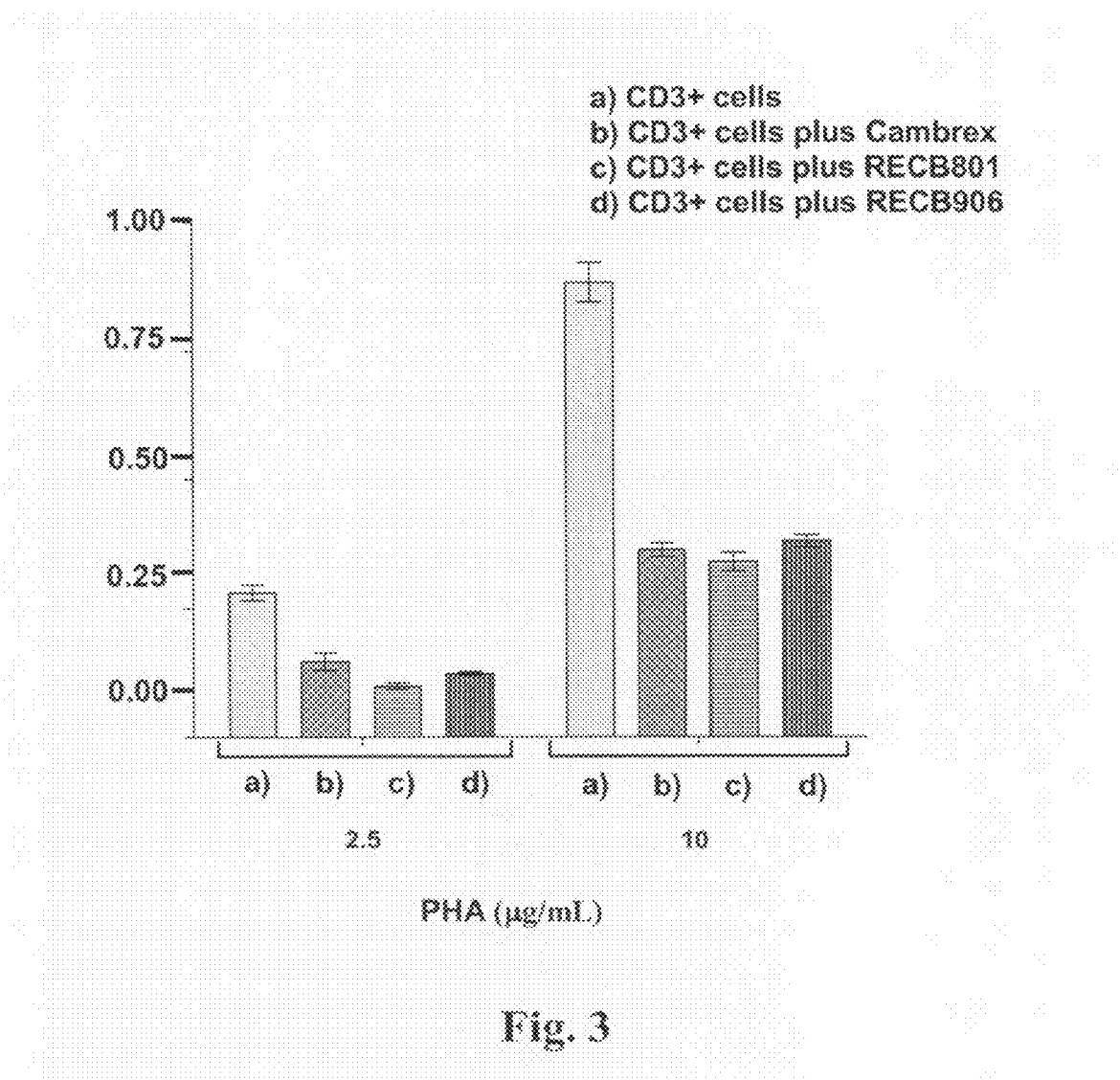
FIG. 3 is a graphical representation of inhibition of mitogen-induced T cell proliferation using human ABM-SC. Lot #RECB801 represents ABM-SC that have been sub-cultured to about 19 population doublings and Lot #RECB906 represents exABM-SC which have been sub-cultured to about 43 population doublings. To stimulate T cell proliferation, cultures were inoculated with 2.5 or 10 microg/mL Phytohaemagglutinin. Cells were then harvested after 72 hrs later and stained with CD3-PC7 antibody. Human mesenchymal stem cells were used as a positive control. (Human mesenchymal stem cells were obtained from Cambrex Research Bioproducts; now owned by Lonza Group Ltd., Basel, Switzerland).

Bioactivity of Adult Bone Marrow-Derived Somatic Cells: Inhibition of Mitogen-Induced T Cell Proliferation In Vitro Human ABM-SC (Lot #RECB801 at ~18 population doublings) and exABM-SC (RECB906 at ~43 population doublings), were plated in 75 cm$^2$ flasks at a concentration of 6000 viable cells/cm$^2$ in complete media (Minimal Essential Medium-Alpha (HYCLONE™) supplemented with 4 mM glutamine and 10% sera-lot selected, gamma-irradiated, fetal bovine serum (HYCLONE™) and incubated at 37° C. in a humidified trigas incubator (4% O$_2$, 5% CO$_2$, balanced with nitrogen). After 24 hrs, spent media was aspirated and replaced with 15 mL fresh media. Human mesenchymal stem cells (hMSC, Catalog #PT2501, Lot #6F3837; obtained from Cambrex Research Bioproducts; now owned by Lonza Group Ltd., Basel, Switzerland) were plated in 75 cm$^2$ flasks at a concentration of 6000 viable cells/cm$^2$ in 15 mL Mesenchymal Stem Cell Growth Medium (MSCGM™; Lonza Group Ltd., Basel, Switzerland) and incubated at 37° C. in a humidified incubator at atmospheric O$_2$ and 5% CO$_2$. After 24 hrs, spent media was aspirated and replaced with 15 mL fresh MSCGM™. Both human ABM-SC (hABM-SC) and hMSC were harvested after 96 hours in culture. Harvested hABM-SC and hMSC were plated in 96-well round bottom plates at a concentration of 25,000 viable cells/mL in RPMI-complete media (HYCLONE™). Human peripheral blood mononuclear cells (PBMCs) were labeled in 1.25 microM CarboxyFluoroscein Succinimidyl Ester (CFSE) and cultured at 250,000 cells/well in RPMI-complete media along with hMSC, Lot #RECB801, Lot #RECB906 hABM-SC or alone. To stimulate T cell proliferation, cultures were inoculated with 2.5 or 10 microg/mL Phytohaemagglutinin (Sigma Chemical). Cells were then harvested 72 hrs later and stained with CD3-PC7 antibody (Beckman Coulter), as per manufacturer's instructions, and analyzed on a Beckman FC 500 Cytometer, using FlowJo 8.0 software (Tree Star, Inc., Ashland, Oreg.). Only CD3+ cells were analyzed for division index. See, FIG. 3.

These findings demonstrate that exABM-SC possess the capacity to inhibit T cell activation and proliferation and, therefore, may be useful as a therapeutic to suppress T cell-mediated graft rejection, autoimmune disorders involving dysregulation of T cells, or to induce a state of immune tolerance to an otherwise immunogenic skin product. Thus, one could envision the use of allogeneic human exABM-SC or compositions produced by such cells, to treat burn patients awaiting surgical application of an allogeneic skin product. In such an embodiment, treating an open wound first with exABM-SC, or compositions produced by such cells, may act not only to help rebuild the wound bed by inciting host cells to migrate to the cite of injury, but also to provide an environment permissive to long term engraftment of allogeneic skin or skin substitutes.

Example 6

Reconstitution of Porcine ABM-SC in Aqueous Vehicle for In Vivo Administration Porcine ABM-SC were seeded at 60 cells/cm², referred at day 4, and grown for a total of 6 days. Cells were collected and frozen until subsequent use. Frozen aliquots of porcine ABM-SC were thawed, washed in DPBSG (Dulbecco's Phosphate Buffered Saline (CELLGRO™)) supplemented with 4.5% glucose) and centrifuged at 350×g for 5 minutes at 25° C. Cell pellets were re-suspended in DPBSG at a concentration of approximately 50,000/microL. Cell counts and viability assays were performed using a COULTER™ AcT 10 Series Analyzer (Beckman Coulter, Fullerton, Calif.) and by trypan blue exclusion, respectively. The cell suspension was then loaded into a 1 cc tuberculin syringe.

Example 7

Bioactivity of Adult Bone Marrow-Derived Somatic Cells: Treatment of Incisional Wounds with Allogeneic Porcine ABM-SC Two Yucatan swine, weighing between 57 kg and 78 kg were anesthetized and prepared for aseptic surgery. Four incisional wounds measuring approximately 50 mm in length were made with a scalpel blade on both sides of two animals (Nos. 3 and 4) for a total of eight wounds per animal along the paravertebral and thoracic area skin. Bleeding was stopped by inserting sterile gauze soaked with epinephrine into the lesion site. Gauze was then removed after about 10-20 minutes and each wound was treated with a single dose of porcine ABM-SC, divided into 12 separate injections evenly spaced around the incision with an additional 10-300 microL applied to the wound bed itself. Control wounds were injected similarly with vehicle only (DPBSG). Wounds were then closed with Steri-Strips™ (3M) and the animals were covered with protective aluminum jackets. The jackets were checked several times each day to ensure stable and proper position. The wound dressings were monitored daily and changes photographed on days 0, 1, 3, 5, and 7. Animals were euthanized on day 7 for histopathology. Formalin fixed paraffin embedded tissue sections were prepared and stained by H&E. Histomorphometric scoring was conducted by an expert veterinary pathologist blinded to the treatment group.

Figure 4:
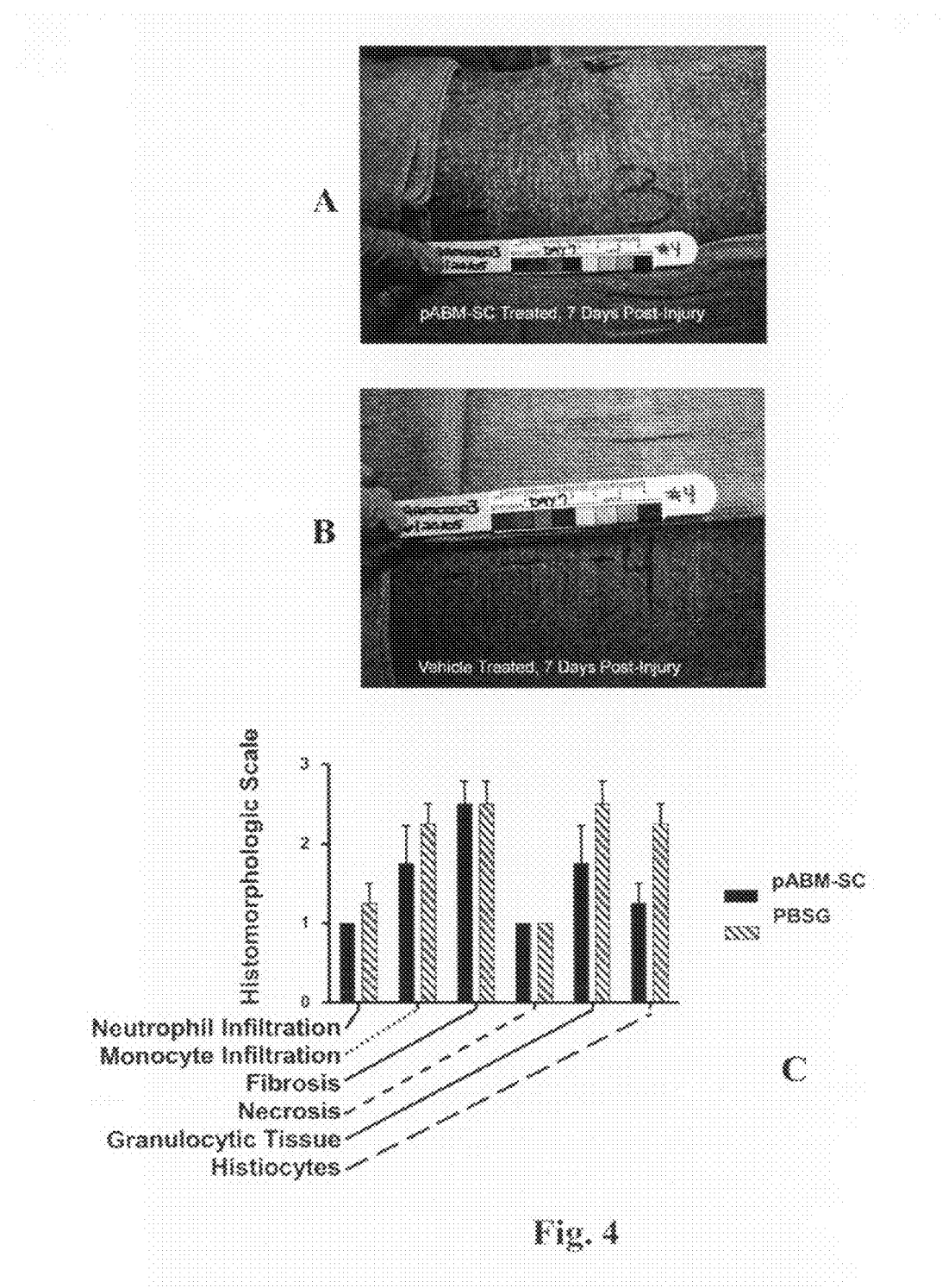
FIG. 4 shows photomicrographs of pig skin 7 days after surgically-induced incisional wounding (left two panels, both wounds from experimental group #4). A) Wound No. 3 treated with allogeneic porcine ABM-SC (at about 28 population doublings) shows complete wound closure with virtually no scar. B) In comparison, Wound No. 4 treated with vehicle only reveals a visible scar. C) The graph (right panel) represents histomorphometric scoring of tissue sections from both treatment groups and shows a statistically significant reduction (p=0.03) in the number of histiocytes in the porcine ABM-SC treated wounds (statistical significance determined using a two-tailed unpaired T-test); compare, bars for "Histiocytes" PBSG versus pABM-SC treated.

Seven days following treatment of the wounds, lesions treated with allogeneic porcine ABM-SC shown almost no signs of visible scarring (FIG. 4) while those treated with vehicle exhibited visible signs of scarring. Histomorphometric analysis of the wounds showed a marked reduction in tissue macrophages (histiocytes) in those treated with the ABM-SC, while no significant difference was seen in any of the other histological scores assessed.

Figure 5:
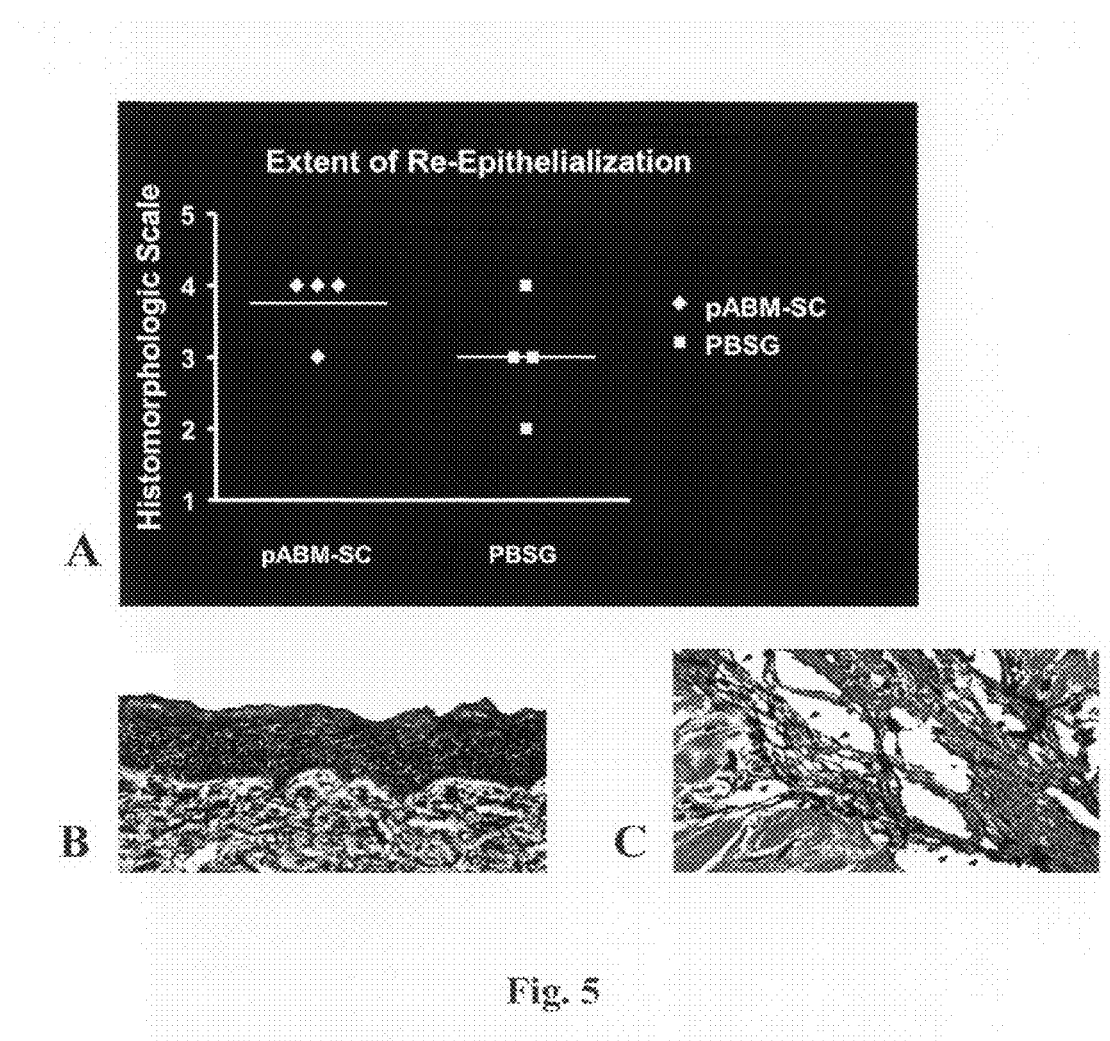
FIG. 5 is a graphical representation (top panel) of the extent of re-epithelialization across the incisional wounds 7 days post-treatment. Wounds treated with porcine ABM-SC (at about 28 population doublings) had a thicker epidermis than those treated with vehicle only. The photomicrograph in the lower left panel shows (histologically) complete and anatomically correct repair of the epidermis in the wounds treated with porcine ABM-SC. The photomicrograph in the lower right panel shows (histologically) porcine ABM-SC (arrow heads) which appear engrafted, at least transiently, in the hypodermis at this 7 day time point.

When similar tissue sections were scored for the extent of re-epithelialization (a crude indicator wound healing rate), those treated with ABM-SC exhibited a marked increase in the amount of epithelial cells repopulating the site of the incisions (FIG. 5).

Example 8

Bioactivity of Human ABM-SC in Collagen Vehicle for In Vivo Administration as a Liquid, Semi-Solid, or Solid-Like Therapeutic (FIG. 6-9)

Figure 6:
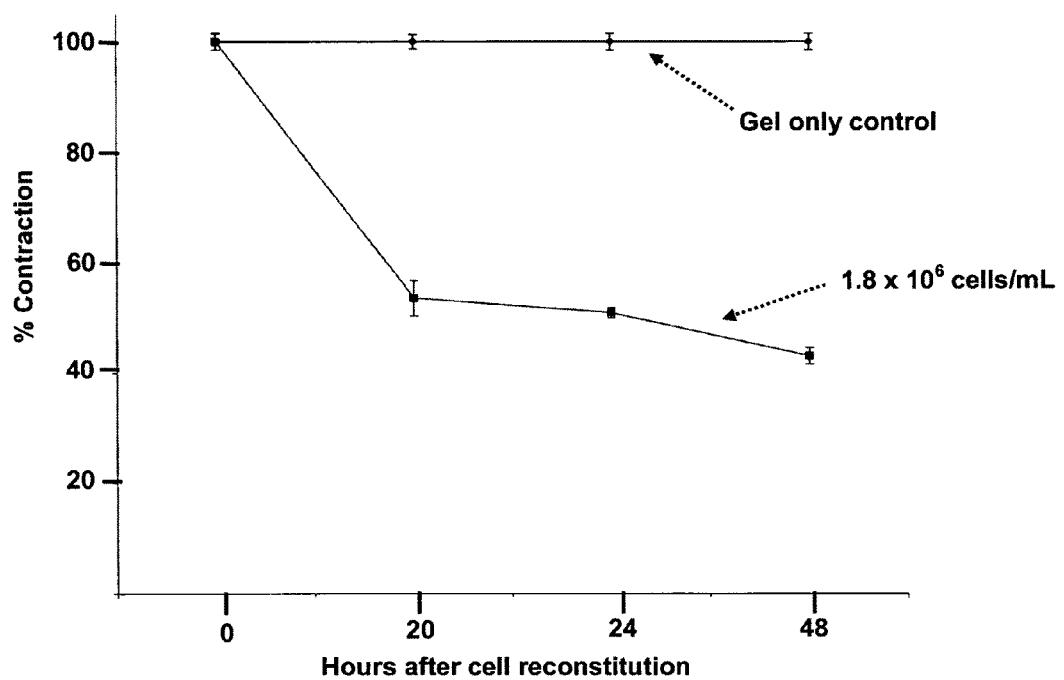
FIG. 6 is a graphical representation of ABM-SC mediated contraction of hydrated collagen gel lattices seeded 24 hours after cell reconstitution. Human ABM-SC (at about 27 population doublings) were reconstituted in liquid biodegradable collagen-based media (at $1.8 \times 10^6$ cells/mL) and then stored for 24 hours at approximately 4-8° C. The following day the liquid cell suspension was placed into a culture dish to form a semi-solid collagen lattice. The semi-solid collagen lattices were maintained in a cell culture incubator to facilitate contraction over the course of three days. Collagen lattices prepared without cells did not contract, demonstrating that contraction is dependent upon the presence of cells.

When reconstituted in a collagen-based biodegradable vehicle and stored at 4° C., human ABM-SC (Lot #PCH610; ~27 population doublings) retain high cell viability for at least 24 hours (as demonstrated by cell bioactivity in gel contraction assays). Stored this way, the collagen solution will remain as a liquid and will preserve the cells in a suspended state without significant loss of viability (FIG. 6). Bioactivity of the cells can then be assessed using an in vivo assay of wound repair. To conduct this assay, a stock solution of collagen was first prepared by re-suspending rat tail collagen (Sigma Chemical) in 0.1N acetic acid at a final concentration of 3.0 mg/mL. The collagen medium was prepared as described by Bell et al. (Proc. Natl. Acad. Sci. USA, vol. 76, no. 3, pp. 1274-1278 (March 1979)) with minor modifications as described herein. Briefly, the collagen medium was prepared by mixing the rat tail collagen solution with DMEM 5× (JRH Biosciences) supplemented with 5 mM L-glutamine (CELLGRO™), Antibiotic-Antimycotic Solution (CELLGRO™; Catalog #30-004-C1), and a buffer solution (0.05N NaOH (Sigma Chemical), 2.2% NaHCO$_3$ (Sigma Chemical), and 60 mM HEPES (JRH Biosciences) at a ratio of 4.7:2.0:3.3. Frozen human adult bone marrow derived somatic cells (hABM-SC) were thawed, washed in DMEM 1× and centrifuged at 350×g for 5 minutes at 25° C. The cell pellets were re-suspended in DMEM 1× at concentration of approximately 72,000 total cells/microL. Fifty microliters of cell suspension was then added to 2 mL collagen medium and gently triturated (i.e., gently pipetted up and down to obtain a homogeneous suspension of cells in collagen medium), yielding a final cell concentration of approximately 1,800 cells/microL. The cell suspension was then stored at approximately 4-8° C. overnight. The following day, the liquid cell suspension was transferred from the 15 mL conical tube and dispensed into 24-well cell culture plates at approximately 500 microL/well. The plates were then placed in a 37° C. humidified trigas incubator (4% O$_2$, 5% CO$_2$, balanced with nitrogen) for 1 hour to permit the collagen to solidify into a semi-solid gel. The gels were then removed from the 24-well plates using disposable sterile spatulas (VWR) and transferred to 12-well culture plates. The gels were then floated in 1.0 mL DMEM 1× per well. For negative controls, gels were prepared as described but without cells. Three wells were seeded for each condition (n=3).

Figure 7:
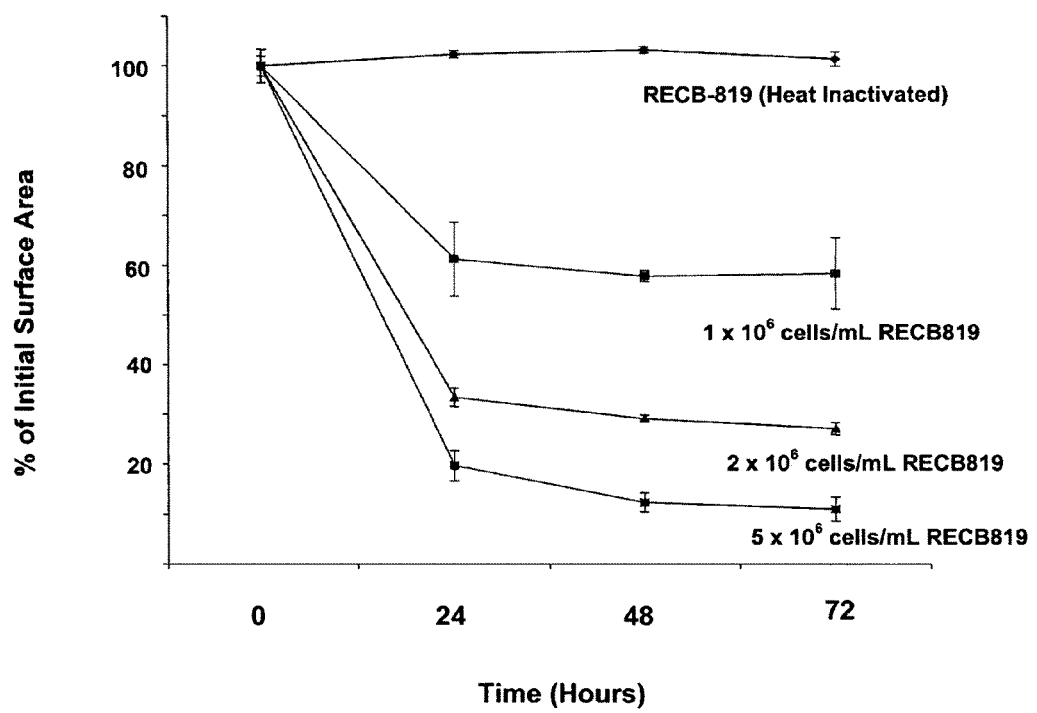
FIG. 7 is a graphical representation of ABM-SC mediated contraction of hydrated collagen gel lattices seeded at different cell concentrations utilizing exABM-SC at about 43 population doublings. The data demonstrate that rate and absolute magnitude of contraction is related to cell number. Heat inactivated cells do not contract the gels, demonstrating that this activity is a biophysical event.

To evaluate the extent to which gel contraction is dose-dependent, a similar assay was conducted wherein human exABM-SC (Lot#RECB819; at ~43 population doublings) were reconstituted in collagen solution at different cell concentrations immediately after removal from cryostorage (FIG. 7). A stock solution of collagen was first prepared by re-suspending rat tail collagen (Sigma Chemical) in 0.1N acetic acid at a final concentration of 3.0 mg/mL. The collagen medium then was prepared as described by Bell et al. (1979) with minor modifications as described herein. Briefly, the collagen medium was prepared by mixing the rat tail collagen solution with DMEM 5× (JRH Biosciences) supplemented with 5 mM L-glutamine (CELLGRO™), Antibiotic-Antimycotic Solution (Cellgro™), and a buffer solution (0.05N NaOH (Sigma Chemical), 2.2% NaHCO$_3$ (Sigma Chemical), and 60 mM HEPES (JRH Biosciences)) at a ratio of 4.7:2.0:3.3. Frozen human adult bone marrow derived somatic cells (hABM-SC) were thawed, washed in DMEM 1× and centrifuged at 350×g for 5 minutes at 25° C. The cell pellets were re-suspended in DMEM 1× at concentration of approximately 40,000, 80,000 and 200,000 viable cells/microL. Fifty microliters of each cell suspension was added to 2 mL collagen medium and gently triturated. Approximately 500 microL of the collagen cell suspension was added to each well of a 24-well culture plate. The plates were then placed in a humidified 37° C. trigas incubator (4% O$_2$, 5% CO$_2$ balanced with nitrogen) for 1 hour to permit the collagen solution to solidify. The gels were then removed from the plates using disposable sterile spatulas (VWR) and transferred to 12-well culture plates. The gels were floated in 1.0 mL DMEM 1× per well.

As a negative control, gels were prepared as described above using the highest concentration of hABM-SC ($5\times10^6$/mL) except that the cells were heat-inactivated (to eliminate biological activity). Heat-inactivated cells were first prepared by heating the initial cell suspension in DMEM 1× medium to 70° C. in a heat block containing water (heat transfer) for 40 minutes. Three wells were seeded for each condition (n=3).

To determine the extent to which the gels contracted over time, the percentage initial or starting surface area was calculated from digital images captured at 0, 24, 48 and 72 hours using a flatbed scanner. From each image, the diameter of the gel was measure both horizontally and vertically and then averaged. Results demonstrate that both the rate and extent of gel contraction was effected in a dose dependent manner (FIG. 7).

Figure 8:
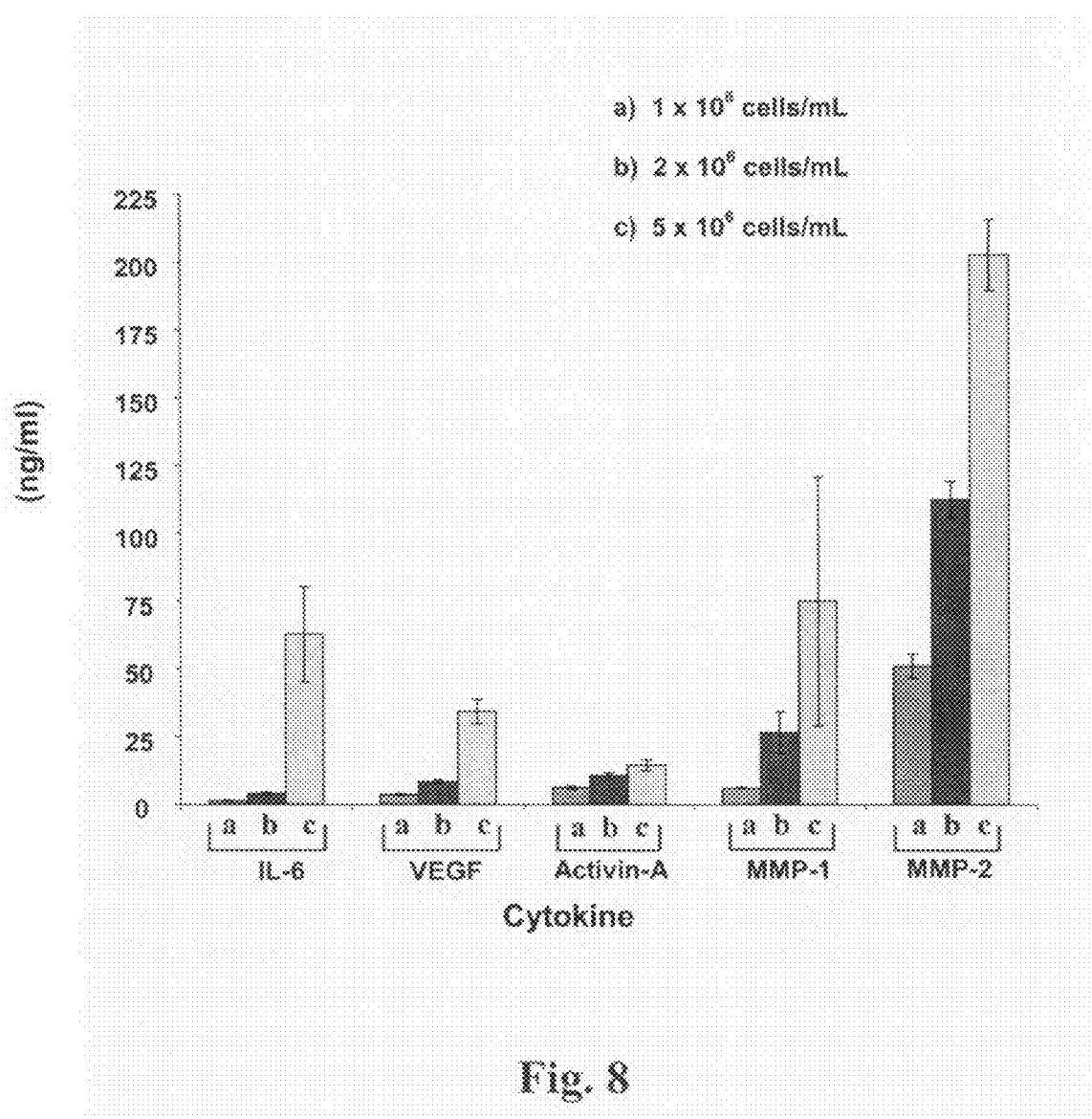
FIG. 8 is a graphical representation of ABM-SC mediated secretion of several cytokines and matrix proteases (i.e., IL-6, VEGF, Activin-A, MMP-1, and MMP-2) when cultured for 3 days in hydrated collagen gel lattices utilizing exABM-SC at about 43 population doublings.

To determine the levels of certain secreted proteins produced from the human ABM-SC in these semi-solid gels, enzyme-linked immunosorbant assay (ELISA) was performed (on day 3 of culture) on conditioned cell culture supernatants collected from the liquid media surrounding the gels (FIG. 8). Supernatants were transferred to sterile 15 mL conical tubes and centrifuged at 1140×g for 15 minutes to remove cell debris. Supernatants were then transferred to 2 mL cryovials and transferred to −80° C. for short-term storage. On the day of assay, supernatants were thawed and equilibrated to room temperature before use. ELISA analysis was performed to detect IL-6, VEGF, Activin-A, pro-MMP-1, and MMP-2 ELISA (conducted as per manufacturer's instructions; all kits were purchased from R&D Systems, Inc. (Minneapolis, Minn., USA)). Results demonstrate that therapeutically relevant levels of trophic factors can be produced by these semi-solid neotissues and that these levels can be controlled by adjusting cell concentration. Of the trophic factors measured, detectable levels were not seen in cultures containing heat inactivated cells only. Statistical comparisons between assay conditions were determined by One-way ANOVA (***$p<0.001$).

Figure 9:
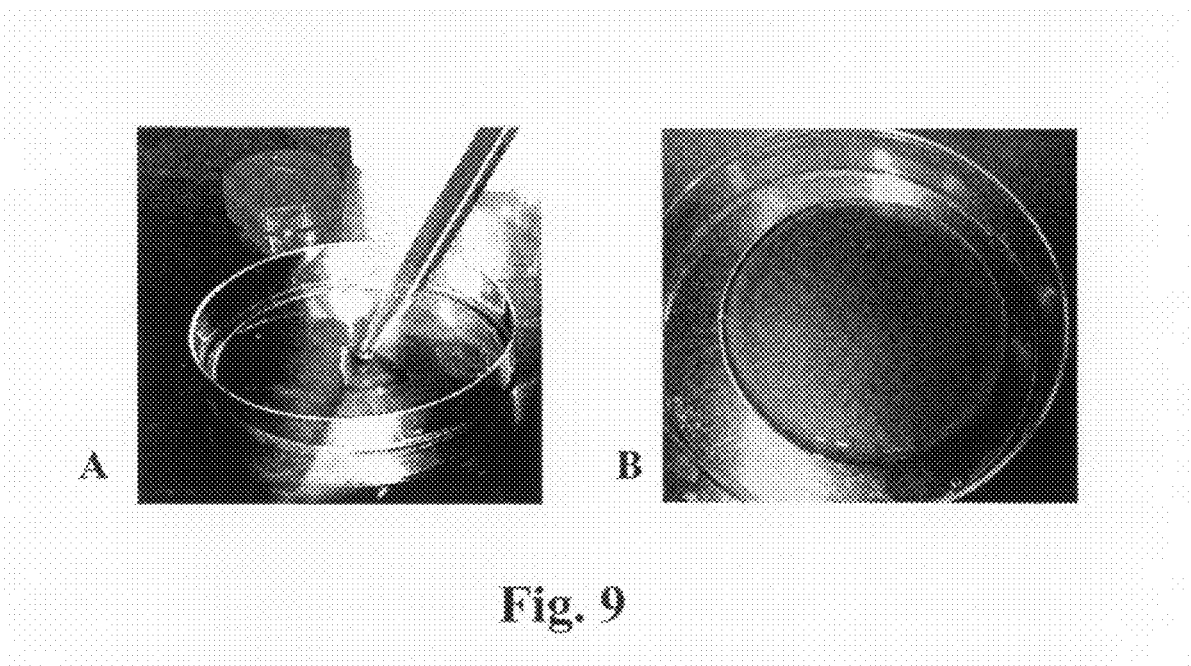
FIG. 9 shows photomicrographs of human ABM-SC reconstituted in biodegradable collagen-based media as a liquid (left panel) or a semi-solid (right panel) (utilizing exABM-SC at about 43 population doublings). When reconstituted using this formulation, the cell suspension can remain as a liquid at 4° C. for more than 24 hrs. When placed in a culture dish and incubated at 37° C., the cell suspension will solidify within 1-2 hours, giving rise to a semi-solid structure than can be physically manipulated.

Human ABM-SC can also be reconstituted in a collagen solution to construct a large-format semi-solid structure that could be used as topical therapeutic (FIG. 9). To construct such a structure, a stock solution of collagen was first prepared by re-suspending rat tail collagen (Sigma Chemical) in 0.1N acetic acid at a final concentration of 3.0 mg/mL. The aqueous collagen medium was prepared by mixing the rat tail collagen solution with DMEM 5× (JRH Biosciences) supplemented with 5 mM L-glutamine (CELLGRO™), Antibiotic-Antimycotic Solution (CELLGRO™), and a buffer solution (0.286N NaOH (Sigma Chemical), 1.1% NaHCO$_3$ (Sigma Chemical), and 100 mM HEPES (JRH Biosciences) at a ratio of 6:2:2. Frozen hABM-SC were thawed and washed in 1×DMEM and then centrifuged at 350×g for 5 minutes at 25° C. The cell pellet was re-suspended in 1×DMEM at a concentration of approximately 90,000 cells/microL. Approximately 1.1 mL of cell suspension was then added to 20 mL collagen medium and gently triturated to achieve a final cell concentration of $5\times10^6$ cells/mL. The final concentration of collagen was 1.8 mg/mL. The cell suspension was then dispensed into a 10 cm Petri dish (forming dish). The effective dose of cells in the collagen solution dispensed was approximately $100\times10^6$ viable cells. The 10 cm forming dish containing the cell suspension was then placed in a humidified 37° C. incubator (5% $CO_2$) for 1 hour to permit the collagen solution to solidify. The semi-solid gel was then carefully removed from the 10 cm forming dish and transferred to a 15 cm Petri dish (culture dish) and photographed.

Figure 10:
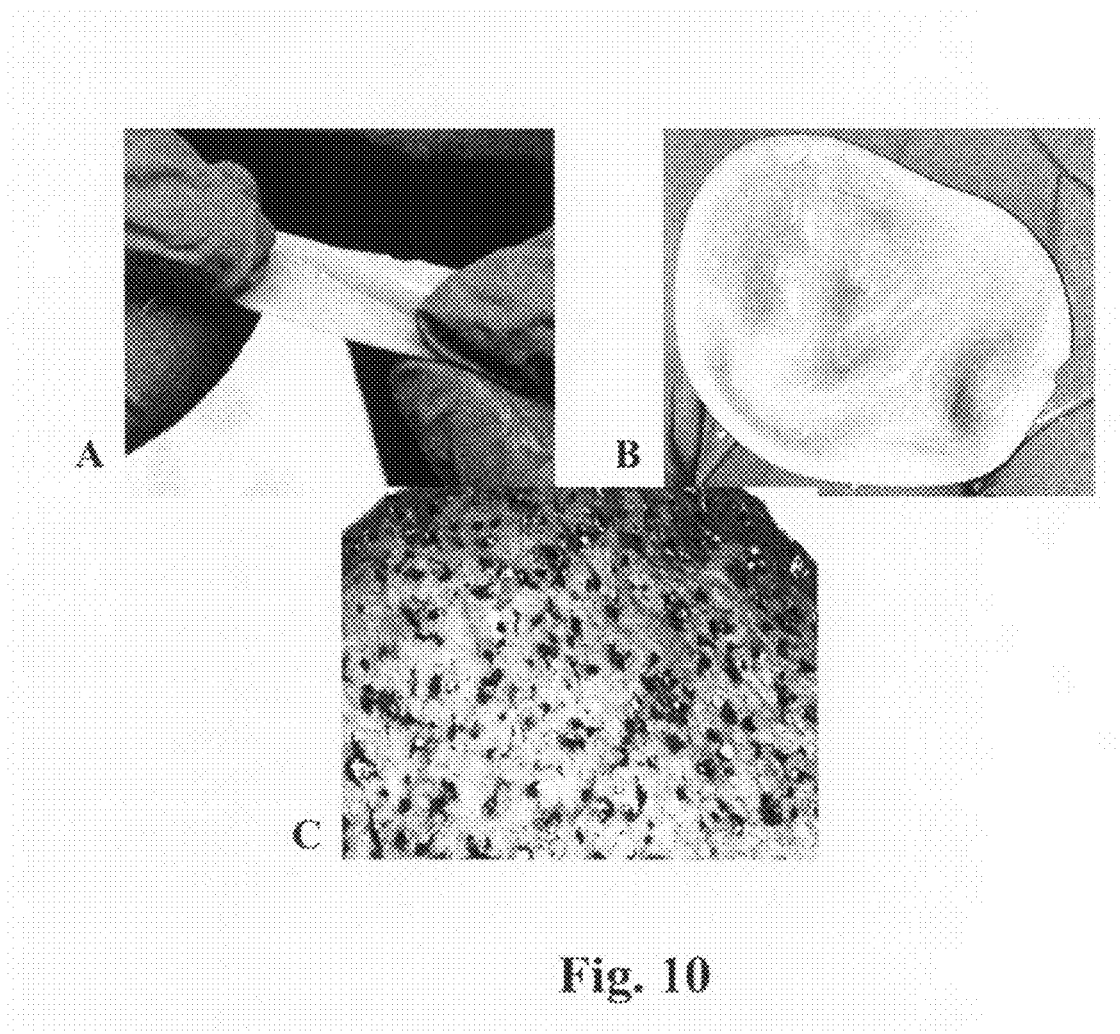
FIG. 10 shows photomicrographs of a solid-like neotissue formed by culturing human ABM-SC (at about 43 population doublings) reconstituted in the biodegradable collagen-based media for three days. The upper left panel shows the pliability of the tissue when stretched. The upper right panel shows the general texture of the solid-like neotissue. The lower panel shows a histological section of the tissue stained by Masson's Trichrome, demonstrating the rich extracellular matrix synthesized by the ABM-SC. Control gels constructed by the same method, but lacking cells, do not stain blue by this method, demonstrating that the collagen and glycosaminoglycan-rich matrix is produced by the cells.

To construct a solid-like neotissue derived from human ABM-SC and collagen, the semi-solid structure described above can be placed back into a 37° C. humidified cell culture incubator (5% $CO_2$) for an additional 2 days (FIG. 10). To form a solid-like neotissue, a semi-solid gel prepared as described above, with the exception that the final collagen solution was 1.4 mg/mL (instead of 1.8 mg/mL), was carefully dislodged from the edges of the 10 cm forming dish and floated in approximately 82 mL 1×DMEM containing Antibiotic-Antimycotic Solution (CELLGRO™) in a 15 cm culture dish. The semi-solid gel was then transferred to a 37° C. humidified incubator (5% $CO_2$) for an additional 48 hrs to facilitate remodeling of the matrix into a solid-like tissue structure, free of the starting collagen substrate. The solid-like neotissue was then removed from the 15 cm culture dish and photographed (FIGS. 10A and 10B). Histological analysis of the neotissue by Masson's Trichrome stain demonstrates that the matrix is rich in newly synthesize human collagens and proteoglycans (FIG. 10C). Control collagen gels do not stain by this method. Collagens and proteoglycans stain blue.

The results of these studies indicate that frozen stocks of ABM-SC can be dispensed upon thaw and reconstituted in a liquid collagen-based medium that could be used therapeutically as a liquid suspension, semi-solid construct, or solid-like neotissue. When prepared in such a way and stored at approximately 4-10° C., the cell suspension will remain as liquid while maintaining satisfactory cell viability for greater than 24 hours. Employing such a method to formulate ABM-SC for clinical application then would provide considerable latitude to the clinician administering the cells. The suspension could be administered as a liquid injectable or, alternatively, could be applied topically to a wound bed. In the latter case, the liquid cell suspension would be anticipated to mold to the contour of the wound and then congeal into a semi-solid structure (for example, when warmed to 37 degrees C.). Alternatively, the suspension could be used in such a way as to manufacture semi-solid constructs or solid-like neotissues.

These data also show that when prepared by the methods, the resulting compositions each possess bioactivity important for mediating repair of various types of wounds, particularly those involving the skin.

ExCF-SC (for example, exABM-SC), or compositions produced by such cells, prepared in a liquid collagen-based medium could therefore be used topically to treat open wounds or as an injectable alternative to dermal fillers for facial rejuvenation.

In the semi-solid form, exCF-SC (for example, exABM-SC) or compositions produced by such cells, cold be used topically to treat severe burn patients that have had damaged full-thickness skin removed surgically, thereby acting as a dermal replacement.

Solid neotissues produced by exCF-SC (for example, exABM-SC) could be used surgically as an alternative to human cadaveric skin (ALLODERM™), porcine skin (PERMACOL™) and other animal-derived constructs (INTEGRA™). Moreover, these data also show that the potency of each of these various constructs can be controlled by altering dose of cells or compositions produced by the cells.

Example 9

Improvement of Cardiac Function in Rats Treated with hABM-SC

Figure 15:
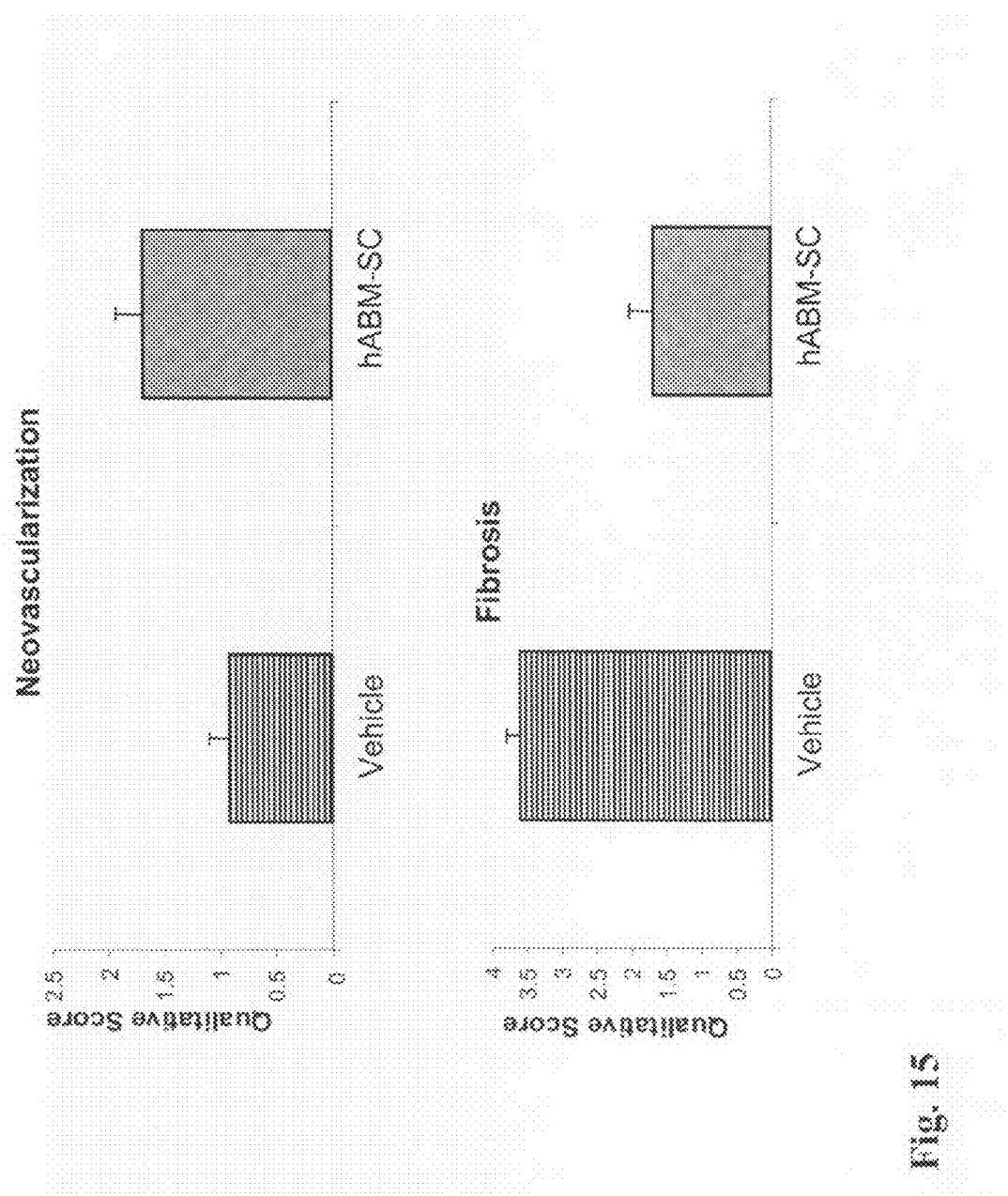
FIG. 15 shows results obtained from histological, performed approximately 30 days after administration of ABM-SC, measurement of changes in the heart structure of rats receiving vehicle or ABM-SC seven days after myocardial infarction.

Administration of human ABM-SC to animals following myocardial infarct demonstrates that CF-SC (such as ABM- SC) improve cardiac function and enhance repair of cardiac tissue damage by stimulating angiogenesis and reducing fibrosis. See, FIG. 15. A rat model for acute myocardial infarction was utilized by occluding a coronary artery thereby creating a cardiac lesion (i.e., damaged region of heart). Lesioned rats were injected intercardially with either hABM-SC or vehicle.

Heart Function Methods: Sprague-Dawley rats of both sexes (age approx. 3 months) received experimentally-induced myocardial infarction via the placement of a permanent silk ligature around the left-anterior descending (LAD) coronary artery via a midline sternotomy. Five days after this procedure, the rats were begun on a standard regimen of Cyclosporine A treatment that lasted for the duration of the study. On day 7-8 following infarction, rats were anesthetized, intubated and an intercostal incision was made to expose the apex of the heart. An ultrasonic Millar catheter was then inserted through the ventricular wall, and pressure over time measurements were recorded for a period of approximately 30-60 seconds. This model of infarct production and pressure/time measurements of cardiac function is a standard, well characterized model by which the effects of cellular therapies on cardiac function can be assessed (See e.g., Müller-Ehmsen, et al., Circulation., 105(14): 1720-6 (2002)).

The test composition was delivered using a 100 microL Hamilton syringe fitted with a 30 gauge, low dead-space needle. Five separate injections of 20 microL were performed over the course of 2-3 minutes. Four injections were performed at equal distances around the visualized infarct, while the fifth was placed directly into the center of the infarcted region as determined by area of discoloration. After injection, the incision was sutured closed, the pneumothorax was reduced, and the animals were weaned from the respirator and extubated. Four weeks after injection (5 weeks post-infarction), animals were reanesthetized, the heart was exposed through a midline sternotomy, and a Millar catheter was inserted. Dp/dt measurements were taken as described above, after which the rats were euthanized via exsanguination.

Figure 13:
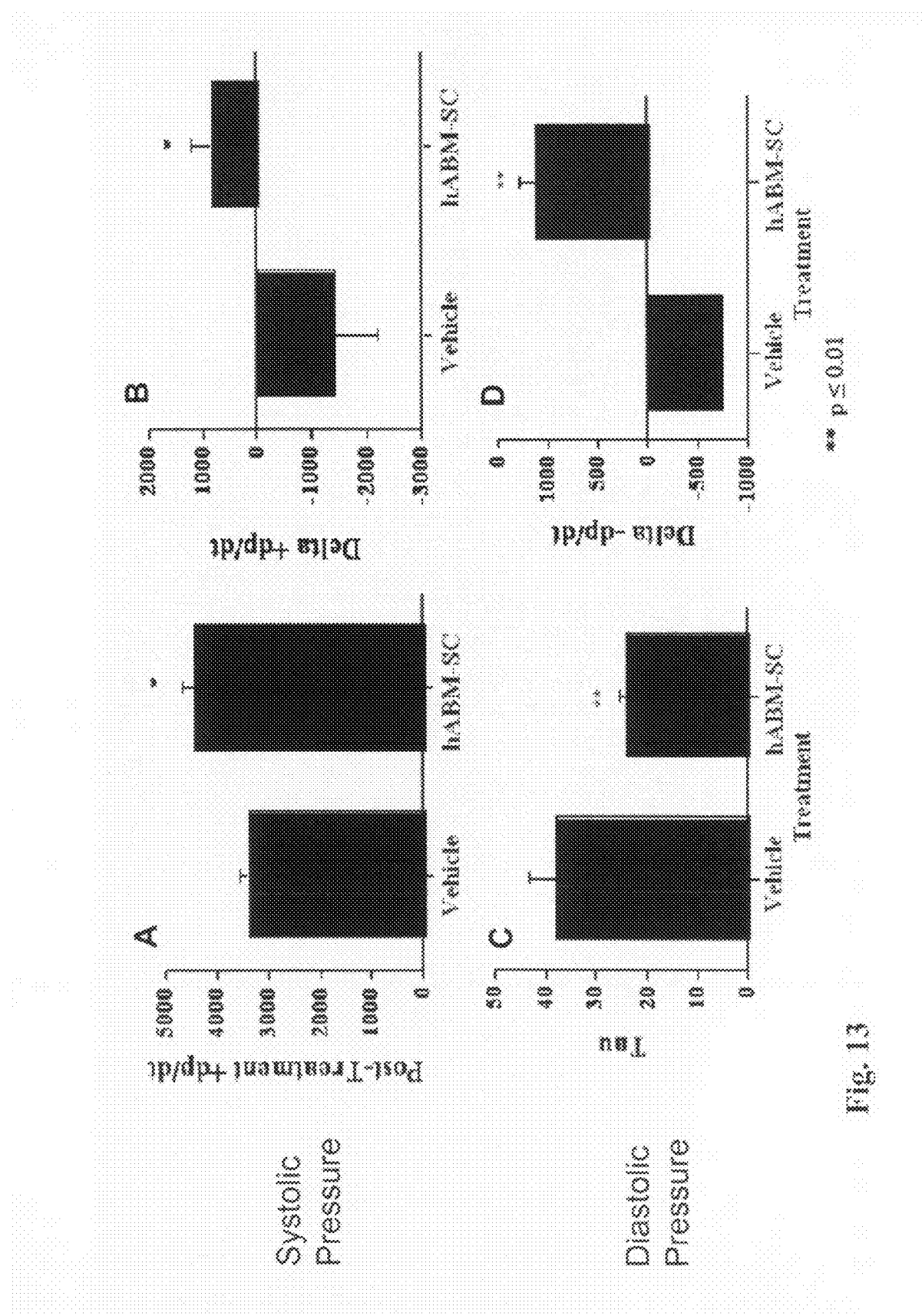
FIG. 13 shows an example of improved cardiac function results in rats treated with human ABM-SC. Four weeks after treatment, rats receiving ABM-SC demonstrated significantly higher +dp/dt (peak positive rate of pressure change) values (A). Expressing changes in cardiac function over the course of the study by subtracting 0 week +dp/dt values from 4 week values ("delta +dp/dt") demonstrated that while vehicle treated rats had decreases in cardiac function over the course of the study (negative delta), animals treated with either cell preparation showed significant improvement in cardiac function (B). Compared to vehicle treated rats, those receiving ABM-SC demonstrated significantly lower tau values (C), suggesting increased left ventricular compliance. Tau is the time constant of isovolumetric left ventricular pressure decay. For peak negative rate of pressure change (−dp/dt), expressing changes in cardiac function over the course of the study by subtracting 0 week −dp/dt values from 4 week values ("delta −dp/dt") demonstrated that while vehicle-treated rats had decreases in cardiac function over the course of the study (negative delta), animals treated with cell preparation showed significant improvement in cardiac function (D). [*p<0.05, **p<0.01 by ANOVA]

Heart Function Results (FIG. 13): Four weeks after treatment, rats receiving ABM-SC demonstrated significantly higher +dp/dt (peak positive rate of pressure change) values (A). Expressing changes in cardiac function over the course of the study by subtracting 0 week +dp/dt values from 4 week values ("delta +dp/dt") demonstrated that while vehicle treated rats had decreases in cardiac function over the course of the study (negative delta), animals treated with either cell preparation showed significant improvement in cardiac function (B). Compared to vehicle treated rats, those receiving ABM-SC demonstrated significantly lower tau values (C), suggesting increased left ventricular compliance. Tau is the time constant of isovolumetric left ventricular pressure decay. For peak negative rate of pressure change (−dp/dt), expressing changes in cardiac function over the course of the study by subtracting 0 week −dp/dt values from 4 week values ("delta −dp/dt") demonstrated that while vehicle-treated rats had decreases in cardiac function over the course of the study (negative delta), animals treated with cell preparation showed significant improvement in cardiac function (D). [*p<0.05, **p<0.01 by ANOVA]

Heart Structure Methods: Sprague-Dawley rats received experimentally-induced myocardial infarction via the placement of a permanent silk ligature around the left-anterior descending (LAD) coronary artery. Animals received a standard regimen of Cyclosporine A treatment (10 mg/kg s.c. daily) that lasted for the duration of the study.

On day 7-8 following infarction, rats were anesthetized, intubated and an intercostal incision was made to expose the apex of the heart. Cardiac function was accesses after which the test article was delivered using a 100 microL Hamilton syringe fitted with a 30 gauge, low dead-space needle. Five separate injections of 20 microL were performed over the course of 2-3 minutes. Four injections were performed at equal distances around the visualized infarct, while the fifth was placed directly into the center of the infracted region as determined by area of discoloration. After injection, the incision was sutured shut, the pneumothorax was reduced, and the animals were weaned from the respirator and extubated. Four weeks after injection (5 weeks post-infarction), animals were reanesthetized, the heart was exposed through a midline sternotomy, and cardiac function accessed. After functional measures were completed rats were euthanized via exsanguination. Rats were first deeply anesthetized using a mixture of ketamine (75 mg/kg) and medetomidine (0.5 mg/kg). The thoracic cavity was then surgically exposed and the heart dissected and immersion fixed in 10% neutral buffered formalin. Hearts were then grossly sectioned into three pieces, oriented into embedding molds, and processed for paraffin embedding. Heart tissues were then sectioned at 6 μm and stained by Hemotoxylin & Eosin (H&E) or Masson's Trichrome. At least six sections from every heart were also stained with hemotoxylin/eosin and Trichrome respectively. Specifically, trichrome staining allows for the visualization of collagen (blue) versus muscle tissue (red). Since collagen indicates the presence of scar tissue (absence of regeneration), the ratios of collagen to normal cardiac muscle were determined. A semiquantitative scoring scale was devised, with 0 as no detectable collagen and 5 as maximal/severe. Stained sections were then sent to a board certified pathologist for histomorphometric scoring.

Each slide contained three cross-sections of the heart, demonstrating a cross-sectional view of both ventricles from the mid-ventricular area (1) distal ⅓ of the ventricle (2), and apex of the ventricle (3). For histomorphometric analyses, the following grading scheme was used:

Location of tissue damage: Left ventricle (LV), Right ventricle (LV), Both ventricles (BV).

Percent of affected ventricle damaged (size of injury): Given in percent (0-100%)

Thickness score of experimentally damaged area of ventricle: Given a grade of 1-4 based on estimated thickness in millimeters. Compared with known landmarks in the tissue sections (e.g. average erythrocyte is 7 microns in diameter; average myocardial muscle bundle is 30 microns in diameter). Grade 1 (less than 0.5 mm); Grade 2 (0.5 mm to 1 mm); Grade 3 (1 mm to 1.5 mm); Grade 4 (1.5 mm+).

Neovascularization in area of tissue damage: (Grade of 0 to 4, from normal (0) to neovascularization throughout the entire area of initial tissue damage (4).

Initial vascular damage: Includes degeneration/necrosis of pre-existing blood vessels, with thrombosis and/or inflammation resulting from removal of remaining vascular debris, expressed as a grade of 0 to 4, with 0 being no vascular damage present, and 4 being vascular damage throughout the affected area.

Extent of fibrosis within the area of tissue damage: Expressed as a grade of 0 to 4, from no fibrosis (0) to (4) in 20% graduating levels of fibrosis and scarring of the initial area of damage caused by the infarction procedure. For example, fibrosis of 20% of the ventricle would be assigned a grade of (1), and fibrosis of 40% of the ventricle would be assigned a grade of (2), 60% would receive a (3), and above 60% would receive a (4).

Figure 14:
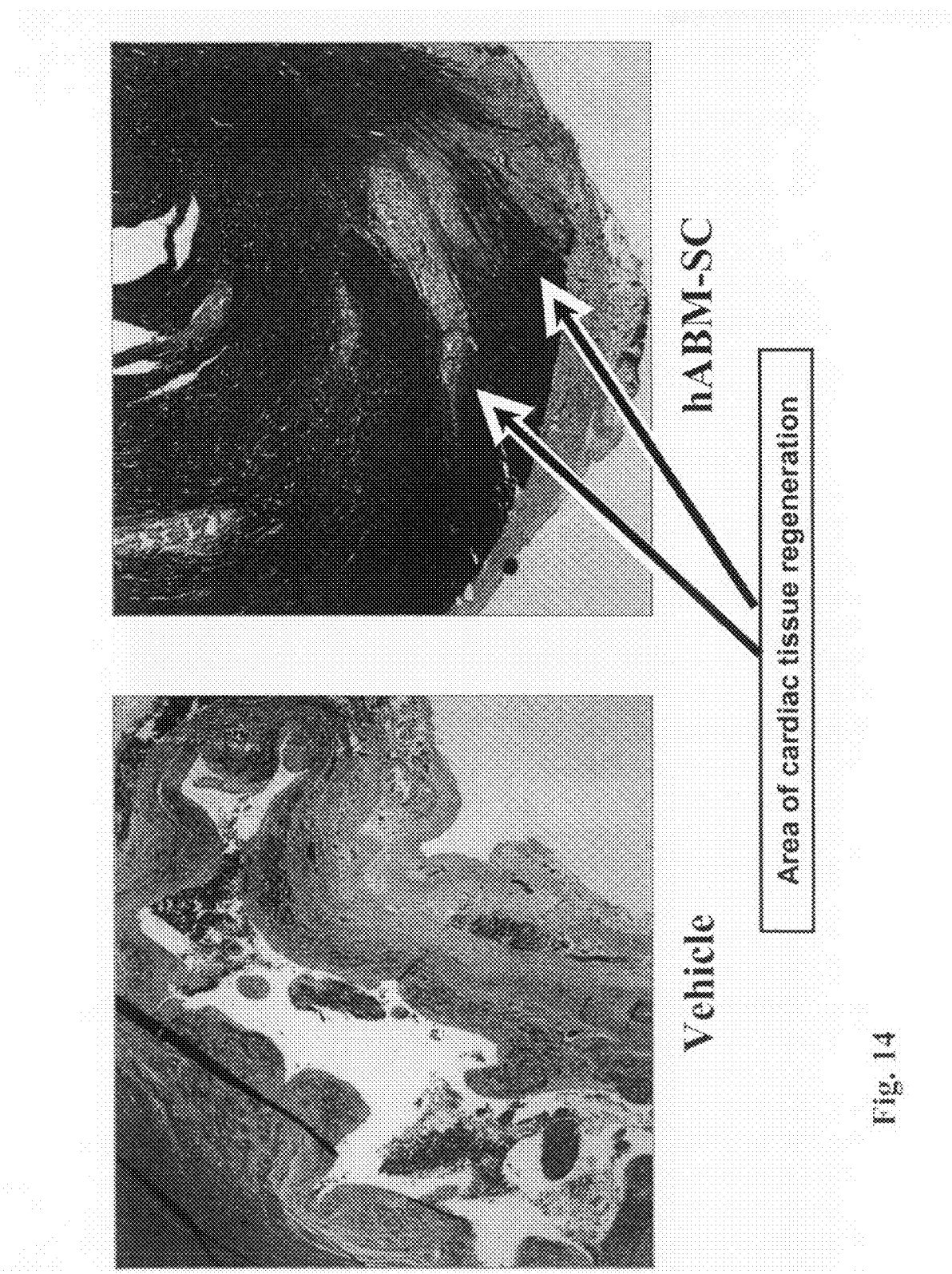
FIG. 14 shows reduction of fibrosis and enhanced angiogenesis in a rat model myocardial infarct treated with hABM-SC. Semi-quantitative scoring was used to evaluate changes in infarct size in the hearts of rats receiving vehicle or ABM-SC seven days after myocardial infarction. Histopathological analysis, performed approximately 30 days after administration of ABM-SC, indicated significant reduction in infarct size in rats receiving hABM-SC compared to vehicle. According to a preset scale, rats receiving hABM-SC had histological scores approximately two points lower than vehicle controls. This figure shows an example of typical infarct size reduction.

Heart Structure Results: Rats were subsequently sacrificed and cardiac tissue was sectioned and stained. A board certified veterinary pathologist performed semiquantitative scoring (FIG. 15) to evaluate changes in infarct size in the hearts of rats receiving vehicle or ABMSC seven days after myocardial infarction. Histopathological analysis indicated significant reduction in infarct size in rats receiving hABM-SC compared to vehicle. According to a preset scale, rats receiving hABM-SC had histological scores approximately two points lower than vehicle controls. FIG. 14 shows an example of typical infarct size reduction. Histopathological analysis determined that hABM-SC reduced fibrosis and increased vascularization in the infarct zone (FIG. 15), consistent with pro-regenerative activity. Thus, it was observed that rats treated with hABM-SC showed dramatic improvement of cardiac tissue structure. See, FIGS. 14 and 15.

Example 10

Adult Bone Marrow-Derived Somatic Cells Suppress Immune Mediated Responses

Part I: Suppression of Mitogen-Induced T-Cell Proliferation in One-Way MLR (Mixed Lymphocyte Reaction) Assay.

Methods: Human ABM-SC and exABM-SC (Lot #RECB801 and RECB906, respectively), were plated in 75 cm² flasks at a concentration of 6000 viable cells/cm² in 15 mL complete media such as Advanced DMEM (GIBCO™; Catalog #12491-015, Lot #1216032 (Invitrogen Corp., Carlsbad, Calif., USA)) supplemented with 4 mM L-glutamine (Catalog #SH30034.01. Lot #134-7944, (HYCLONE™ Laboratories Inc., Logan, Utah, USA)) or HyQ® RPMI-1640 (HYCLONE™ Catalog #SH30255.01, Lot #ARC25868) containing 4 mM L-glutamine and supplemented with Insulin-Transferrin-Selenium-A (ITS) (GIBCO™; Catalog #51300-044, Lot #1349264) and incubated at 37° C. in a humidified trigas incubator (4% $O_2$, 5% $CO_2$, balanced with Nitrogen). After 24 hrs, spent media was aspirated and replaced with 155 mL fresh media. Human mesenchymal stem cells (hMSC) (Lonza BioScience, formerly Cambrex Bioscience, Catalog #PT2501, Lot #6F3837) were plated in 75 cm² flasks at a concentration of 6000 viable cells/cm² in 15 mL MSCGM™ (Lonza BioScience) and incubated at 37° C. in a humidified incubator at atmospheric $O_2$ and 5% $CO_2$. After 24 hrs, spent media was aspirated and replaced with 15 mL fresh MSCGM™. Both hABM-SC and hMSC were harvested after 96 hours in culture. Harvested hABM-SC and hMSC were plated in 96-well round bottom plates at a concentration of 25,000 viable cells/mL in RPMI-complete media (Hyclone). Human peripheral blood mononuclear cells (PBMCs) were labeled in 1.25 uM CarboxyFluoroscein Succinimidyl Ester (CFSE) and cultured at 250,000 cells/well in RPMI-complete media along with hMSC, RECB801, RECB906 or alone. To stimulate T cell proliferation, cultures were inoculated with 2.5 or 10 micrograms/mL Phytohaemagglutinin (Sigma Chemical). Cells were then harvested after 72 hrs later and stained with CD3-PC7 antibody (Beckman Coulter), as per manufacturer's instructions, and analyzed on a Beckman FC 500 Cytometer, using Flow Jo software. Only CD3+ cells were gated analyzed for division index.

Figure 16:
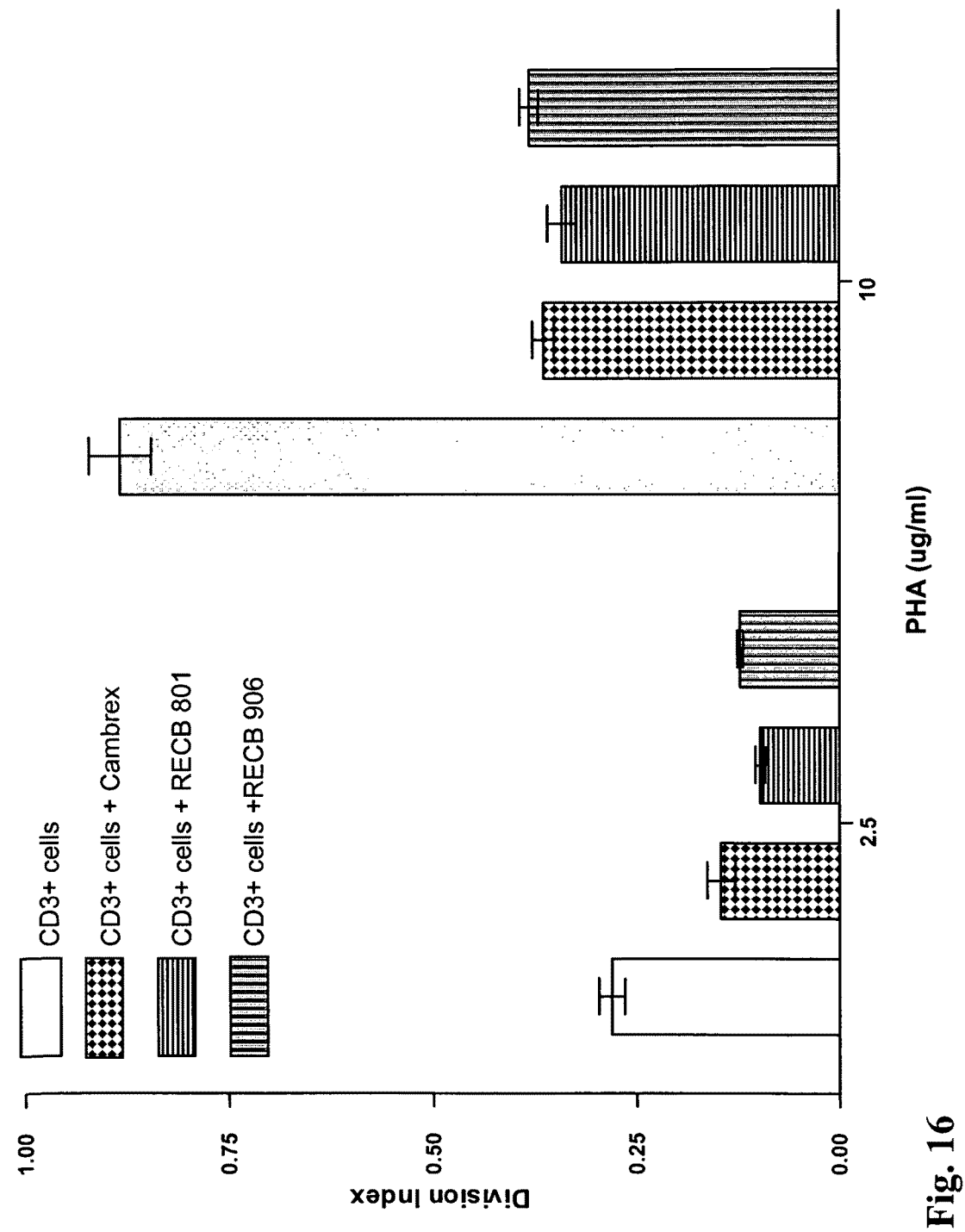
FIG. 16 shows that allogeneic human ABM-SC and exABM-SC suppress mitogen-induced T-cell proliferation in one-way MLR (mixed lymphocyte reaction) assay.

Results: Allogeneic human ABM-SC and exABM-SC suppress mitogen-induced T-cell proliferation in one-way MLR assay. See, FIG. 16.

Part II: Allogeneic Porcine ABM-SC Fail to Illicit T-Cell Mediated Immune Response in 2-Way MLR Challenge Assay.

Methods: Porcine whole blood was collected for immunoassays on Day 0 (prior to treatment) and at necropsy (Day 3 or Day 30 post-treatment) for cellular immune response analysis. PBMC from each animal were cultured with pABM-SC, the mitogen ConA, or media alone. Samples were analyzed by flow cytometry and the amount of proliferation calculated using FlowJo software.

Whole blood samples were diluted 1:1 with DPBS (Dulbecco's PBS)-2% Porcine Serum. Diluted blood was overlayed on Ficoll (2:1 ratio diluted blood to Ficoll) and centrifuged at 350×G for 30 minutes, with centrifugation cycle ending with zero braking. The resulting top layer was aspirated. The middle layers, which contain the desired mononuclear cells, were pooled for each sample, and washed in 3× with DPBS-2% Porcine Serum. After washing, the pellet was resuspended in 20 mL ACK lysis buffer and incubated for 3 minutes, to remove residual red blood cells, then centrifuged for 5 minutes, at 250×G. The pellets were washed in 20 mL DPBS-2% Porcine Serum and resuspended in 5 mL RPMI Complete media (RPMI-1640, 10% Porcine serum, 2 mM L-glut, 20 mM HEPES, 0.1 mM NEAA, 1× Penn-Strep). Cells were frozen at a concentration of 20×10⁶ cells/mL by centrifugation, and resuspension in ice cold freeze media (10% DMSO in Porcine Serum) and immediately added to 2 mL cryovials and placed into a cryorate freezer. (freeze rate=–25° C./min to –40° C., +15° C./min to –12.0° C., –1° C./min to –40° C., –10° C./min to –120° C.). Cells were stored in 2 mL aliquots per vial in vapor phase of liquid nitrogen until use.

On day 0, pABM-SC were plated in 96 well culture dishes at a concentration of 10,000 cells/well in AFG-104 media according to study template for each test condition. Plates were incubated overnight at 37° C. in a humidified incubator with low $O_2$ (4-5%), ~5% $CO_2$ balanced with nitrogen.

The following day, PBMC were labeled with CFSE (carboxy-fluorescein diacetate, succinimidyl ester). In short, thawed vials of PBMC in 37° C. water bath, washed with 10 mL RPMI-Complete media centrifuged cells at 300×G, and resuspended in DPBS. Cell concentrations were adjusted to 10×10⁶ cells/mL and incubated with CFSE at a final concentration of 0.625 mM for 5 minutes. Cells were immediately washed in 40 mL ice cold DPBS/5% porcine serum and centrifuged 10 minutes at 300×G. Cells were again washed in 25 mL DPBS/5% porcine serum and centrifuged as before. Cells were washed a third and final time in 10 mL RPMI-complete media. Cell concentrations were adjusted to a final concentration of 5×10⁶ cells/mL. Labeled PBMC were added to the assay plate according to study template as follows: AFG-104 media was aspirated and replaced with 100 microL RPMI-Complete media. 100 microL of RPMI-complete media was added to non-stimulated wells, 100 microL media with 20 microg/mL ConA in RPMI-Complete media was added to stimulated wells, and 4.5% Glucose-RPMI-Complete media to vehicle cells. 500,000 labeled PBMC were plated per well in 96 well plates according to study template. Plates were incubated for 5 days at 37° C., atmospheric $O_2$ (high $O_2$), with humidity, 5% $CO_2$ no nitrogen. All conditions were completed in triplicate for each blood sample received. Vehicle stimulation was completed for a subset of blood samples, but was not significantly different than media alone. After 5 days of co-culture, cells were harvested for flow cytometry by transferring cells from 96 well plate to a flow tube. Indirect staining was conducted in accordance with standard protocols. The primary antibody used was Biotin Conjugated Mouse anti-Pig CD3 Monoclonal antibody; followed by exposure to Streptavidin-PE-Cy7 secondary reagent. Cells were resuspended in 200 microL flow wash buffer and analyzed on a Coulter FC500 device.

Figure 17:
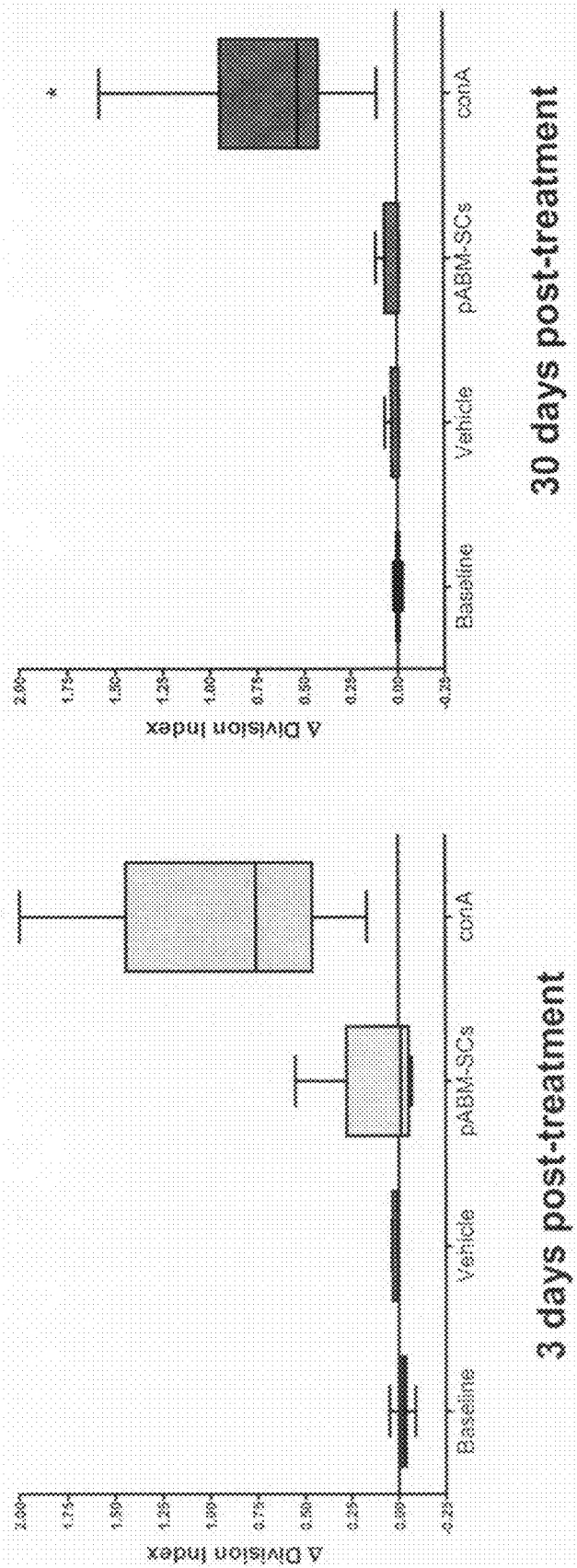
FIG. 17 shows that allogeneic porcine ABM-SC fail to illicit T-cell mediated immune response in a 2-way MLR challenge experiment. A Division Index was calculated for samples collected at baseline and 3 or 30 days post-treatment and then challenged in vitro with media, vehicle, pABM-SC or ConA. The average division index from all animals at Day 3 or Day 30 for CD3+ cells which were stimulated with ConA was significantly higher than the division index for CD3+ cells from vehicle and pABM-SC treated animals at both pre-treatment and necropsy (*p<0.05).

Results: A Division Index was calculated for samples collected at baseline and at 3 or 30 days post-treatment and then challenged in vitro with media, vehicle, pABM-SC or ConA. The average division index from all animals at Day 3 or Day 30 for CD3+ cells stimulated with ConA was significantly higher than the division index for CD3+ cells from vehicle and pABM-SC treated animals at pre-treatment and at necropsy (*p<0.05). See, FIG. 17.

Example 11

Clinical Development

A Phase 1, open label, dose escalation study to evaluate the safety of a single escalating dose of hABM-SC administered by endomyocardial injection to cohorts of adults 30-60 days following initial acute myocardial infarction has been undertaken. The primary objective of this study was investigate the safety and feasibility of single escalating doses of hABM-SC delivered via multiple endomyocardial injections using the MYOSTAR™ catheter, guided by the NOGA™ or NOGA XP™ electromechanical cardiac mapping system. A secondary objective was to investigate the preliminary efficacy of single escalating doses of hABM-SC, measured by left ventricular volume, dimension, myocardial infarction size and voltage.

The study protocol provides that test subjects are to be followed for 12 months with frequent monitoring for safety. Efficacy assessments are to be performed at 90 day and six month follow-up visits. The intended study population is 30 to 75 year old consenting adults with an acute myocardial infarction (AMI) within the previous 30 days who have been successfully treated with percutaneous revascularization restoring TIMI II or higher flow, with a left ventricular ejection fraction of greater than or equal to 30% as measured by myocardial perfusion imaging (SPECT).

Inclusion and Exclusion Criteria: Inclusion criteria for the study comprises: (1) 30-75 years of age (inclusive); (2) 30-60 days since AMI (defined as the most recent MI causing a doubling in cardiac-specific troponin I (cTnI) enzyme concentrations relative to normal levels in addition to ECG changes consistent with MI with confirmation by myocardial perfusion imaging [SPECT]); (3) successful percutaneous revascularization of restoring TIMI II or higher flow to infarcted area; (4) negative pregnancy test (serum_hCG) in women of childbearing potential (within 24 hours prior to dosing); (5) left ventricular ejection fraction (LVEF) >30% as measured by myocardial perfusion imaging (SPECT); (6) cardiac enzyme tests (CPK, CPK MB, cTnI) within the normal range at baseline; (7) must be ambulatory.

Exclusion criteria for the study comprises: (1) significant coronary artery stenosis that may require percutaneous or surgical revascularization within six months of enrollment; (2) left ventricular (LV) thrombus (mobile or mural); (3) high grade atrioventricular block (AVB); (4) frequent, recurrent, sustained (>30 seconds) or non-sustained ventricular tachycardia >48 hours after AMI; (5) clinically significant electrocardiographic abnormalities that may interfere with subject safety during the intracardiac mapping and injection procedure; (6) atrial fibrillation with uncontrolled heart rate; (7) severe valvular disease (e.g., aortic stenosis, mitral stenosis, severe valvular insufficiency requiring valve replacement); (8) history of heart valve replacement; (9) idiopathic cardiomyopathy; (10) severe peripheral vascular disease; (11) liver enzymes (Aspartate aminotransferase [AST]/alanine aminotransferase [ALT]) >3 times upper limit of normal (ULN); (12) serum creatinine >2.0 mg/dL; (13) history of active cancer within the preceding three years (with exception of basal cell carcinoma); (14) previous bone marrow transplant; (15) known human immunodeficiency virus (HIV) infection; (16) evidence of concurrent infection or sepsis on chest X-ray (CXR) or blood culture; (17) participation in an experimental clinical trial within 30 days prior to enrollment; (18) alcohol or recreational drug abuse within six months prior to enrollment; (19) major surgical procedure or major trauma within the 14 days prior to enrollment; (20) known autoimmune disease (e.g., systemic lupus erythematosus [SLE], multiple sclerosis); (21) clinically significant elevations in prothrombin (PT) or partial thromboplastin time (PTT) relative to laboratory norms; (22) thrombocytopenia (platelet count <50,000/mm3); (23) inadequately controlled diabetes mellitus type I or type II, defined as a change in anti-diabetic medication regimen within the prior 3 months or HbA1c >7.0%; (24) uncontrolled hypertension defined as systolic blood pressure (SBP) >180 mmHg and/or diastolic blood pressure (DBP) >100 mmHg; (25) use of ionotrophic drugs> 24 hours post AMI; (26) other co-morbid conditions such as hemodynamic instability, unstable arrythmias, and intubation, which, in the opinion of the principal investigator, may place subjects at undue risk or interfere with the objectives of the study; (27) any other major illness, which, in the opinion of the principal investigator, may interfere with the subject's ability to comply with the protocol, compromise subject safety, or interfere with the interpretation of the study results; and, (28) contraindication (either allergy or impaired renal function) to injection with contrast media for adequate CT scan evaluations.

Study Drug Dosage and Administration: Subjects in the same cohort will be dosed no closer than three days apart, and dosing of successive cohorts will be separated by approximately four weeks, following review of at least three weeks of safety data on all subjects in the previous cohort.

| Cohorts | Dose |
| --- | --- |
| Cohort 1 | $30 \times 10^6$ cells |
| Cohort 2 | $100 \times 10^6$ cells |
| Cohort 3 | $300 \times 10^6$ cells |
| Cohort 4 | $300 \times 10^6$ cells or MTD |

On the day of dosing, after baseline evaluations are complete and immediately following percutaneous ventricular mapping with the NOGA™ or NOGA XP™ electromechanical mapping system (Biosense Webster, Diamond Bar, Calif.), multiple sequential injections of hABM-SC will be delivered directly into the myocardium from a percutaneous, LV approach using a MYOSTAR™ catheter.

Study Procedures: Potential subjects will be consented and screened within 21 days prior to planned hABM-SC administration, which must occur within 30-60 days following AMI. Screening procedures to determine eligibility also will be used as baseline values, unless hospital SOPs require additional tests (i.e., immediately prior to catheterization). Baseline testing for treatment efficacy is to consist of a Six Minute Walk Test, NYHA classification, blood analysis for B-type natriuretic peptide (BNP) concentration, echocardiography, right and left cardiac catheterization, myocardial perfusion imaging (SPECT), and NOGA™ or NOGA XP™ electromechanical mapping. On the day of admission, additional baseline blood testing (including pregnancy testing [serum_hCG] for female subjects of childbearing potential) will be done, and eligibility will be verified. On the day of dosing (Study Day 0), subjects will undergo NOGA™ or NOGA XP™ electromechanical cardiac mapping and a MYOSTAR™ catheter will be placed into the left ventricle. The dose of hABM-SC will be administered via multiple sequential endomyocardial injections into the damaged (defined by NOGA™ or NOGA XP™) myocardial tissue. After administration of hABM-SC, echocardiography will be performed to detect possible transmural perforation, and the subject will be admitted directly to the intensive care unit (ICU) for a minimum of twenty-four hours of observation with continuous cardiac telemetric monitoring. Stable subjects without complications will be discharged from the ICU to a step down unit (with cardiac monitoring) and then discharged to home no sooner than 72 hours after the dosing procedure. Subjects with complications will remain in the ICU under optimal medical management until stable and appropriate for discharge to the step down unit. Safety evaluations will be performed 7, 14, 21, 60 and 90 days and at six and twelve months following administration of hABM-SC. Efficacy evaluations will be performed at 90 days and six months after the procedure, and will include left ventricular volume, dimension, size of myocardial infarction and voltage, measured respectively by contrast enhanced echocardiography, myocardial reperfusion and viability analysis (SPECT), right and left cardiac catheterization (90 days only), six minute walk test, NYHA classification, and NOGA™ or NOGA XP™ electromechanical mapping (90 days only).

Safety endpoints in the study will comprise: (1) adverse events as detailed in the study protocol; (2) clinically significant changes from baseline in blood or blood components including CBC, CMP, CPK/CPK MB, cTn1, PT/PTT, and HLA antibody analysis; (3) clinically significant changes from baseline in cardiac electrical activity as assessed by electrocardiogram (ECG) or cardiac telemetry; (4) clinically significant changes from baseline in cardiac electrical activity as assessed by 24 hour Holter monitoring; (5) perioperative myocardial perforation as assessed by echocardiogram (post procedure); and, (6) clinically significant changes from baseline in physical and mental status as assessed by physical examination including a focused neurological examination. If signs and symptoms consistent with cerebrovascular accident (stroke) are observed, a neurological consult will be obtained for further evaluation Efficacy Endpoints: Efficacy endpoints to be monitored comprise: (1) end systolic and/or end diastolic volume compared to baseline, as measured by myocardial perfusion imaging (SPECT); (2) myocardial infarction size compared to baseline as measured by myocardial perfusion imaging (SPECT); (3) end systolic and/or end diastolic dimensions compared to baseline as measured by contrast enhanced 2-D echocardiography; (4) action potential voltage amplitude in the area of hABM-SC injected myocardium as compared to baseline and historical controls (provided by the core laboratory) as measured by NOGA™ or NOGA XP™ electromechanical mapping; (5) cardiac output and pressure gradients compared to baseline as determined by right and left cardiac catheterization; (6) quality of life compared to baseline as assessed by the Six Minute Walk Test; and, (7) functional cardiovascular disease class (NYHA functional classification scheme) compared to baseline as assessed by the physician performing scheduled physical examinations.

Endomyocardial Delivery of hABM-SC: hABM-SC will be delivered to the myocardium via direct catheter-guided injection from within the ventricular chamber. Endomyocardial delivery of hABM-SC will be accomplished with the aid of the NOGA™ Cardiac Navigation System (one of the most advanced systems for three dimensional visualization of the physical, mechanical and electrical properties of intact myocardium in vivo; from Biosense-Webster, Diamond Bar, Calif.). The actual injection will be performed with the Cordis MYOSTAR™/catheter. The NOGA™ system allows for real time viewing of left ventricular heart function, detection of heart tissue damage, observation and placement of the catheter tip. Given the tenuous cardiac condition of patients post-AMI, a relatively non-invasive delivery system (compared to open heart or direct intracardiac delivery), i.e. the MYOSTAR™ Injection Catheter used in conjunction with the NOGA™ mapping system, was selected for administration of hABM-SC.

Preliminary Results: Preliminary results for 5 patients have been obtained. The first 3 patients comprised the initial dose group (30 million cells), while the last two patients received the second escalating dose (100 million cells). Overall, hABM-SC was well tolerated in all patients, with some trends to improvement in cardiac function noted in several patients. More detailed results are discussed below.

Safety Findings: No evidence of allogeneic immune response (as measured by pre- and post-treatment antibody profiling) was found in any patients.

Cardiac Functional Assessments: NOGA Electromechanical Mapping: Functional mapping was performed at time of treatment and at 90 days after cell treatment. Representative unipolar voltage maps were obtained from the second patient in the first dose cohort. A clear voltage deficit could be seen in the area of infarct (data not shown). Fifteen cell injections were performed at the margin of the infarct using unipolar voltage as a guide. At 90 days follow up, a clear improvement in unipolar voltage could be seen, with near normal voltages prevailing in the infarct zone. Similar degrees of improvement in voltage were noted in patients 1, 3 and 4 (data not shown).

Myocardial Perfusion Imaging (SPECT): Perfusion imaging was performed at baseline, 90 days and 6 months after cell treatment according to previously published methods.

All images were digitally captured and analyzed. Ejection fraction, perfusion deficit size, and ventricular volumes were derived from this analysis, under basal and adenosine-stress conditions, along with a 24 hour-washout rescan. Results for each patient at each time point are discussed below.

Perfusion Deficit: In general, perfusion deficit sizes, which are thought to represent overall infarct sizes, either decreased or remained unchanged over the six months of follow up for treated patients. Two patients demonstrated reductions in deficit deemed "clinically significant" meaning the deficits resolved to less than 4-5% of the total ventricular wall. In both of these cases, the areas of improvement corresponded to areas of voltage improvement as measured by NOGA mapping. Although NOGA mapping is considered investigational, this data supports validity of the hypothesis that unipolar voltage may be a surrogate for infarct size measurement.

Ejection Fraction (EF): In general, ejection fraction in study patients either improved or remained relatively unchanged. One patient experienced a significant drop in overall EF (63% to 50% over six months), but this patient experienced a serious adverse event during the course of cell treatment which renders it questionable whether or not a complete dose of cells was actually administered to the endomyocardium. Two patients demonstrated increases in EF well above the expected for this patient group. The lack of placebo controls precludes any conclusions as to the mechanism of this improvement.

End-Diastolic Volume (EDV): EDV was measure at baseline and at 90 days and 6 months following treatment. In general, EDV remained unchanged in all patients over the 6 month follow up period, suggesting no significant remodeling occurred in these patients.

Figure 18:
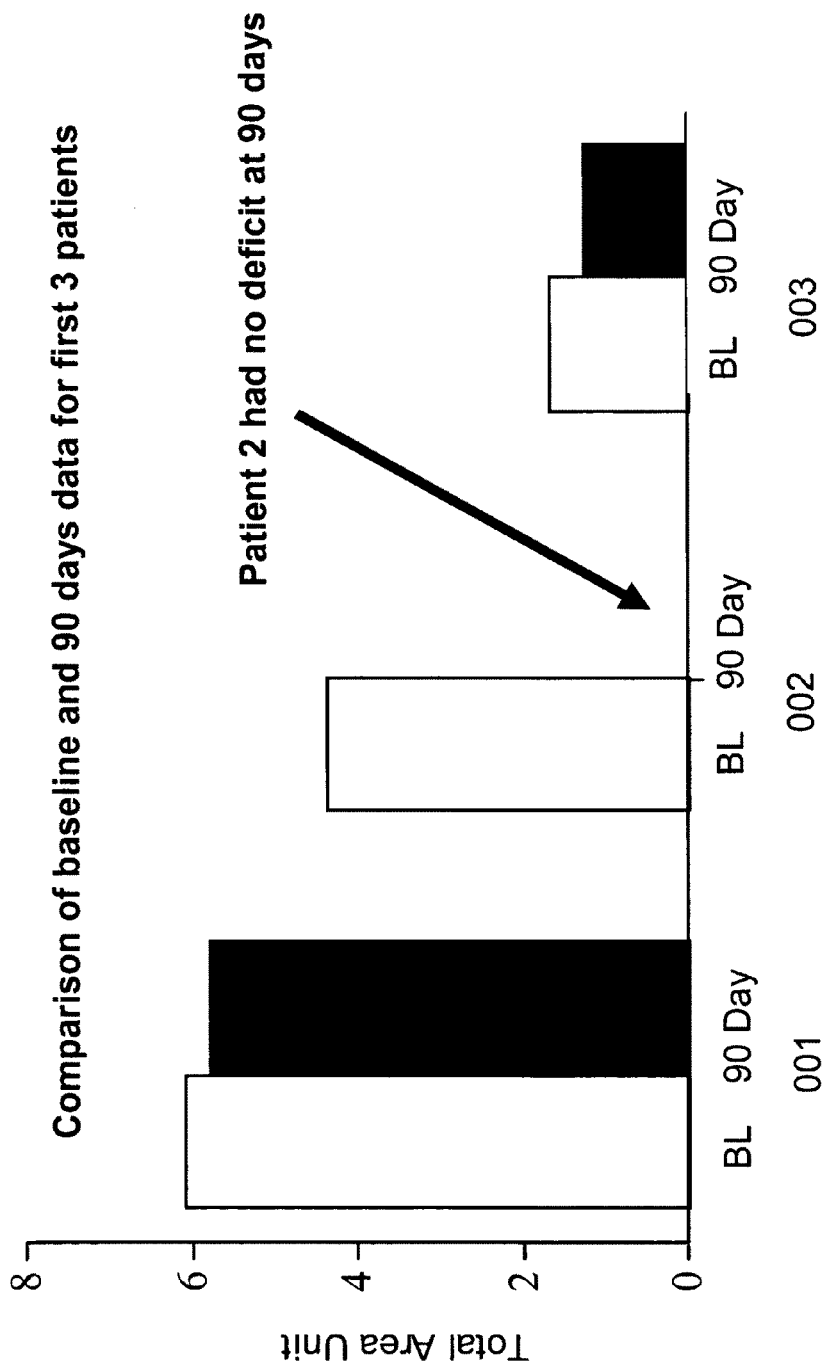
FIG. 18 shows the changes in cardiac fixed perfusion deficit size in three patients by comparison of baseline (BL) measurements, with measurements obtained 90 days post-treatment with hABM-SC.
Figure 19:
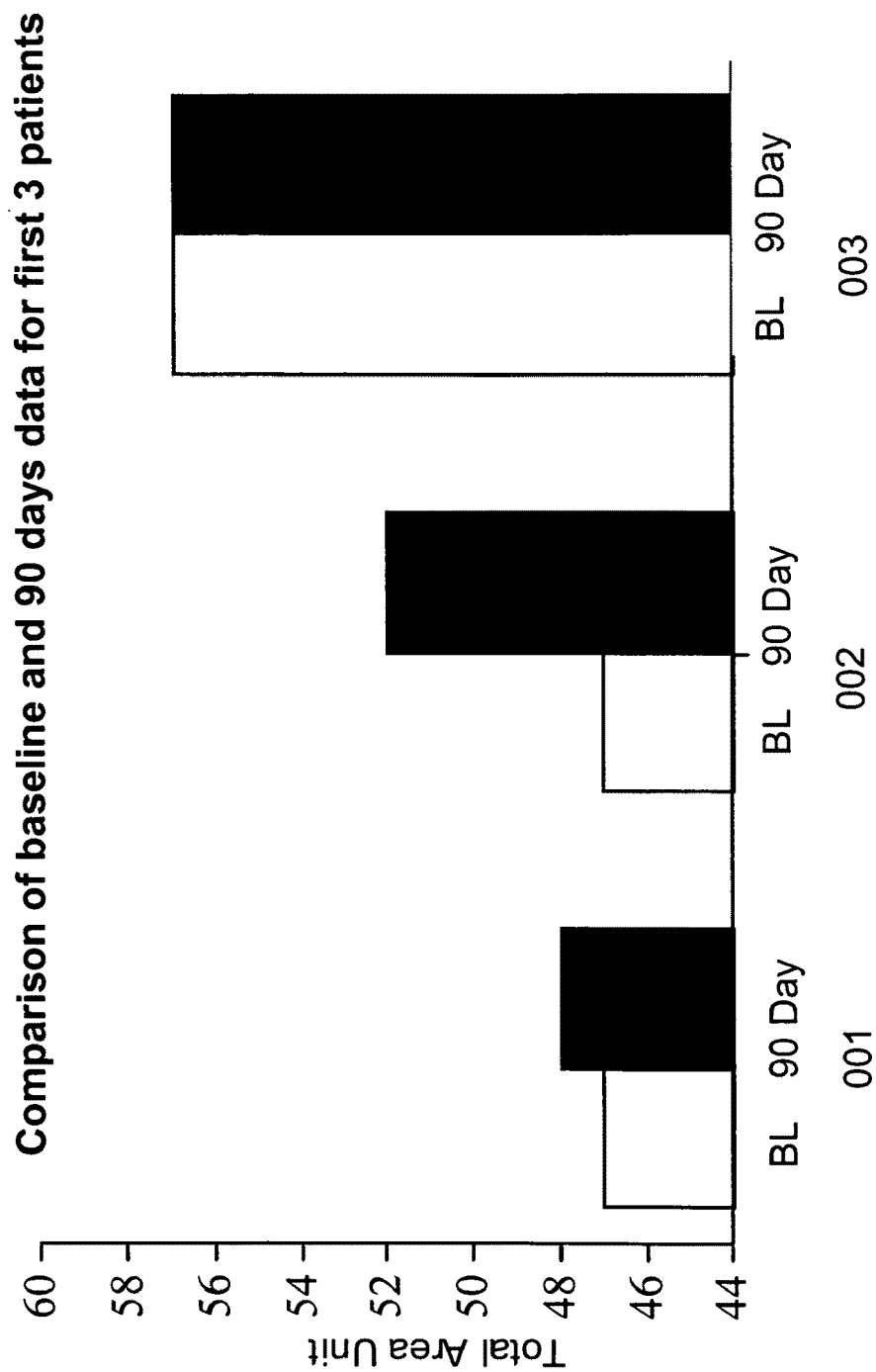
FIG. 19 shows the changes in cardiac ejection fractions measured in three patients by comparison of baseline (BL) measurements with measurements obtained 90 days post-treatment with hABM-SC.

FIG. 18 shows the changes in cardiac fixed perfusion deficit size in three patients by comparison of a baseline (BL) measurements with measurements obtained 90 days post-treatment with hABM-SC. FIG. 19 shows the changes in cardiac ejection fractions measured in three patients by comparison of a baseline (BL) measurements with measurements obtained 90 days post-treatment with hABM-SC.

Example 12

Figure 20:
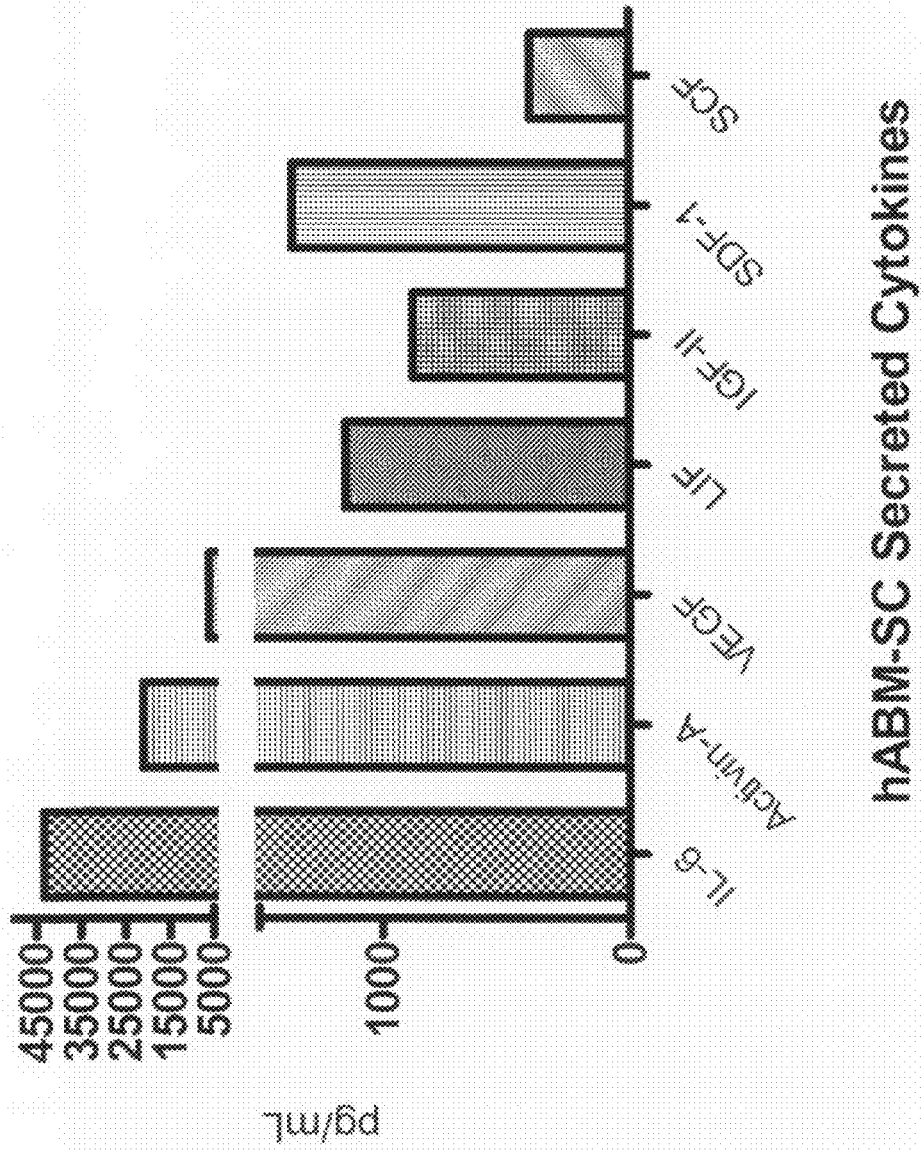
FIG. 20 shows examples of quantities of erythropoietic cytokines secreted in vitro by hABM-SC (i.e., IL-6, Activin-A, VEGF, LIF, IGF-II, SDF-1 and SCF). ABM-SC lots were tested for cytokine secretion using RAYBIO™ Human Cytokine Antibody Array (RayBiotech, Inc.). Cells were first cultured in serum-free Advanced DMEM (GIBCO™) for three days to generate conditioned medium (CM). The CM was then concentrated using CENTRICON™ PLUS-20 Centrifugal Filter Units (Millipore) prior to analysis.

Human ABM-SC and Compositions Derived Thereby for the Production of Red Blood Cells In Vitro It is well known that the bone marrow microenvironment provides the requisite combination of matrix molecules, growth factors and cytokines necessary to support and modulate hematopoiesis (Dexter at al. 1981). Most, if not all, of the trophic factors known to drive hematopoietic cell self-renewal and lineage restricted differentiation derive from the mesenchymal support cells (Quesenberry et al. 1985). Roecklein and Torok-Storb (1995) showed that even within a relatively pure population of these cells, sub-populations can be isolated that differentially support hematopoiesis. Unlike the immortalized clones described in these previous publications, the hABM-SC utilized as described herein represent a pure population of CD45 negative, CD90/CD49c co-positive non-hematopoietic support cells that secrete many factors important for inducing and maintaining erythropoiesis including, but not limited to, IL-6 (Ullrich et al. 1989), LIF (Cory et al. 1991), SDF-1 (Hodohara et al. 2000), SCF (Dai et al. 1991), Activin-A (Shao et al. 1992), VEGF and IGF-II (Miharada et al. 2006) (FIG. 20).

To generate red blood cells from a starting population of hematopoietic precursors (e.g. embryonic stem cells (ES), hematopoietic stem cells (HSC), cord blood cells (CBC) or committed erythroblast precursors (BFU-E)), human ABM-SC and/or compositions produced by such cells can be utilized to induce, enhance, and/or maintain erythropoiesis by delivering a "cocktail" of erythropoietic factors necessary for, or to supplement, growth and differentiation of hematopoietic precursors into erythroblasts. See, FIG. 20.

Example 13

Production, Isolation, Purification, and Packaging of Cell-Derived Compositions and Trophic Factors A two-step, downstream bioprocess has been developed to manufacture, collect and purify compositions such as secreted growth factors, cytokines, soluble receptors and other macromolecules produced by human ABM-SC and exABM-SC. This cocktail of secreted cell compositions, produced as such in the stoichiometric ratios created by the cells, has tremendous potential as a pro-regenerative therapeutic, cell culture reagent and/or research tool for studying in vitro cell and tissue regeneration. Such compositions can also be used as an alternative to the cells themselves to support the growth and lineage-appropriate differentiation of starting erythroid progenitor cell populations in suspension cultures.

Production of Sera-Free Conditioned Media

Cryopreserved human ABM-SC (Lot no. P25-T2S1F1-5) are thawed and re-suspended in one liter of Advanced DMEM (GIBCO, catalog #12491-015, lot 284174 (Invitrogen Corp., Carlsbad, Calif., USA)) supplemented with 4 mM L-glutamine (HYCLONE Laboratories Inc., Logan, Utah, USA catalog #SH30255.01).

Cells are seeded in a Corning® CellBind® polystyrene CellSTACK® ten chamber (catalog number 3312, (Corning Inc., NY, USA)) at a density of 20,000 to 25,000 cells per cm$^2$. One port of the CellSTACK® ten chamber unit is fitted with a CellSTACK® Culture chamber filling accessory (Corning® Catalog number 3333, (Corning Inc., NY, USA)) while the other port is fitted with a CellSTACK® Culture chamber filling accessory 37 mm, 0.1 µM filter (Corning® Catalog number 3284, (Corning Inc., NY, USA)).

Cultures are placed in a 37° C.±1° C. incubator and aerated with a blood gas mixture (5±0.25% $CO_2$, 4±0.25% $O_2$, balance Nitrogen (GTS, Allentown, Pa.)) for 5±0.5 hrs. After 24±2 hrs post seeding, the media is removed, replaced with 1 liter of fresh media and aerated as previously described. Approximately, 72±2 hours later the sera-free conditioned media is aseptically removed from the CellSTACK® ten chamber unit within a biological safety cabinet and transferred to a one liter PETG bottle. The sera free conditioned media is subsequently processed by tangential flow filtration.

Isolation and Purification of Sera-Free Conditioned Media

Tangential flow filtration (TFF) is performed on a reservoir of sera free conditioned media, recovered from a CellSTACK® ten chamber unit, as described above. A polysulfone hollow fiber with a molecular weight cut-off of 100 kilodaltons (kD) (Catalog number M1ABS-360-01P (Spectrum Laboratories, Inc., Rancho Dominguez, Calif., USA)) is employed. The reservoir of sera free conditioned (the retentate) is re-circulated through the lumen of the hollow fiber tangential to the face of the lumen. Molecules with a molecular weight of 100 kD or less pass through the lumen into a 2 liter PETG bottle; this fraction is called the permeate or filtrate. The retentate is continually re-circulated until the volume is reduced to approximately less than 50 mL. The retentate is subsequently discarded and the permeate is retained for further processing. The resulting permeate (approximately 1 liter) is a clear, sera-free solution containing small molecular weight molecules free of cellular debris and larger macromolecules, herein referred to as Fraction #1.

Fraction #1 is subsequently subjected to additional TFF using a polysulfone hollow fiber with a molecular weight cut off of 10 kilodaltons (kD) (Catalog number M11S-360-01P (Spectrum Laboratories, Inc., Rancho Dominguez, Calif., USA)). Fraction #1 is subsequently used as the retentate and re-circulated through the lumen of the hollow fiber, tangential to the face of the lumen. Smaller molecules ≦10 kD (i.e. ammonia, lactic acid etc.) are allowed to pass through the lumen. After the volume of the retentate is reduced to 100 mL, diafiltration of the solution is begun. One liter of alpha-MEM without phenol red (HYCLONE, catalog number RR11236.01 (HYCLONE Laboratories Inc., Logan, Utah, USA)) is added to the retentate reservoir at the same rate that the permeate is pumped out; thus maintaining the volume of the reservoir constant. The resulting retentate contains small only small molecules ranging in molecular weight from 10 kD to 100 kD; herein referred to as Fraction #2.

Fraction #2 can be further processed by subjecting it to additional TFF using a polysulfone hollow fiber with a molecular weight cut off of 50 kilodaltons (kD) (Catalog number M15S-360-01P (Spectrum Laboratories, Inc., Rancho Dominguez, Calif., USA)). Fraction #2 is thus re-circulated through the lumen of the hollow fiber, tangential to the face of the lumen. Smaller molecules ≦50 kD are passed through the lumen. Both processing streams are retained as product. The resulting permeate/filtrate is composed primarily of molecules 10 kD to 50 kD (Fraction #3), while the retentate comprises macromolecules in the range of 50 kD to 100 kD (Fraction #4).

Each of the resulting fractions is frozen in 60 mL PETG bottles (Catalog number 2019-0060, Nalgene Nunc International Rochester N.Y.).

Such Isolated protein fractions can subsequently be subjected to further aseptic downstream processing and packaging, wherein such compositions can be dialyzed, lyophilized, and reconstituted into a dry, biocompatible matrix, such as LYOSPHERES™ (manufactured by BIOLYPH™, Hopkins, Minn., USA).

Example 14

Isolation, Cryopreservation, and Expansion of CD34+ Cord Blood Cells (CBC)

Large scale production of lineage-committed erythroid cells (CFU-E or Reticulocytes) can be manufactured from a starting population of stem cells or erythroblast precursors (e.g. cord blood cells, embryonic stem cells, hematopoietic stem cells and BFU-E) employing the methods described below.

Umbilical cord blood from healthy full-term newborns is collected in heparinized blood collection bags. A clean nucleated cell preparation is made by adding ammonium chloride lysis solution to cord blood, then centrifuging the mixture at 300×g for 15 minutes at room temperature. The supernatant is aspirated from the cell pellet, and the cell pellet is washed in BSSD with 5% human serum albumin (wash solution). The cells are centrifuged again at 300×g for 15 minutes at room temperature and the wash solution is removed from the cell pellet by aspiration. CD34+ cells are separated by magnetic cell sorting using MASC LS-columns (MACS®; Miltenyi Biotech, Gladbach, Germany) using established protocols. The CD34+ CBCs are subsequently re-suspended in CSM-55 at approximately 2 million cells/mL and cryopreserved using a controlled-rate freezer.

BSSD (Balanced Salt Solution with 4.5% Dextrose) is prepared as follows:
 To Balanced Salt Solution, Sterile Irrigating Solution (BSS; Baxter, Deerfield, Ill., USA) add 450±0.5 grams Dextrose (EMD Life Sciences, Gibbstown N.J. USA), QS to a final volume of 10.0 Liters with BSS.

CSM-55 (Cryogenic Storage Media 5% DMSO. 5% HSA) is prepared as follows:
 In a 2 liter bottle combine 1.4 liters of BSSD with 400 mLs of 25% HSA (25% solution human serum albumin from ZLB Behring, Ill., USA) and 200 mLs of 50% DMSO (50% dimethyl sulfoxide from Edwards Lifesciences Irvine Calif. USA).

Wash solution is prepared with 400 mLs of BSSD plus 100 mLs of 25% HSA.

CD34+ CBC Expansion in Suspension Cultures

The cells are subsequently re-suspended in StemSpan® H300 (StemCell Technology) supplemented with 1.0 U/mL recombinant human EPO (R&D Systems, Cat #287-TC), 10 LYOSPHERES™/L, and inoculated into a disposable HYCLONE™, perfusion BIOPROCESS CONTAINER™ (bioreactor) or equivalent, at a cell concentration of $1.0 \times 10^6$/mL. Cultures are maintained at 37° C. with 5% $CO_2$, 4% $O_2$, and balanced with Nitrogen, for 3 weeks using continuous flow of fresh culture media. On day 14, cultures are supplemented with the glucocorticoid antagonist Mifepristone to accelerate enucleation, as described by Miharada et al. 2006. Continuous flow of fresh culture media is maintained at a fixed rate under these conditions until harvest on day 21.

CBC Expansion on a Human ABM-SC Feeder Layer

Cryopreserved human ABM-SC are thawed and re-suspended in Advanced RPMI Media 1640 (INVITROGEN™) supplemented with 1.0 U/mL recombinant human EPO (R&D Systems, Cat #287-TC), 4 mM L-Glutamine, 10% lot selected, gamma-irradiated fetal bovine serum (Hyclone), and seeded at a density of 10,000 cells/cm² in 40 layer cell culture factories (Corning) and maintained at 37° C. under 5% $CO_2$, 4% $O_2$, and balanced with Nitrogen at 37° C. On day 5, one-half volume of spent media is removed from the cultures and replenished by adding back one-half volume of fresh media along with $1.0 \times 10^6$ CBC/mL. Discontinuous flow (on-off-on) of fresh culture media is subsequently engaged to enable the media conditions to cycle between fresh (on) to conditioned (off), and back to fresh media again (on). On day 14, cultures are supplemented with the glucocorticoid antagonist Mifepristone to accelerate enucleation, as described by above. Co-cultures are maintained under these conditions until harvest on day 21.

Example 15

ABM-SC Secrete Scavenger Receptors and Antagonists and Reduce Tumor Necrosis Factor-Alpha Levels in a Dose Dependent Manner Background: Embodiments of the present invention include methods and compositions for treating, reducing, or preventing adverse immune activity (such as inflammation or autoimmune activity) in a subject by delivering therapeutically effective amounts of exABM-SC or compositions produced by exABM-SC. Embodiments of the invention include utilization of exABM-SC, or compositions produced thereby, relying on the naturally occurring or basal level production of secreted compositions in vitro. Alternatively, embodiments of the invention also include utilization of exABM-SC, or compositions produced thereby, by manipulating the exABM-SC to modulate (up- or down-regulate) the quantity and kind of compositions produced (for example, by administration of pro-inflammatory factors such as TNF-alpha).

For example, it has now been found that exABM-SC produce at least one scavenger receptor for the cytokine Tumor Necrosis Factor-alpha (TNF-α), and at least one antagonist of the Interleukin-1 Receptor (IL-1R), and at least one binding protein (antagonist) of cytokine Interleukin-18 (IL-18). Accordingly, embodiments of the invention include methods and compositions for use and administration of stable cell populations (such as exABM-SC) that consistently secrete therapeutically useful proteins in their native form.

The term "stable cell population" as used herein means an isolated, in vitro cultured, cell population that when introduced into a living mammalian organism (such as a mouse, rat, human, dog, cow, etc.) does not result in detectable production of cells which have differentiated into a new cell type or cell types (such as a neuron(s), cardiomyocyte(s), osteocyte(s), hepatocyte(s), etc.) and wherein the cells in the cell population continue to secrete, or maintain the ability to secrete or the ability to be induced to secrete, detectable levels of at least one therapeutically useful composition (such as soluble TNF-alpha receptor, IL-1R antagonists, IL-18 antagonists, compositions shown in Table 1A, 1B and 1C, etc.).

For purposes of the present invention, "scavenger receptor" is intended to mean any soluble or secreted receptor (whether membrane bound or free in the extracellular milieu) capable of binding to and neutralizing its cognate ligand.

In addition to the pro-inflammatory factors listed above, in view of the present disclosure it is also understood that cell populations of the present invention may be treated with any number, variety, combination, and/or varying concentrations of factors now known or subsequently discovered or identified in order to manipulate the concentration and kind of compositions produced by cell populations of the present invention. For example, the cell populations of the invention may preferably be treated with factors such as: IL-1alpha, IL-1beta, IL-2, IL-12, IL-15, IL-18, IL-23, TNF-alpha, TNF-beta, and Leptin. This brief list of preferred factors, however, is not intended nor should it be construed as limiting with respect to the number of different compositions that can be used to treat cell populations of the present invention, nor are these compositions limited to proteins, as is it is also appreciated that many other types of compounds could also be used to manipulate the cell populations of the present invention (including, by way of brief examples, other biological macromolecules such as nucleic acids, lipids, carbohydrates, etc. and small molecules and chemicals such as dimethylsulfoxide (DMSO) and nitrous oxide (NO), etc).

Methods: Production of serum-free conditioned media was produced as described below for use in enzyme-linked immunosorbant assays (ELISA) (also described below). Cryopreserved human exABM-SC (Lot #MFG-05-15; at ~43 population doublings) were thawed and re-suspended in Advanced DMEM (GIBCO™; Catalog #12491-015, Lot #1216032 (Invitrogen Corp., Carlsbad, Calif. USA)) supplemented with 4 mM L-glutamine (Catalog #SH30034.01. Lot #134-7944, (HYCLONE© Laboratories Inc., Logan, Utah, USA)) with and without 10 ng/mL TNF-α. Cell suspensions were then seeded in T-225 $cm^2$ CELLBIND™ (Corning Inc., NY, USA) culture flasks (culture surfaces treated with a patented microwave plasma process; see, U.S. Pat. No. 6,617,152) (n=3) at 10,000, 20,000, 40,000 cells/$cm^2$ in 36 mL of media (n=3 per condition). Heat-inactivated cells seeded at 40,000 cells/$cm^2$ were used as a negative control. Cells were heat-inactivated by transferring an aliquot to a sterile tube and incubating it for ~40 minutes in a 70° C. heat block containing water (for efficient heat transfer). Cultures were placed in a 37° C. humidified trigas incubator (4% $O_2$, 5% $CO_2$, balanced with nitrogen) for approximately 24 hours. Cultures were then re-fed with fresh media on same day to remove non-adherent debris and returned to the incubator. On day 3, cell culture media was concentrated using 20 mL CENTRICON™ PLUS-20 Centrifugal Filter Units (Millipore Corp., Billerica, Mass., USA), as per manufacturer's instructions. Briefly, concentrators were centrifuged for 45 minutes at 1140×G. Concentrated supernatants (100× final concentration) were transferred to clean 2 mL cryovials and stored at −80° C. until later use.

To determine the levels of certain secreted proteins produced from the human ABM-SC in these adherent cultures, enzyme-linked immunosorbant assays (ELISA) were performed on day 3, 100× concentrated, conditioned cell culture supernatants collected as described above. On the day of assay, supernatants were thawed and equilibrated to room temperature before use. ELISA analysis was performed to detect TNF-α, soluble TNF-RI (sTNF-RI), soluble TNF-RII (sTNF-RII), IL-1 receptor antagonist (IL-IRA) and IL-2 receptor alpha (conducted as per manufacturer's instructions; all kits were purchased from R&D Systems, Inc. (Minneapolis, Minn., USA)).

Figure 21:
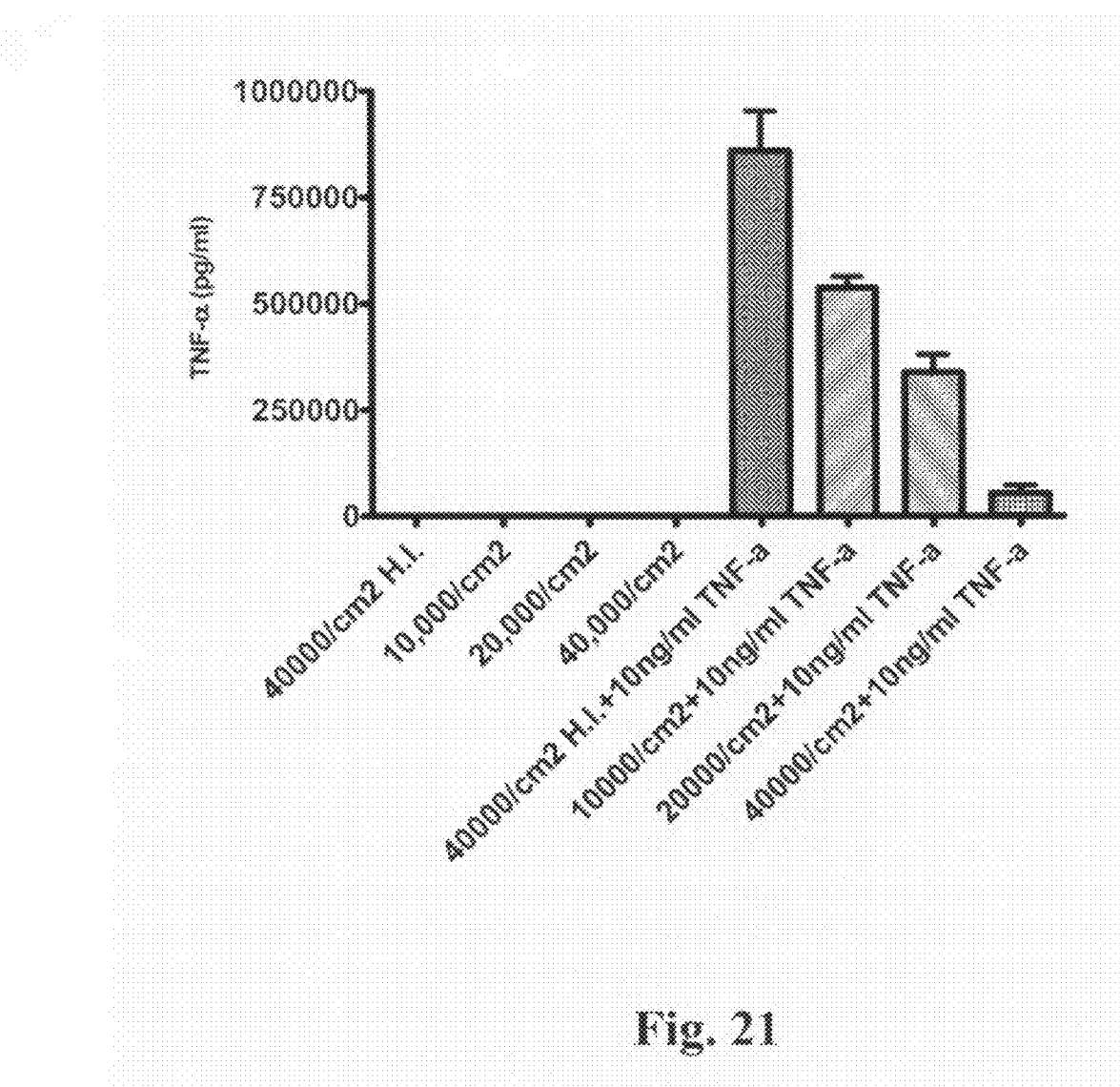
FIG. 21 demonstrates that exABM-SC reduce TNF-α levels in vitro in a dose-dependent manner. Human exABM-SC (at about 43 population doublings) were tested for their ability to reduce TNF-α levels when cultured at various seeding densities (e.g. 10,000 cells/cm$^2$, 20,000 cells/cm$^2$, and 40,000 cells/cm$^2$). Cells were cultured for 3 days in serum-free Advanced DMEM (GIBCO™) either alone or supplemented with 10 ng/mL TNF-α. Heat inactivated cells were also included as a negative control. Concentration of TNF is shown on the Y-axis. (Y-axis represents concentration of substances in media which has been concentrated 100×).
Figure 22:
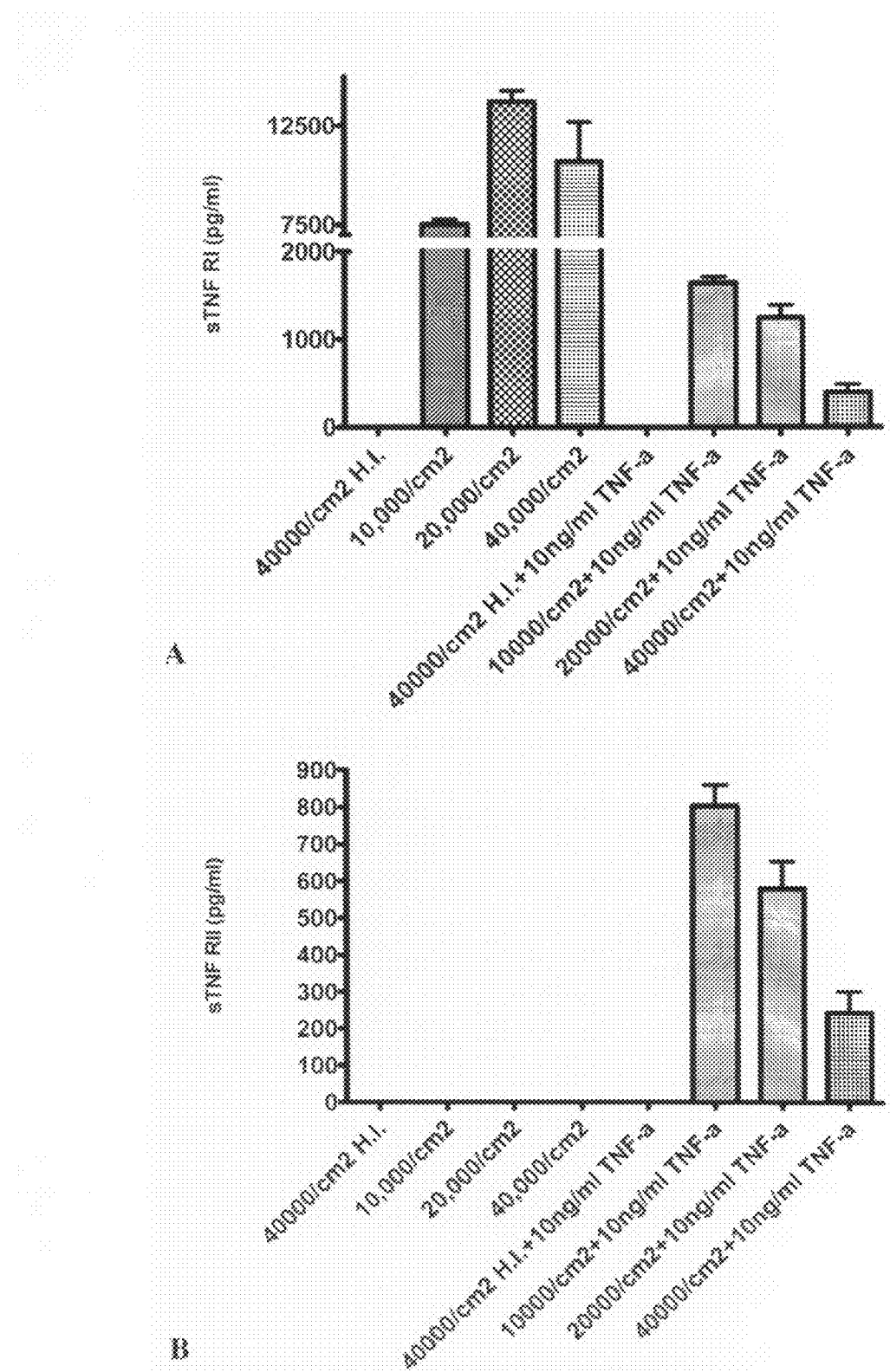
FIGS. 22A and 22B demonstrates that reduction of TNF-α appears to be mediated by the secretion of sTNF-RI and sTNF-RII by exABM-SC (at about 43 population doublings). Basal level expression of sTNF-RI occurs in the absence of a pro-inflammatory inducer (A), while sTNF-RII is detected at appreciable levels only when first primed with TNF-α (B). These data reveal an inverse relationship between the number of cells seeded and the levels of both sTNF-RI and sTNF-RII detected, suggesting that the secreted receptors themselves may be binding to and masking the TNF-α. (Y-axis represents concentration of substances in media which has been concentrated 100×).
Figure 23:
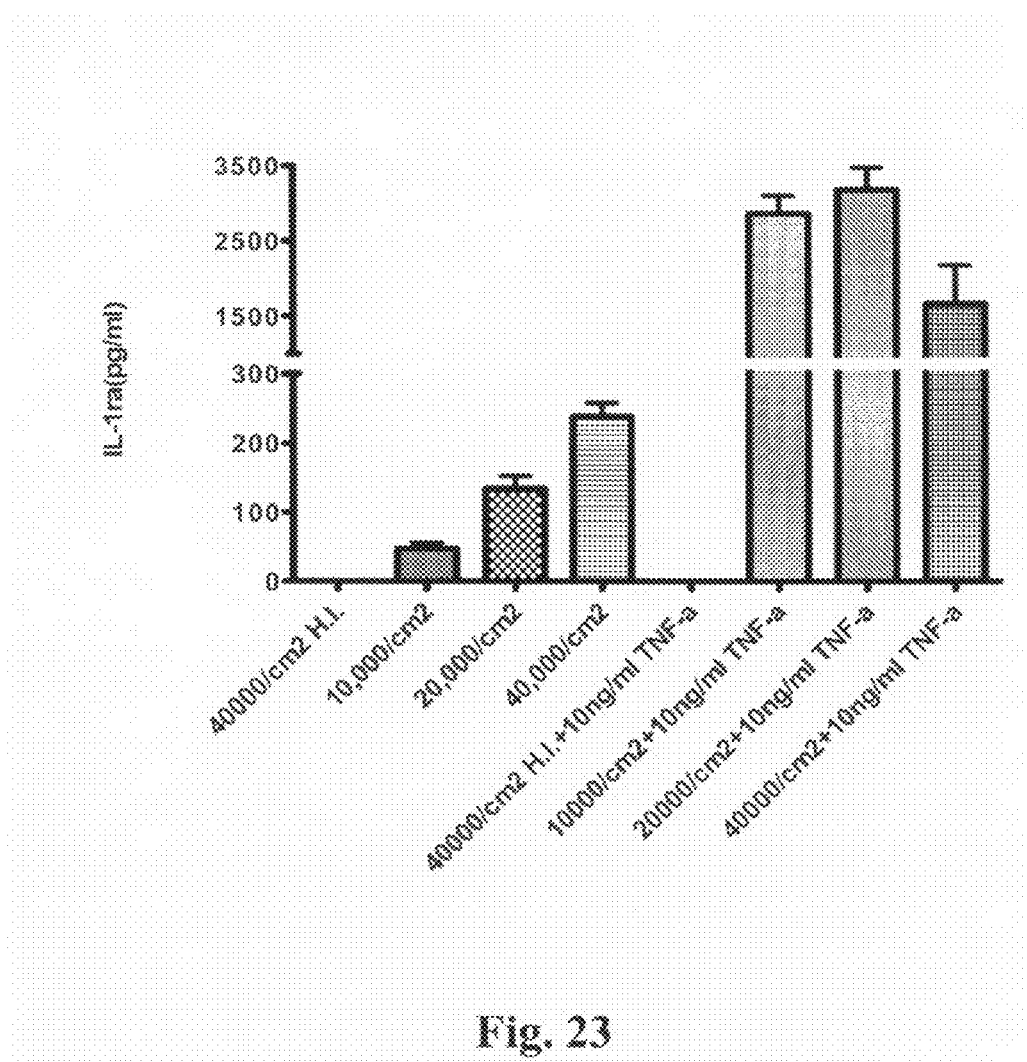
FIG. 23 demonstrates that secretion levels of IL-IRA (by exABM-SC at about 43 population doublings) is dose-dependent. Basal level expression of IL-IRA occurs in the absence of a pro-inflammatory inducer, but when primed when TNF- α, soluble levels increase approximately 10-fold. (Y-axis represents concentration of substances in media which has been concentrated 100×).

The results demonstrate that therapeutically relevant levels of secreted scavenger receptors (e.g. sTNF-RI) and receptor antagonists (e.g. IL-IRA) are produced by these adherent cultures and that these levels can be controlled by adjusting cell concentration or dose (FIG. 21-23). Importantly, these data also demonstrate that the cells respond to the inflammatory milieu in which they are placed. For example, following treatment with the potent inflammatory cytokine TNF-alpha, the cells up-regulate secretion of sTNF-RII (FIG. 22B) and IL-IRA (FIG. 23). Interestingly, in these sample cultures, the levels of TNF-alpha were significantly reduced with each increase in cell seeding density (FIG. 21), suggesting that the TNF-alpha itself was sequestered in some way by either the ABM-SCs or factors that they secrete.

It is well established that both sTNF-RI and sTNF-RII can bind and neutralize the biological activity of TNF-alpha. Since the measurable levels of both forms of the TNF receptor, as well as TNF-alpha itself, are each reduced significantly with each increase in cell seeding density, it is likely that the ABM-SC derived sTNF-RI and sTNF-RII are binding to and masking TNF-alpha in this assay system.

Of the soluble receptors and receptor antagonists measured, detectable levels were not seen in cultures containing heat-inactivated cells only. Statistical comparisons between assay conditions were determined by one-way ANOVA.

Example 16

Osteogenesis Induction Assay

Human ABM-SC Cells do not Exhibit a Bone Differentiation Characteristic In Vitro when Cell Populations Expanded Beyond Approximately 25 Population Doublings are Exposed to Standard Osteoinductive Conditions or when Cell Populations Expanded Beyond Approximately 30 Population Doublings are Exposed to Enhanced Osteoinductive Conditions Methods: Human ABM-SC and exABM-SC were seeded at 3100 cells/$cm^2$ in 6-well culture dishes (Corning, Catalog #3516) with 2.4 mL Mesenchymal Stem Cell Basal Medium (MSCBM™; Lonza, Catalog #PT-3238) supplemented with MSCGM™ SingleQuot Kit (Lonza, Catalog #PT-4105) per well, hereafter referred to as Mesenchymal Stem Cell Growth Medium (MSCGM™). Approximately four hours later, the MSCGM™ was changed to the appropriate test conditions. Negative control wells were those re-fed with either MSCGM™ alone, or MSCGM™ supplemented with 5 ng/mL recombinant mouse Noggin/Fc Chimer (R&D Systems, Catalog #719-NG). The test wells were those treated with either Osteogenesis Induction Medium (OIM; Lonza Catalog #PT-3924 and #PT-4120) alone (standard osteoinductive conditions) or OIM supplemented with 5 ng/mL recombinant mouse Noggin/Fc Chimer (enhanced osteoinductive conditions). Cultures were then maintained in a humidified $CO_2$ incubator at 37° C. and re-fed with fresh medium every 34 days for 2 weeks. After 14 days, cultures were processed for calcium determination using the Calcium Liquicolor kit (Stanbio, Catalog #0150-250), as per manufacturer's instructions. Plates were read at 550 nm using a SpectraMax Plus$^{384}$ microplate reader.

Results: Human ABM-SC and exABM-SC derived from research lot #MCB109 were cultured under standard osteoinductive conditions (OIM only) or under enhanced osteoinductive conditions (OIM and the morphogen Noggin; OIM+Noggin). Negative control cultures were maintained in either growth media alone (MSCGM™) or MSCGM™ supplemented with Noggin (MSCGM™+Noggin).

ABM-SC at about 16 population doublings exhibited a calcium deposition increase of approximately 6-fold when the OIM media was supplemented with Noggin (i.e., ABM-SC at about 16 population doublings deposited ~5 micrograms calcium/well under OIM conditions and ~30 micrograms/well under OIM+Noggin conditions). ABM-SC lost the capacity to deposit detectable levels of calcium beyond about 16 population doublings under standard OIM conditions, however, this could be reversed by supplementing with Noggin (i.e., exABM-SC at about 25 population doublings deposited no detectable calcium under OIM conditions whereas these same cells deposited ~5 micrograms calcium/well under OIM+Noggin conditions). In contrast, beyond about 30 population doublings (e.g., at about 35 and 43 populations doublings) exABM-SC did not deposit detectable levels of calcium under any of the conditions tested (standard or enhanced OIM).

Example 17

Expression of IL-1 Receptor Antagonist (IL-1RA) and IL-18 Binding Protein (IL-18BP) by ABM-SC Methods: Human ABM-SC which had undergone about 43 cell population doublings (lot #P17-T2S1F1-5) were thawed and seeded in AFG growth medium supplemented with Brefeldin A at 3 micrograms/mL (1×) and placed in a humidified 5% $CO_2$ incubator at 37° C. for 24 hours. Cultured cells were then removed from the culture flasks using porcine trypsin, washed and prepared for flow cytometry, as per CAL-TAG FIX & PERM® staining protocol (CALTAG LABORATORIES; now part of Invitrogen Corp. (Carlsbad, Calif., USA). Cells were stained with either FITC conjugated mouse anti-human IL-1 Receptor Antagonist (IL-1RA; eBioscience, Catalog #11-7015, clone CRM17) antibody neat or unlabeled rabbit anti-IL-18 Binding Protein (IL-18BP; Epitomics, Catalog #1893-1, clone EP1088Y) at a 1:10 dilution, both for 45 minutes at room temperature. FITC-rabbit FITC-labeled goat anti-rabbit antibody was then used to detect the IL-18BP. Isotype matched controls were included as a negative control (Beckman Coulter).

Figure 24A:
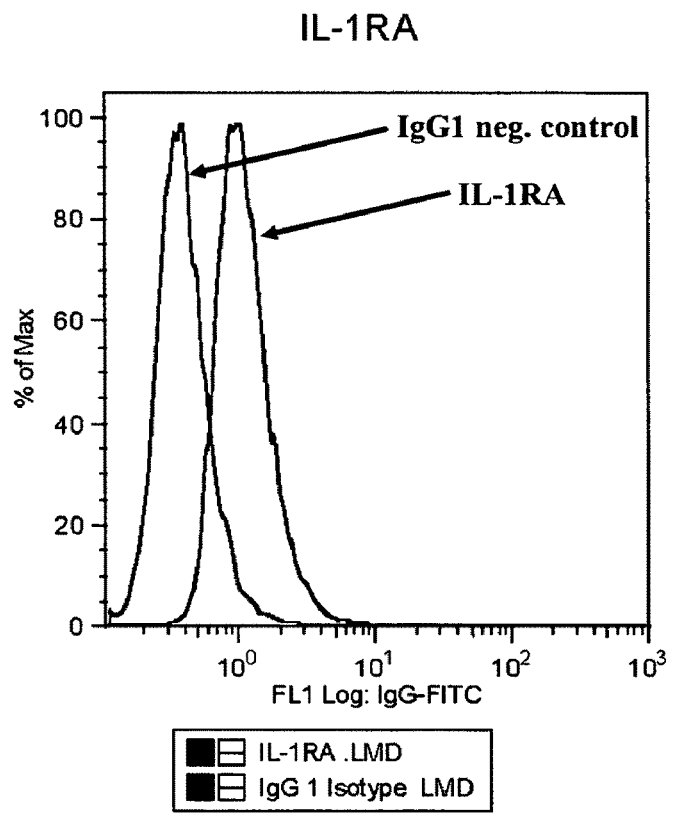
FIG. 24 shows expression of IL-1 receptor antagonist (IL-1RA) and IL-18 binding protein (IL-18BP) by exABM-SC. Human exABM-SC express basal levels of IL-1 receptor antagonist (IL-1RA.
Figure 24:
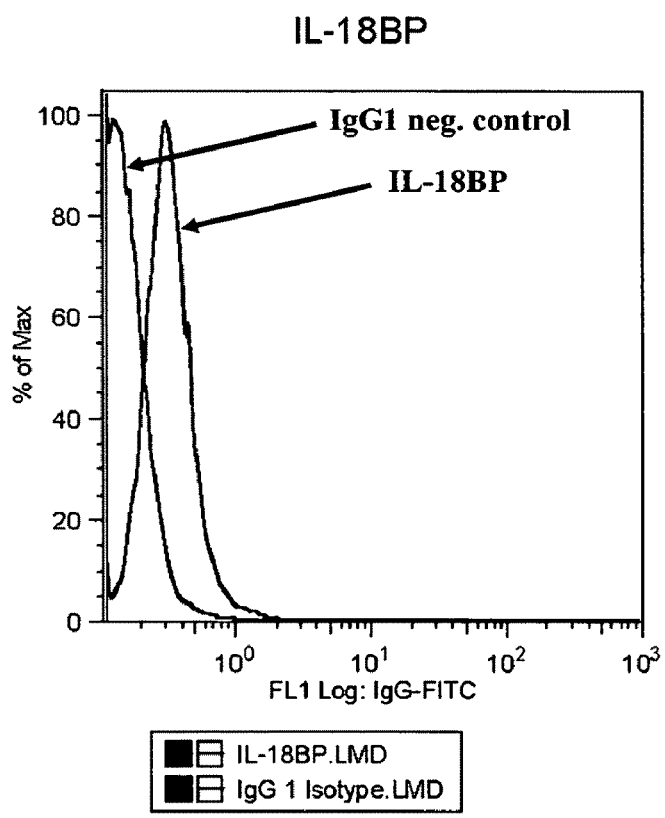

Results: Human exABM-SC express basal levels of IL-1 receptor antagonist (IL-1RA; FIG. 24A) and IL-18 binding protein (IL-18BP; FIG. 24B) even in the absence of an inflammatory signal such as TNF-alpha.

Example 18

Human ABM-SC Reduce Expression of TNF-Alpha and IL-13 while Simultaneously Increasing Expression of IL-2

Methods: Human peripheral blood mononuclear cells (PBMC) were co-cultured in RPMI-1640 containing 5% Human Sera Albumin, 10 mM HEPES, 2 mM glutamine, 0.05 mM 2-mercaptoethanol, 100 U/mL penicillin, and 100 microg/mL streptomycin, in a 24 well plate with either 1) Mitomycin-C treated PBMC from same donor (Responder+Self) or 2) Mitomycin-C treated PBMC derived from a different donor (Responder+Stimulator). PBMC from each source were each seeded at $4\times10^5$ cells/well. For each condition, cultures were supplemented with or without human ABM-SC at a seeding density of 40,000 cells/well. Cultures were maintained in a humidified 5% $CO_2$ incubator at 37° C. for 7 days to condition the media. Conditioned cell culture supernatants were collected and analyzed for the presence of the various cytokines using the SEARCHLIGHT™ 9-Plex assay (Pierce Protein Research Products, Thermo Fisher Scientific Inc., Rockford, Ill.). Statistical analysis was performed by one-way ANOVA (analysis of variance).

Figure 25A:
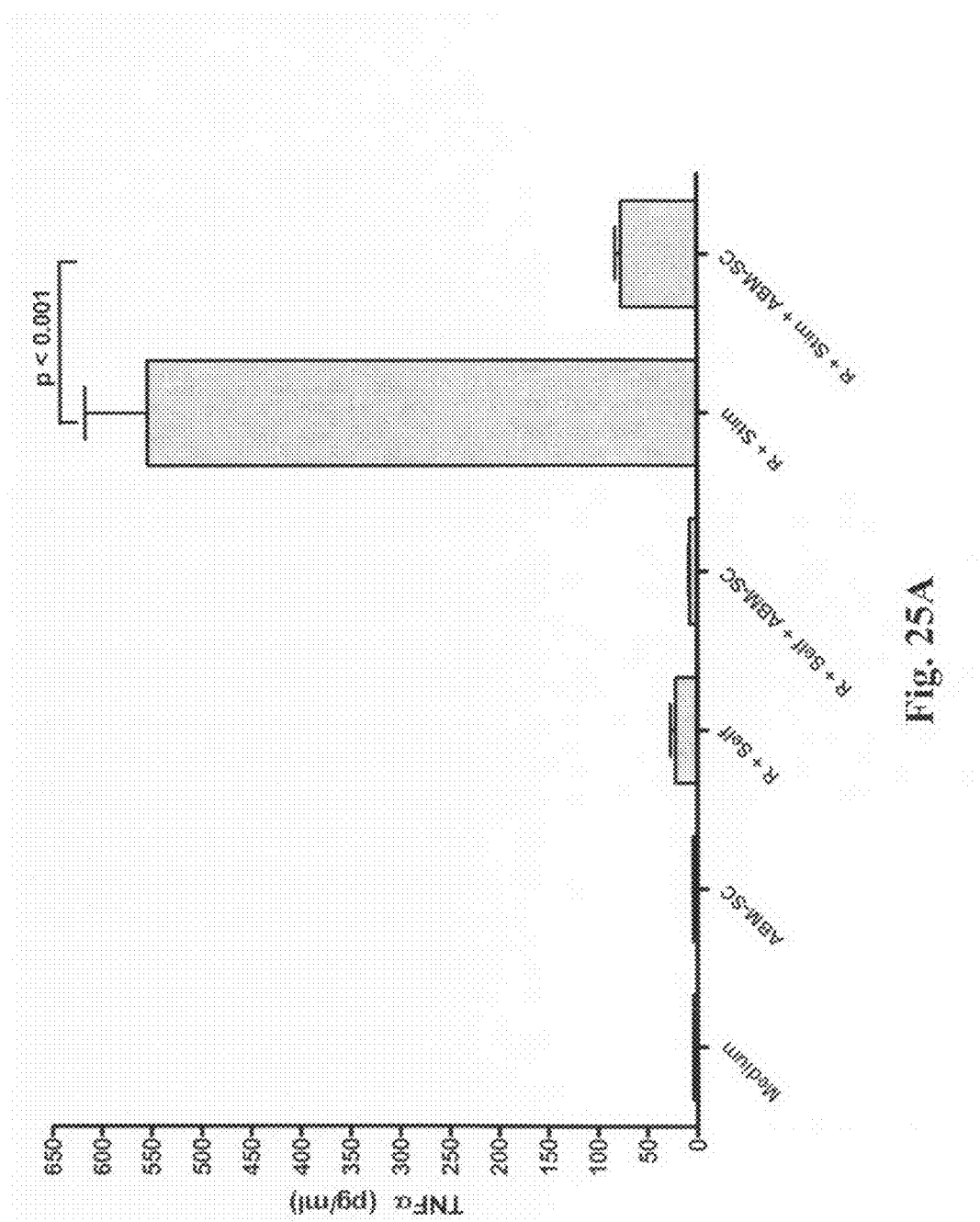
FIGS. 25A, B, and C show that human ABM-SC reduce levels of TNF-alpha (FIG. 25A) and IL-13 (FIG. 25B) while simultaneously inducing elevated expression of IL-2 (FIG. 25C) in a Mixed PBMC reaction assay. (R=Responder PBMC, Self=Mitomycin-C treated PBMC isolated from same donor as Responder, Stim=Mitomycin-C treated PBMC isolated from a different donor.)
Figure 25B:
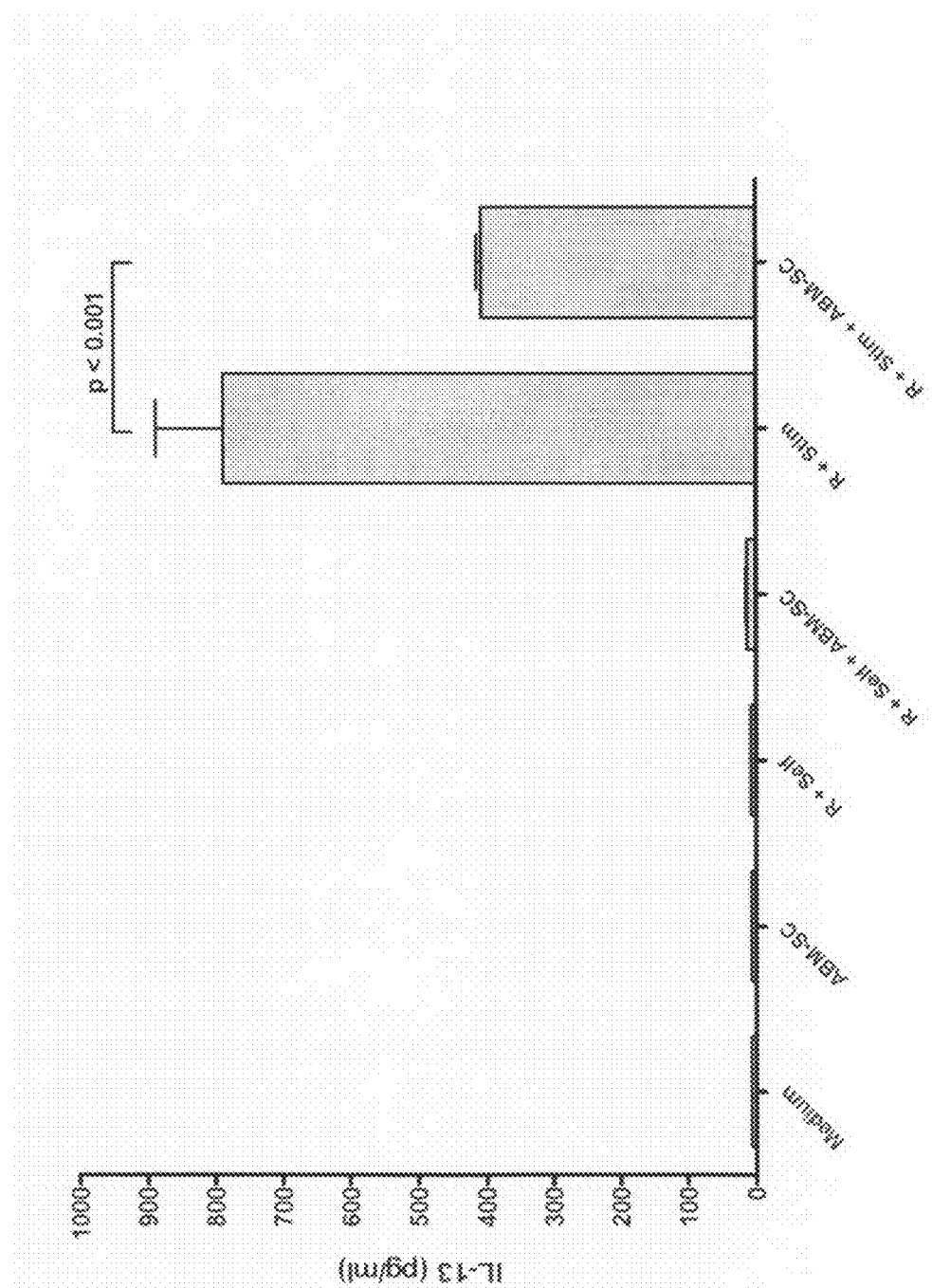
Figure 25C:
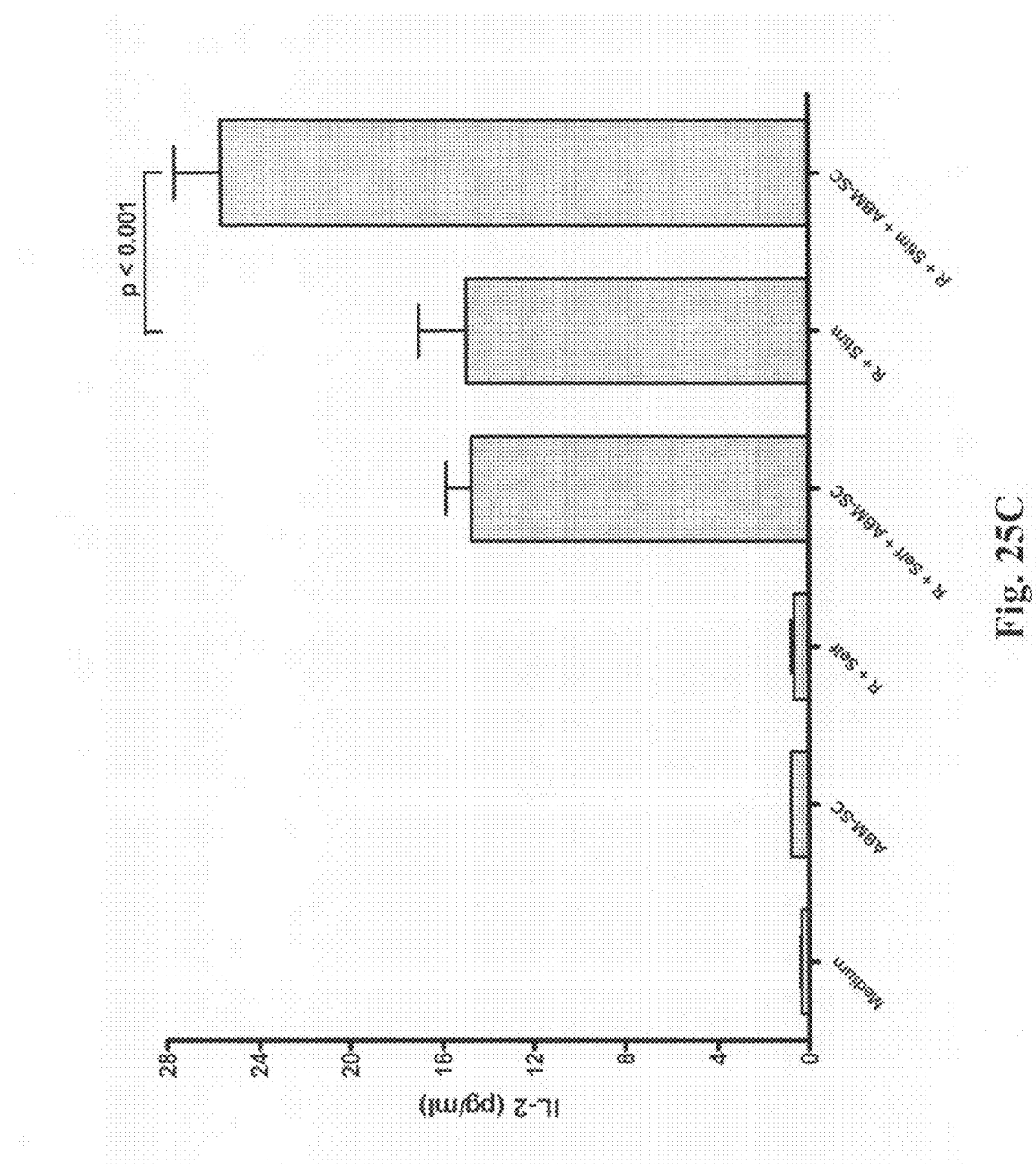

Results: Co-culture of allogeneic PBMC (Responders+Stimulators) resulted in a marked increase in the levels of TNF-alpha and IL-13, as would be expected for a mixed PBMC reaction. When challenged with human ABM-SC, however, both IL-13 and TNF-alpha were significantly reduced (P<0.001), suggesting that ABM-SC could be utilized therapeutically to treat chronic inflammatory disorders or graft rejection by reducing focal or serum levels of inflammatory mediators. See, FIGS. 25A, B, and C.

Notably, ABM-SC induced elevated expression of IL-2 in both autologous (Responders+Self) and allogeneic (Responders+Stimulators) mixed PBMC cultures (P<0.001) while simultaneously suppressing PBMC proliferation. While this result appears somewhat paradoxical given the importance of IL-2 in promoting T cell proliferation, recently it has been shown in mice that disruption of the IL-2 pathway results in lymphoid hyperplasia and autoimmunity rather than immune deficiency, suggesting that the major physiological role of IL-2 may be to limit or regulate, rather than enhance T cell responses (Nelson, "IL-2, Regulatory T-Cells, and Tolerance," *Jour. Immunol.* 172: 3983-3988 (2004)). Additionally, it is now known that IL-2 is also critical for promoting self-tolerance by suppressing T cell responses in vivo and that the mechanism by which this occurs is through the expansion and maturation of CD4+/CD25+ regulatory T cells. It is, therefore, contemplated that ABM-SC could be employed therapeutically to induce T-cell tolerance by indirectly supporting the maturation of T regulatory cells through the induced up-regulation of IL-2.

Example 19

Human ABM-SC Inhibit Mitogen-Induced Peripheral Blood Mononuclear Cell Proliferation Methods: Human adult bone-marrow derived somatic cells (ABM-SC) were cultured in vitro for 96 hours in a humidified incubator under 5% $CO_2$ then passaged onto 96-well round bottom plates at a concentration of 25,000 viable cells/mL in RPMI-complete media (HYCLONE™). Human peripheral blood mononuclear cells (PBMC) were cultured either separately at 250,000 cells/mL in RPMI-complete media, or with ABM-SC Lots RECB801 (sub-cultured to about 19 population doublings) or RECB906 (sub-cultured to about 43 population doublings). To stimulate PBMC proliferation, cultures were inoculated with 2.5 microg/mL phytohaemagglutinin (Sigma Chemical Co.). After 56 hours in culture, cells were pulsed with Thymidine-[Methyl-3H] (Perking Elmer, 1 microCi/well). Cells were harvested at 72 hours using a Filtermaster harvester onto glass filters. Filters were read in Omnifilter platers using an NXT TopCount Scintillation counter. Human mesenchymal stem cells were included as a positive control. (Human mesenchymal stem cells were obtained from Cambrex Research Bioproducts; now owned by Lonza Group, Ltd, Basel, Switzerland). Statistical analysis was performed by one-way ANOVA (analysis of variance).

Figure 26:
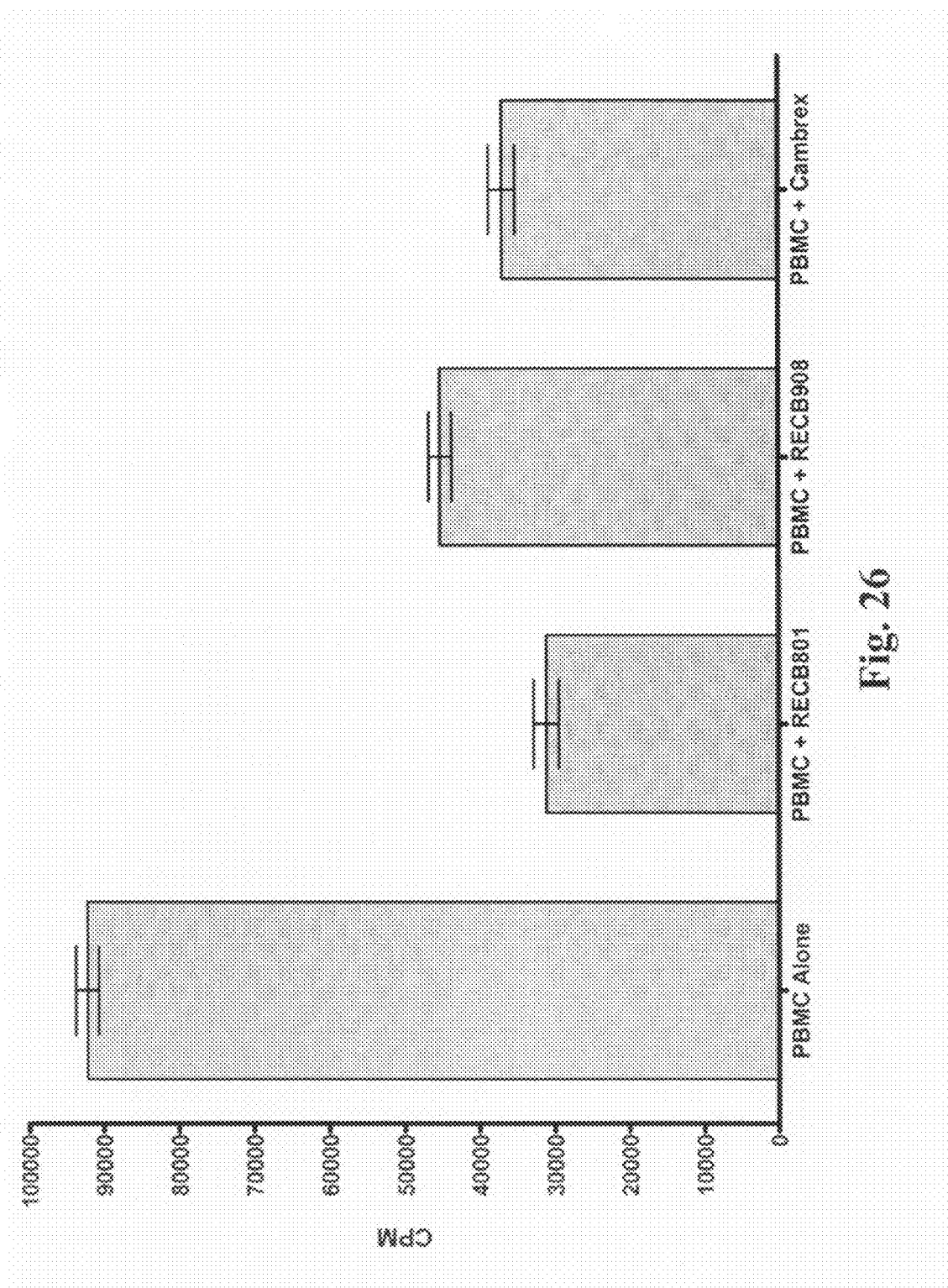
FIG. 26 shows a graphical representation of inhibition of mitogen-induced human peripheral blood mononuclear cell (PBMC) proliferation using human ABM-SC. RECB801 represents a particular lot of ABM-SC that have been sub-cultured to about 19 population doublings and #RECB906 represents a particular lot of ABM-SC that have been sub-cultured to about 43 population doublings. To stimulate PBMC proliferation, cultures were inoculated with 2.5 microg/mL phytohaemagglutinin. After 56 hours in culture, cells were pulsed with Thymidine-[Methyl-3H] and at 72 hours isotope incorporation was quantitated (CPM). Human mesenchymal stem cells were included as a positive control.

Results: PBMC-induced proliferation was significantly reduced when challenged with either lot of ABM-SC (P<0.001). See, FIG. 26. Mesenchymal stem cells (MSC) were included as a positive control. These data suggest that ABM-SC not only inhibit mitogen-induced proliferation of the total PBMC preparation, but that the presence of ABM-SC in this assay system does not induce proliferation of

REFERENCES

Cory et al., "Murine erythroid cell lines derived with c-myc retroviruses respond to leukemia-inhibitory factor, erythropoietin, and interleukin 3," *Cell Growth Differ.* 2 (3): 165-72 (1991).

Dexter et al., "Molecular and cell biological aspects of erythropoiesis in long-term bone marrow cultures," *Blood.* 58(4):699-707 (1981).

Dia et al., "Human burst-forming units-erythroid need direct interaction with stem cell factor for further development," *Blood.* 78(10):2493-7 (1991).

Hodohara et al., "Stromal cell-derived factor-1 (SDF-1) acts together with thrombopoietin to enhance the development of megakaryocytic progenitor cells (CFU-MK)," *Blood.* 95(3):769-75 (2000).

Miharada et al., "Efficient enucleation of erythroblasts differentiated in vitro from hematopoietic stem and progenitor cells," *Nature Biotech.* 10:1255-56 (2006).

Müller-Ehmsen et al., "Rebuilding a damaged heart: long-term survival of transplanted neonatal rat cardiomyocytes after myocardial infarction and effect on cardiac function," *Circulation.* 105(14):1720-6 (2002).

Nelson, "IL-2, Regulatory T-Cells, and Tolerance," *Jour. Immunol.* 172: 3983-3988 (2004).

Quesenberry et al., "Studies on the regulation of hemopoiesis," *Exp. Hematol.* 13: Suppl. 16:43-8 (1985).

Roecklein and Torok-Storb, "Functionally distinct human marrow stromal cell lines immortalized by transduction with the human papilloma virus E6/E7 genes," *Blood.* 85(4): 997-1005 (1995).

Shao et al., "Effect of activin-A on globin expression in purified human erythroid progenitors," Blood. February; 79(3):773-81 (1992).

Ullrich et al., "In vivo hematologic effects of recombinant interleukin-6 on hematopoiesis and circulating numbers of RBCs and WBCs," *Blood.* 73(1): 108-10 (1989).

The invention claimed is:

1. A method of administering a therapeutically useful amount of a biological composition or compositions to an organ, tissue, or subject, comprising:
   (a) isolating a biological composition or compositions from culture media in which an isolated population of bone marrow-derived self-renewing colony forming somatic cells (CF-SC) had been grown; and,
   (b) administering said biological composition or compositions to said organ, tissue, or subject,
wherein said CF-SC do not have multipotent differentiation capacity, wherein said CF-SC have a normal karyotype, wherein said CF-SC are non-immortalized, wherein said CF-SC express CD13, CD44, CD49c, CD90, HLA Class-1 and β (beta) 2-Microglobulin, and wherein said CF-SC do not express CD10, CD34, CD45, CD62L, or CD106.

2. A method of administering a therapeutically useful amount of a biological composition or compositions to an organ, tissue, or subject, comprising:
   (a) isolating a biological composition or compositions from culture media in which an isolated population of bone marrow-derived self-renewing colony forming somatic cells (CF-SC) had been grown; and,
   (b) administering said biological composition or compositions to said organ, tissue, or subject,
wherein said CF-SC do not have multipotent differentiation capacity, wherein said CF-SC have a normal karyotype, wherein said CF-SC are non-immortalized, and wherein said CF-SC are obtained from bone marrow by steps comprising:
   i) incubating bone marrow cells under a low oxygen condition such that said bone marrow cells when allowed to adhere to a tissue culture-treated surface produce adherent colony forming units; and,
   ii) passaging cells in said adherent colony forming units at low cell seeding densities.

3. A method of preventing tissue damage or of repairing, treating, or promoting regeneration of damaged tissue in an organ, tissue, or subject, comprising the method of claim 1, wherein damage to said organ, tissue or subject is prevented, repaired or treated or regeneration of damaged tissue is promoted.

4. A method of preventing tissue damage or of repairing, treating, or promoting regeneration of damaged tissue in an organ, tissue, or subject, comprising the method of claim 2, wherein damage to said organ, tissue or subject is prevented, repaired or treated or regeneration of damaged tissue is promoted.

5. A method of treating or reducing inflammation, immune, or autoimmune activity in an organ, tissue, or subject, comprising the method of claim 1, wherein inflammation, immune, or autoimmune activity in said organ, tissue or subject is reduced.

6. A method of treating or reducing inflammation, immune, or autoimmune activity in a organ, tissue, or subject, comprising the method of claim 2, wherein inflammation, immune, or autoimmune activity in said organ, tissue or subject is reduced.

7. The method of claim 2, wherein said low oxygen condition is about 5% oxygen.

8. The method of claim 2, wherein said low oxygen condition is selected from the group consisting of:
   a) less than about 20% oxygen;
   b) less than about 15% oxygen;
   c) less than about 10% oxygen;
   d) less than about 5% oxygen;
   e) between about 1 to 10% oxygen;
   f) between about 2 to 7% oxygen;
   g) between about 3 to 6% oxygen;
   h) between about 4 to 6% oxygen; and,
   i) between about 4 to 5% oxygen.

9. The method of claim 2, wherein said low cell seeding density is less than about 200 cells/cm$^2$.

10. The method of claim 2, wherein said low cell seeding density is less than about 100 cells/cm$^2$.

11. The method of claim 2, wherein said low cell seeding density is less than about 50 cells/cm$^2$.

12. The method of claim 2, wherein said low cell seeding density is less than about 30 cells/cm$^2$.

13. The method of claim 2, wherein said low cell seeding density is selected from the group consisting of:
   a) less than about 2500 cells/cm$^2$;
   b) less than about 1000 cells/cm$^2$; and,
   c) less than about 500 cells/cm$^2$.

* * * * *